US012188097B2

(12) United States Patent
Sahin et al.

(10) Patent No.: US 12,188,097 B2
(45) Date of Patent: Jan. 7, 2025

(54) METHODS AND COMPOSITIONS FOR PREDICTION OF THERAPEUTIC EFFICACY OF CANCER TREATMENTS AND CANCER PROGNOSIS

(71) Applicants: Astellas Pharma Inc., Tokyo (JP); TRON-Translationale Onkologie an der Universitätsmedizin der Johannes Gutenberg-Universität Mainz gGmbH, Mainz (DE)

(72) Inventors: Ugur Sahin, Mainz (DE); Ozlem Tureci, Mainz (DE); Daniel Maurus, Mainz (DE)

(73) Assignees: Astellas Pharma Inc., Tokyo (JP); TRON-Translationale Onkologie an der Universitätsmedizin der Johannes Gutenberg-Universität Mainz, Mainz (DE)

( * ) Notice: Subject to any disclaimer, the term of this patent is extended or adjusted under 35 U.S.C. 154(b) by 0 days.

(21) Appl. No.: 18/330,112

(22) Filed: Jun. 6, 2023

(65) Prior Publication Data

US 2024/0110247 A1 Apr. 4, 2024

Related U.S. Application Data

(62) Division of application No. 17/133,107, filed on Dec. 23, 2020, now Pat. No. 11,732,308, which is a division of application No. 15/565,306, filed as application No. PCT/EP2016/058061 on Apr. 13, 2016, now Pat. No. 10,927,413.

(30) Foreign Application Priority Data

Apr. 15, 2015 (WO) ................ PCT/EP2015/058212

(51) Int. Cl.
*C12Q 1/6886* (2018.01)
*C12Q 1/6883* (2018.01)
*A61K 39/395* (2006.01)
*A61K 47/68* (2017.01)

(52) U.S. Cl.
CPC ......... *C12Q 1/6886* (2013.01); *C12Q 1/6883* (2013.01); *A61K 39/39558* (2013.01); *A61K 47/6801* (2017.08); *C12Q 2600/118* (2013.01); *C12Q 2600/156* (2013.01)

(58) Field of Classification Search
None
See application file for complete search history.

(56) References Cited

U.S. PATENT DOCUMENTS 10,927,413 B2 2/2021 Sahin et al.
2016/0008465 A1 1/2016 Sahin et al.
2018/0073077 A1 3/2018 Sahin et al.

FOREIGN PATENT DOCUMENTS

WO WO 2014/146672 A1 9/2014
WO WO 2014/146778 A1 9/2014

OTHER PUBLICATIONS

Al-Moundhri et al., *World Journal of Gastroenterology*, 16(27): 3432-3436 (2010).
Chung et al., *PLOS One*, 9(8): 1-8 e104968 (2014).
Crusius et al., *Annals Oncology*, 19: 1894-1902 (2008).
Deans et al., *Am. J. Clin. Nutr.*, 89: 1164-1172 (2009).
Hirvinen et al., *J Translational Med.*, 11:193, p. 1-12 (2013).
Lindstrom, et al., *Human genetics*, 118.3 (2005): 339-347.
Mellor et al., *Journal of Hematology & Oncology*, 6(1): 1-10 (2013).
Miteva et al., *Tumor Biol.*, 35: 12655-12664 (2014).
Saeki et al., *Gastroenterology*, 140: 892-902 (2011).
Sahin et al., *Clin. Cancer Res.*, 14(23): 7624-7634 (2018).
Tirino et al., *Int. J. Mol. Sci.*, 19, 2659: 1-21 (2018).
Wu et al., *World Journal of Gastroenterology*, 16(44): 5635-5641 (2010).
Yang et al., *PLOS One*, 9(6): 1-11 e100326 (2014).
Yin et al., *Clin. Cancer Res.*, 17(6): 1632-1640 (2011).
Zhang et al., *Journal of Clinical Oncology*, 25(24): 3712-3718 (2007).
Zhang et al., *Mutagenesis*, 27(1): 67-76 (2012).
Zheng et al., *Mol. Biol. Rep.*, 40:5791-5796 (2013).
The International Bureau of WIPO, International Preliminary Report on Patentability for International Application No. PCT/EP2016/058061 (Oct. 17, 2017).
U.S. Appl. No. 10/537,002, 2006/0035852, U.S. Pat. No. 7,527,933.
U.S. Appl. No. 12/326,997, 2009/0155817, U.S. Pat. No. 8,088,588.
U.S. Appl. No. 12/423,153, 2009/0208498, U.S. Pat. No. 8,586,047.
U.S. Appl. No. 13/296,620, 2012/0258091, U.S. Pat. No. 8,637,012.
U.S. Appl. No. 14/043,109, 2014/0186338, abandoned.
U.S. Appl. No. 14/821,411, 2015/0337052, abandoned.
U.S. Appl. No. 15/650,092, 2017/0320963, U.S. Pat. No. 10,414,824.
U.S. Appl. No. 11/596,649, 2008/0166350, U.S. Pat. No. 9,044,382.
U.S. Appl. No. 14/676,254, 2015/0315287, U.S. Pat. No. 9,775,785.
U.S. Appl. No. 15/448,831, 2017/0215536, abandoned.
U.S. Appl. No. 17/079,326, 2021/0145700, pending.
U.S. Appl. No. 12/094,530, 2009/0169547, U.S. Pat. No. 8,168,427.
U.S. Appl. No. 13/306,545, 2012/0164160, U.S. Pat. No. 9,499,609.
U.S. Appl. No. 13/425,538, 2012/0195830, U.S. Pat. No. 9,212,228.
U.S. Appl. No. 14/661,882, 2015/0252104, U.S. Pat. No. 9,751,934.

(Continued)

*Primary Examiner* — Carla J Myers
(74) *Attorney, Agent, or Firm* — Neal, Gerber & Eisenberg LLP; Kevin O'Connor

(57) ABSTRACT

The invention generally relates to methods and compositions for the prediction of therapeutic efficacy of cancer treatments and the prognosis of cancer. The invention discloses markers that are associated with favorable and unfavorable outcomes, respectively, in certain cancer treatments and are useful as prognostic markers for cancer. Methods involving these markers are disclosed for predicting cancer therapy benefit and prognosing clinical outcome for cancer patients.

24 Claims, 16 Drawing Sheets

Specification includes a Sequence Listing.

(56) References Cited

OTHER PUBLICATIONS

U.S. Appl. No. 14/661,846, 2015/0252103, U.S. Pat. No. 10,174,104.
U.S. Appl. No. 15/069,511, 2016/0185860, U.S. Pat. No. 10,017,564.
U.S. Appl. No. 15/710,252, 2018/0127489, U.S. Pat. No. 10,738,108.
U.S. Appl. No. 16/919,969, 2020/0385448, pending.
U.S. Appl. No. 12/601,488, 2010/0166779, U.S. Pat. No. 8,425,902.
U.S. Appl. No. 14/397,244, 2015/0147763, U.S. Pat. No. 9,512,232.
U.S. Appl. No. 15/227,565, 2016/0333109, U.S. Pat. No. 10,053,512.
U.S. Appl. No. 16/037,759, 2018/0319891, pending.
U.S. Appl. No. 14/401,899, 2015/0132253, abandoned.
U.S. Appl. No. 15/909,577, 2018/0258180, abandoned.
U.S. Appl. No. 14/769,046, 2015/0374789, U.S. Pat. No. 9,770,487.
U.S. Appl. No. 15/684,168, 2018/0000900, U.S. Pat. No. 10,314,890.
U.S. Appl. No. 16/401,931, 2019/0298803, U.S. Pat. No. 10,946,069.
U.S. Appl. No. 17/066,232, 2021/0023177, pending.
U.S. Appl. No. 14/401,557, 2015/0157711, U.S. Pat. No. 9,433,675.
U.S. Appl. No. 15/231,185, 2016/0339101, U.S. Pat. No. 10,022,444.
U.S. Appl. No. 15/973,116, 2018/0326059, U.S. Pat. No. 10,813,996.
U.S. Appl. No. 17/008,316, 2020/0390887, pending.
U.S. Appl. No. 14/777,231, 2016/0008465, U.S. Pat. No. 10,137,195.
U.S. Appl. No. 16/158,187, 2019/0076525, U.S. Pat. No. 11,395,852.
U.S. Appl. No. 17/653,638, 2022/0184209, pending.
U.S. Appl. No. 15/565,848, 2018/0117174, U.S. Pat. No. 11,541,127.
U.S. Appl. No. 18/062,494, pending.
U.S. Appl. No. 15/565,306, 2018/0073077, U.S. Pat. No. 10,927,413.
U.S. Appl. No. 17/133,107, 2021/0324472, pending.
U.S. Appl. No. 14/442,445, 2016/0272711, U.S. Pat. No. 10,093,736.
U.S. Appl. No. 15/565,306, filed Oct. 9, 2017.
U.S. Appl. No. 17/133,107, filed Dec. 23, 2020.

Fig. 15

| Applicant's or agent's file reference 342-65 | International application No. |

INDICATIONS RELATING TO DEPOSITED MICROORGANISM OR OTHER BIOLOGICAL MATERIAL

(PCT Rule 13bis)

A. The indications made below relate to the deposited microorganism or other biological material referred to in the description on page 56, line 26.

B. IDENTIFICATION OF DEPOSIT    Further deposits are identified on an additional sheet [X]

Name of depositary institution
DSMZ-Deutsche Sammlung von Mikroorganismen und Zellkulturen GmbH Address of depositary institution (including postal code and country)
Mascheroder Weg 1b
38124 Braunschweig
DE

| Date of deposit | Accession Number |
|---|---|
| October 19, 2005 | DSM ACC2737 |

C. ADDITIONAL INDICATIONS (leave blank if not applicable)    This information is continued on an additional sheet [ ]

- Mouse (Mus musculus) myeloma P3X63Ag8U.1 fused with mouse (Mus musculus) splenocytes
- Hybridoma secreting antibody against human claudin-18A2

D. DESIGNATED STATES FOR WHICH INDICATIONS ARE MADE (if the indications are not for all designated States)

E. SEPARATE FURNISHING OF INDICATIONS (leave blank if not applicable)
The indications listed below will be submitted to the International Bureau later (specify the general nature of the indications e.g., "Accession Number of Deposit")

For receiving Office use only — [ ] This sheet was received with the international application    Authorized officer For International Bureau use only — [ ] This sheet was received by the International Bureau on:    Authorized officer Form PCT/RO/134 (July 1998; reprint January 2004)

Fig. 16

Additional Sheet for Biological Material

Identification of further deposits:
1) The Name and Address of depositary institution for the deposits (DSM ACC2738, DSM ACC2739, DSM ACC2740, DSM ACC2741, DSM ACC2742, DSM ACC2743, DSM ACC2745, DSM ACC2746, DSM ACC2747, DSM ACC2748) are:

DSMZ-Deutsche Sammlung von Mikroorganismen und Zellkulturen GmbH
   Mascheroder Weg 1b
   38124 Braunschweig DE 2) The Name and Address of depositary institution for the deposits (DSM ACC2808, DSM ACC2809, DSM ACC2810) are:

DSMZ-Deutsche Sammlung von Mikroorganismen und Zellkulturen GmbH
   Inhoffenstr. 7 B
   38124 Braunschweig DE

| Date of desposits | Accession Numbers | The indications made below relate to the deposited microorganism in the description on the following page(s) |
|---|---|---|
| October 19, 2005 | DSM ACC2738 | page 53, line 24 |
| October 19, 2005 | DSM ACC2739 | page 53, line 25 |
| October 19, 2005 | DSM ACC2740 | page 53, line 26 |
| October 19, 2005 | DSM ACC2741 | page 53, line 27 |
| October 19, 2005 | DSM ACC2742 | page 53, line 28 |
| October 19, 2005 | DSM ACC2743 | page 53, line 29 |
| November 17, 2005 | DSM ACC2745 | page 53, line 30 |
| November 17, 2005 | DSM ACC2746 | page 53, line 31 |
| November 17, 2005 | DSM ACC2747 | page 54, line 1 |
| November 17, 2005 | DSM ACC2748 | page 54, line 2 |
| October 26, 2006 | DSM ACC2808 | page 54, line 3 |
| October 26, 2006 | DSM ACC2809 | page 54, line 4 |
| October 26, 2006 | DSM ACC2810 | page 54, line 5 |

Additional Indications for all above mentioned deposits:
- Mouse (Mus musculus) myeloma P3X63Ag8U.1 fused with mouse (Mus musculus) splenocytes
- Hybridoma secreting antibody against human claudin-18A2

3) Depositor:
   All above mentioned depositions were made by:
   Ganymed Pharmaceuticals AG
   Freiligrathstraße 12
   55131 Mainz DE

SEQUENCE LISTING

```
Sequence total quantity: 78
SEQ ID NO: 1                    moltype = AA   length = 261
FEATURE                         Location/Qualifiers
source                          1..261
                                mol_type = protein
                                organism = Homo sapiens
SEQUENCE: 1
MAVTACQGLG FVVSLIGIAG IIAATCMDQW STQDLYNNPV TAVFNYQGLW RSCVRESSGF    60
TECRGYFTLL GLPAMLQAVR ALMIVGIVLG AIGLLVSIFA LKCIRIGSME DSAKANMTLT   120
SGIMFIVSGL CAIAGVSVFA NMLVTNFWMS TANMYTGMGG MVQTVQTRYT FGAALFVGWV   180
AGGLTLIGGV MMCIACRGLA PEETNYKAVS YHASGHSVAY KPGGFKASTG FGSNTKNKKI   240
YDGGARTEDE VQSYPSKHDY V                                            261

SEQ ID NO: 2                    moltype = AA   length = 261
FEATURE                         Location/Qualifiers
source                          1..261
                                mol_type = protein
                                organism = Homo sapiens
SEQUENCE: 2
MSTTTCQVVA FLLSILGLAG CIAATGMDMW STQDLYDNPV TSVFQYEGLW RSCVRQSSGF    60
TECRPYFTIL GLPAMLQAVR ALMIVGIVLG AIGLLVSIFA LKCIRIGSME DSAKANMTLT   120
SGIMFIVSGL CAIAGVSVFA NMLVTNFWMS TANMYTGMGG MVQTVQTRYT FGAALFVGWV   180
AGGLTLIGGV MMCIACRGLA PEETNYKAVS YHASGHSVAY KPGGFKASTG FGSNTKNKKI   240
YDGGARTEDE VQSYPSKHDY V                                            261

SEQ ID NO: 3                    moltype = AA   length = 10
FEATURE                         Location/Qualifiers
source                          1..10
                                mol_type = protein
                                organism = Homo sapiens
SEQUENCE: 3
DQWSTQDLYN                                                          10

SEQ ID NO: 4                    moltype = AA   length = 11
FEATURE                         Location/Qualifiers
source                          1..11
                                mol_type = protein
                                organism = Homo sapiens
SEQUENCE: 4
NNPVTAVFNY Q                                                        11

SEQ ID NO: 5                    moltype = AA   length = 14
FEATURE                         Location/Qualifiers
source                          1..14
                                mol_type = protein
                                organism = Homo sapiens
SEQUENCE: 5
STQDLYNNPV TAVF                                                     14

SEQ ID NO: 6                    moltype = AA   length = 13
FEATURE                         Location/Qualifiers
source                          1..13
                                mol_type = protein
                                organism = Homo sapiens
SEQUENCE: 6
TNFWMSTANM YTG                                                      13

SEQ ID NO: 7                    moltype = AA   length = 13
FEATURE                         Location/Qualifiers
source                          1..13
                                mol_type = protein
                                organism = Homo sapiens
SEQUENCE: 7
DSAKANMTLT SGI                                                      13

SEQ ID NO: 8                    moltype = AA   length = 55
FEATURE                         Location/Qualifiers
source                          1..55
                                mol_type = protein
                                organism = Homo sapiens
SEQUENCE: 8
MDQWSTQDLY NNPVTAVFNY QGLWRSCVRE SSGFTECRGY FTLLGLPAML QAVRA         55

SEQ ID NO: 9                    moltype = AA   length = 24
FEATURE                         Location/Qualifiers
source                          1..24
                                mol_type = protein
                                organism = Homo sapiens
```

```
SEQUENCE: 9
FALKCIRIGS MEDSAKANMT LTSG                                              24

SEQ ID NO: 10            moltype = AA   length = 40
FEATURE                  Location/Qualifiers
source                   1..40
                         mol_type = protein
                         organism = Homo sapiens
SEQUENCE: 10
ANMLVTNFWM STANMYTGMG GMVQTVQTRY TFGAALFVGW                              40

SEQ ID NO: 11            moltype = AA   length = 153
FEATURE                  Location/Qualifiers
source                   1..153
                         mol_type = protein
                         organism = Homo sapiens
SEQUENCE: 11
MDQWSTQDLY NNPVTAVFNY QGLWRSCVRE SSGFTECRGY FTLLGLPAML QAVRALMIVG        60
IVLGAIGLLV SIFALKCIRI GSMEDSAKAN MTLTSGIMFI VSGLCAIAGV SVFANMLVTN       120
FWMSTANMYT GMGGMVQTVQ TRYTFGAALF VGW                                   153

SEQ ID NO: 12            moltype = AA   length = 107
FEATURE                  Location/Qualifiers
REGION                   1..107
                         note = Description of artificial sequence: Translation of
                          PCR product
source                   1..107
                         mol_type = protein
                         organism = synthetic construct
SEQUENCE: 12
RTVAAPSVFI FPPSDEQLKS GTASVVCLLN NFYPREAKVQ WKVDNALQSG NSQESVTEQD        60
SKDSTYSLSS TLTLSKADYE KHKVYACEVT HQGLSSPVTK SFNRGEC                    107

SEQ ID NO: 13            moltype = AA   length = 326
FEATURE                  Location/Qualifiers
REGION                   1..326
                         note = Description of artificial sequence: Translation of
                          PCR product
source                   1..326
                         mol_type = protein
                         organism = synthetic construct
SEQUENCE: 13
GPSVFPLAPS SKSTSGGTAA LGCLVKDYFP EPVTVSWNSG ALTSGVHTFP AVLQSSGLYS        60
LSSVVTVPSS SLGTQTYICN VNHKPSNTKV DKKVEPKSCD KTHTCPPCPA PELLGGPSVF       120
LFPPKPKDTL MISRTPEVTC VVVDVSHEDP EVKFNWYVDG VEVHNAKTKP REEQYNSTYR       180
VVSVLTVLHQ DWLNGKEYKC KVSNKALPAP IEKTISKAKG QPREPQVYTL PPSRDELTKN       240
QVSLTCLVKG FYPSDIAVEW ESNGQPENNY KTTPPVLDSD GSFFLYSKLT VDKSRWQQGN       300
VFSCSVMHEA LHNHYTQKSL SLSPGK                                           326

SEQ ID NO: 14            moltype = AA   length = 466
FEATURE                  Location/Qualifiers
REGION                   1..466
                         note = Description of artificial sequence: chimeric
                          monoclonal antibody
source                   1..466
                         mol_type = protein
                         organism = synthetic construct
SEQUENCE: 14
MEWTWVFLFL LSVTAGVHSQ VQLQQSGAEL MKPGASVKIS CKATGYTFSS YWIEWVKQRP        60
GHGLEWIGEI LPGSGSTNYN EKFKGKATFT ADTSSNTAYM QLSSLTSEDS AVYYCARYDY       120
PWFAYWGQGT LVTVSAASTK GPSVFPLAPS SKSTSGGTAA LGCLVKDYFP EPVTVSWNSG       180
ALTSGVHTFP AVLQSSGLYS LSSVVTVPSS SLGTQTYICN VNHKPSNTKV DKKVEPKSCD       240
KTHTCPPCPA PELLGGPSVF LFPPKPKDTL MISRTPEVTC VVVDVSHEDP EVKFNWYVDG       300
VEVHNAKTKP REEQYNSTYR VVSVLTVLHQ DWLNGKEYKC KVSNKALPAP IEKTISKAKG       360
QPREPQVYTL PPSRDELTKN QVSLTCLVKG FYPSDIAVEW ESNGQPENNY KTTPPVLDSD       420
GSFFLYSKLT VDKSRWQQGN VFSCSVMHEA LHNHYTQKSL SLSPGK                     466

SEQ ID NO: 15            moltype = AA   length = 467
FEATURE                  Location/Qualifiers
REGION                   1..467
                         note = Description of artificial sequence: chimeric
                          monoclonal antibody
source                   1..467
                         mol_type = protein
                         organism = synthetic construct
SEQUENCE: 15
MDWLWNLLFL MAAAQSIQAQ IQLVQSGPEL KKPGETVKIS CKASGYTFTN YGMNWVKQAP        60
GKGLKWMGWI NTNTGEPTYA EEFKGRFAFS LETSASTAYL QINNLKNEDT ATYFCARLGF       120
GNAMDYWGQG TSVTVSSAST KGPSVFPLAP SSKSTSGGTA ALGCLVKDYF PEPVTVSWNS       180
```

```
GALTSGVHTF PAVLQSSGLY SLSSVVTVPS SSLGTQTYIC NVNHKPSNTK VDKKVEPKSC    240
DKTHTCPPCP APELLGGPSV FLFPPKPKDT LMISRTPEVT CVVVDVSHED PEVKFNWYVD    300
GVEVHNAKTK PREEQYNSTY RVVSVLTVLH QDWLNGKEYK CKVSNKALPA PIEKTISKAK    360
GQPREPQVYT LPPSRDELTK NQVSLTCLVK GFYPSDIAVE WESNGQPENN YKTTPPVLDS    420
DGSFFLYSKL TVDKSRWQQG NVFSCSVMHE ALHNHYTQKS LSLSPGK                  467

SEQ ID NO: 16           moltype = AA   length = 465
FEATURE                 Location/Qualifiers
REGION                  1..465
                        note = Description of artificial sequence: chimeric
                         monoclonal antibody
source                  1..465
                        mol_type = protein
                        organism = synthetic construct
SEQUENCE: 16
MEWIWIFLFI LSGTAGVHSQ VQLQQSGAEL ARPGASVKLS CKASGYTFTD YYINWVKQRT    60
GQGLEWIGEI YPGSGNTYYN EKFKGKATLT ADKSSSTAYM QLSSLTSEDS AVYFCARSYG    120
AFDYWGQGTT LTVSSASTKG PSVFPPLAPSS KSTSGGTAAL GCLVKDYFPE PVTVSWNSGA    180
LTSGVHTFPA VLQSSGLYSL SSVVTVPSSS LGTQTYICNV NHKPSNTKVD KKVEPKSCDK    240
THTCPPCPAP ELLGGPSVFL FPPKPKDTLM ISRTPEVTCV VVDVSHEDPE VKFNWYVDGV    300
EVHNAKTKPR EEQYNSTYRV VSVLTVLHQD WLNGKEYKCK VSNKALPAPI EKTISKAKGQ    360
PREPQVYTLP PSRDELTKNQ VSLTCLVKGF YPSDIAVEWE SNGQPENNYK TTPPVLDSDG    420
SFFLYSKLTV DKSRWQQGNV FSCSVMHEAL HNHYTQKSLS LSPGK                    465

SEQ ID NO: 17           moltype = AA   length = 467
FEATURE                 Location/Qualifiers
REGION                  1..467
                        note = Description of artificial sequence: chimeric
                         monoclonal antibody
source                  1..467
                        mol_type = protein
                        organism = synthetic construct
SEQUENCE: 17
MGWSCIILFL VATATGVHSQ VQLQQPGAEL VRPGASVKLS CKASGYTFTS YWINWVKQRP    60
GQGLEWIGNI YPGSDYTNYN QKFKDKATLT VDKSSSTAYM QLSSPTSEDS AVYYCTRSWR    120
GNSFDYWGQG TTLTVSSAST KGPSVFPLAP SSKSTSGGTA ALGCLVKDYF PEPVTVSWNS    180
GALTSGVHTF PAVLQSSGLY SLSSVVTVPS SSLGTQTYIC NVNHKPSNTK VDKKVEPKSC    240
DKTHTCPPCP APELLGGPSV FLFPPKPKDT LMISRTPEVT CVVVDVSHED PEVKFNWYVD    300
GVEVHNAKTK PREEQYNSTY RVVSVLTVLH QDWLNGKEYK CKVSNKALPA PIEKTISKAK    360
GQPREPQVYT LPPSRDELTK NQVSLTCLVK GFYPSDIAVE WESNGQPENN YKTTPPVLDS    420
DGSFFLYSKL TVDKSRWQQG NVFSCSVMHE ALHNHYTQKS LSLSPGK                  467

SEQ ID NO: 18           moltype = AA   length = 466
FEATURE                 Location/Qualifiers
REGION                  1..466
                        note = Description of artificial sequence: chimeric
                         monoclonal antibody
source                  1..466
                        mol_type = protein
                        organism = synthetic construct
SEQUENCE: 18
MEWRIFLFIL SGTAGVHSQV QLQQSGPELV KPGASVKMSC KASGYTFTDY VISWVKQRTG    60
QGLEWIGEIY PGSGSTYYNE KFKGKATLTA DKSSNTAYMQ LSSLTSEDSA VYFCARGVLL    120
RAMDYWGQGT SVTVSSASTK GPSVFPLAPS SKSTSGGTAA LGCLVKDYFP EPVTVSWNSG    180
ALTSGVHTFP AVLQSSGLYS LSSVVTVPSS SLGTQTYICN VNHKPSNTKV DKKVEPKSCD    240
KTHTCPPCPA PELLGGPSVF LFPPKPKDTL MISRTPEVTC VVVDVSHEDP EVKFNWYVDG    300
VEVHNAKTKP REEQYNSTYR VVSVLTVLHQ DWLNGKEYKC KVSNKALPAP IEKTISKAKG    360
QPREPQVYTL PPSRDELTKN QVSLTCLVKG FYPSDIAVEW ESNGQPENNY KTTPPVLDSD    420
GSFFLYSKLT VDKSRWQQGN VFSCSVMHEA LHNHYTQKSL SLSPGK                   466

SEQ ID NO: 19           moltype = AA   length = 469
FEATURE                 Location/Qualifiers
REGION                  1..469
                        note = Description of artificial sequence: chimeric
                         monoclonal antibody
source                  1..469
                        mol_type = protein
                        organism = synthetic construct
SEQUENCE: 19
MDWIWIMLHL LAAATGIQSQ VHLQQSGSEL RSPGSSVKLS CKDFDSEVFP FAYMSWIRQK    60
PGHGFEWIGD ILPSIGRTIY GEKFEDKATL DADTVSNTAY LELNSLTSED SAIYYCARGE    120
GYGAWFAYWG QGTLVTVSAA STKGPSVFPL APSSKSTSGG TAALGCLVKD YFPEPVTVSW    180
NSGALTSGVH TFPAVLQSSG LYSLSSVVTV PSSSLGTQTY ICNVNHKPSN TKVDKKVEPK    240
SCDKTHTCPP CPAPELLGGP SVFLFPPKPK DTLMISRTPE VTCVVVDVSH EDPEVKFNWY    300
VDGVEVHNAK TKPREEQYNS TYRVVSVLTV LHQDWLNGKE YKCKVSNKAL PAPIEKTISK    360
AKGQPREPQV YTLPPSRDEL TKNQVSLTCL VKGFYPSDIA VEWESNGQPE NNYKTTPPVL    420
DSDGSFFLYS KLTVDKSRWQ QGNVFSCSVM HEALHNHYTQ KSLSLSPGK                469

SEQ ID NO: 20           moltype = AA   length = 240
```

```
FEATURE                 Location/Qualifiers
REGION                  1..240
                        note = Description of artificial sequence: chimeric
                         monoclonal antibody
source                  1..240
                        mol_type = protein
                        organism = synthetic construct
SEQUENCE: 20
MESQTQVLMS LLFWVSGTCG DIVMTQSPSS LTVTAGEKVT MSCKSSQSLL NSGNQKNYLT   60
WYQQKPGQPP KLLIYWASTR ESGVPDRFTG SGSGTDFTLT ISSVQAEDLA VYYCQNDYSY  120
PLTFGAGTKL ELKRTVAAPS VFIFPPSDEQ LKSGTASVVC LLNNFYPREA KVQWKVDNAL  180
QSGNSQESVT EQDSKDSTYS LSSTLTLSKA DYEKHKVYAC EVTHQGLSSP VTKSFNRGEC  240

SEQ ID NO: 21           moltype = AA  length = 235
FEATURE                 Location/Qualifiers
REGION                  1..235
                        note = Description of artificial sequence: chimeric
                         monoclonal antibody
source                  1..235
                        mol_type = protein
                        organism = synthetic construct
SEQUENCE: 21
MHFQVQIFSF LLISASVIMS RGQIVLTQSP AIMSASPGEK VTITCSASSS VSYMHWFQQK   60
PGTSPKLWIY STSNLASGVP ARFSGSGSGT SYSLTISRME AEDAATYYCQ QRSSYPPTFG  120
GGTKLEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 22           moltype = AA  length = 234
FEATURE                 Location/Qualifiers
REGION                  1..234
                        note = Description of artificial sequence: chimeric
                         monoclonal antibody
source                  1..234
                        mol_type = protein
                        organism = synthetic construct
SEQUENCE: 22
MEFQTQVFVF VLLWLSGVDG DIVMTQSQKF MSTSVGDRVS ITCKASQNVR TAVAWYQQKP   60
GQSPKALIYL ASNRHTGVPD RFTGSGSGTD FTLTISNVQS EDLADYFCLQ HWNYPLTFGG  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 23           moltype = AA  length = 240
FEATURE                 Location/Qualifiers
REGION                  1..240
                        note = Description of artificial sequence: chimeric
                         monoclonal antibody
source                  1..240
                        mol_type = protein
                        organism = synthetic construct
SEQUENCE: 23
MDSQAQVLML LLLWVSGTCG DIVMSQSPSS LAVSVGEKVT MSCKSSQSLL YSSNQKNYLA   60
WYQQKPGQSP KLLIYWASTR ESGVPDRFTG SGSGTDFTLT ISSVKAEDLA VYYCQQYYSY  120
PLTFGAGTKL ELKRTVAAPS VFIFPPSDEQ LKSGTASVVC LLNNFYPREA KVQWKVDNAL  180
QSGNSQESVT EQDSKDSTYS LSSTLTLSKA DYEKHKVYAC EVTHQGLSSP VTKSFNRGEC  240

SEQ ID NO: 24           moltype = AA  length = 240
FEATURE                 Location/Qualifiers
REGION                  1..240
                        note = Description of artificial sequence: chimeric
                         monoclonal antibody
source                  1..240
                        mol_type = protein
                        organism = synthetic construct
SEQUENCE: 24
MESQTQVLMS LLFWVSGTCG DIVMTQSPSS LTVTAGEKVT MSCKSSQSLL NSGNQKNYLT   60
WYQQKPGQPP KLLIYWASTR ESGVPDRFTG SGSGTDFTLT ISSVQAEDLA VYYCQNDYSY  120
PFTFGSGTKL EIKRTVAAPS VFIFPPSDEQ LKSGTASVVC LLNNFYPREA KVQWKVDNAL  180
QSGNSQESVT EQDSKDSTYS LSSTLTLSKA DYEKHKVYAC EVTHQGLSSP VTKSFNRGEC  240

SEQ ID NO: 25           moltype = AA  length = 239
FEATURE                 Location/Qualifiers
REGION                  1..239
                        note = Description of artificial sequence: chimeric
                         monoclonal antibody
source                  1..239
                        mol_type = protein
                        organism = synthetic construct
SEQUENCE: 25
MDSQAQVLIL LLLWVSGTCG DIVMSQSPSS LAVSAGEKVT MSCKSSQSLL NSRTRKNYLA   60
```

```
WYQQKPGQSP KLLIYWASTR ESGVPDRFTG SGSGTDFTLT ISSVQAEDLA VYYCKQSYNL   120
YTFGGGTKLE IKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGEC    239

SEQ ID NO: 26            moltype = AA  length = 240
FEATURE                  Location/Qualifiers
REGION                   1..240
                         note = Description of artificial sequence: chimeric
                           monoclonal antibody
source                   1..240
                         mol_type = protein
                         organism = synthetic construct
SEQUENCE: 26
MDSQAQVLML LLLWVSGTCG DIVMSQSPSS LAVSVGEKVT MSCKSSQSLL YSSNQKNYLA    60
WYQQKPGQSP KLLIYWASTR ESGVPDRFTG SGSATDFTLT ISSVQAEDLA DYHCGQGYSY   120
PYTFGGGTKL EIKRTVAAPS VFIFPPSDEQ LKSGTASVVC LLNNFYPREA KVQWKVDNAL   180
QSGNSQESVT EQDSKDSTYS LSSTLTLSKA DYEKHKVYAC EVTHQGLSSP VTKSFNRGEC   240

SEQ ID NO: 27            moltype = AA  length = 240
FEATURE                  Location/Qualifiers
REGION                   1..240
                         note = Description of artificial sequence: chimeric
                           monoclonal antibody
source                   1..240
                         mol_type = protein
                         organism = synthetic construct
SEQUENCE: 27
MDSQAQVLML LLLWVSGTCG DIVMSQSPSS LAVSVGEKVT MSCKSSQSLL YSSNQKNYLA    60
WYQQKPGQSP KLLIYWASTR ESGVPDRFTG SGSGTDFTLT ISSVKAEDLA VYYCQQYYSY   120
PLTFGAGTKL ELKRTVAAPS VFIFPPSDEQ LKSGTASVVC LLNNFYPREA KVQWKVDNAL   180
QSGNSQESVT EQDSKDSTYS LSSTLTLSKA DYEKHKVYAC EVTHQGLSSP VTKSFNRGEC   240

SEQ ID NO: 28            moltype = AA  length = 234
FEATURE                  Location/Qualifiers
REGION                   1..234
                         note = Description of artificial sequence: chimeric
                           monoclonal antibody
source                   1..234
                         mol_type = protein
                         organism = synthetic construct
SEQUENCE: 28
MESQTLVFIS ILLWLYGADG NIVMTQSPKS MSMSVGERVT LTCKASENVV TYVSWYQQKP    60
EQSPKLLIYG ASNRYTGVPD RFTGSGSATD FTLTISSVKA EDLAVYYCQQ YYSYPLTFGA   120
GTKLELKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234

SEQ ID NO: 29            moltype = AA  length = 117
FEATURE                  Location/Qualifiers
REGION                   1..117
                         note = Description of artificial sequence: Translation of
                           PCR product
source                   1..117
                         mol_type = protein
                         organism = synthetic construct
SEQUENCE: 29
QVQLQQSGAE LMKPGASVKI SCKATGYTFS SYWIEWVKQR PGHGLEWIGE ILPGSGSTNY    60
NEKFKGKATF TADTSSNTAY MQLSSLTSED SAVYYCARYD YPWFAYWGQG TLVTVSA      117

SEQ ID NO: 30            moltype = AA  length = 118
FEATURE                  Location/Qualifiers
REGION                   1..118
                         note = Description of artificial sequence: Translation of
                           PCR product
source                   1..118
                         mol_type = protein
                         organism = synthetic construct
SEQUENCE: 30
QIQLVQSGPE LKKPGETVKI SCKASGYTFT NYGMNWVKQA PGKGLKWMGW INTNTGEPTY    60
AEEFKGRFAF SLETSASTAY LQINNLKNED TATYFCARLG FGNAMDYWGQ GTSVTVSS     118

SEQ ID NO: 31            moltype = AA  length = 116
FEATURE                  Location/Qualifiers
REGION                   1..116
                         note = Description of artificial sequence: Translation of
                           PCR product
source                   1..116
                         mol_type = protein
                         organism = synthetic construct
SEQUENCE: 31
```

```
QVQLQQSGAE LARPGASVKL SCKASGYTFT DYYINWVKQR TGQGLEWIGE IYPGSGNTYY    60
NEKFKGKATL TADKSSSTAY MQLSSLTSED SAVYFCARSY GAFDYWGQGT TLTVSS       116

SEQ ID NO: 32           moltype = AA  length = 118
FEATURE                 Location/Qualifiers
REGION                  1..118
                        note = Description of artificial sequence: Translation of
                        PCR product
source                  1..118
                        mol_type = protein
                        organism = synthetic construct
SEQUENCE: 32
QVQLQQPGAE LVRPGASVKL SCKASGYTFT SYWINWVKQR PGQGLEWIGN IYPSDSYTNY    60
NQKFKDKATL TVDKSSSTAY MQLSSPTSED SAVYYCTRSW RGNSFDYWGQ GTTLTVSS    118

SEQ ID NO: 33           moltype = AA  length = 118
FEATURE                 Location/Qualifiers
REGION                  1..118
                        note = Description of artificial sequence: Translation of
                        PCR product
source                  1..118
                        mol_type = protein
                        organism = synthetic construct
SEQUENCE: 33
QVQLQQSGPE LVKPGASVKM SCKASGYTFT DYVISWVKQR TGQGLEWIGE IYPGSGSTYY    60
NEKFKGKATL TADKSSNTAY MQLSSLTSED SAVYFCARGV LLRAMDYWGQ GTSVTVSS    118

SEQ ID NO: 34           moltype = AA  length = 120
FEATURE                 Location/Qualifiers
REGION                  1..120
                        note = Description of artificial sequence: Translation of
                        PCR product
source                  1..120
                        mol_type = protein
                        organism = synthetic construct
SEQUENCE: 34
QVHLQQSGSE LRSPGSSVKL SCKDFDSEVF PFAYMSWIRQ KPGHGFEWIG DILPSIGRTI    60
YGEKFEDKAT LDADTVSNTA YLELNSLTSE DSAIYYCARG EGYGAWFAYW GQGTLVTVSA  120

SEQ ID NO: 35           moltype = AA  length = 113
FEATURE                 Location/Qualifiers
REGION                  1..113
                        note = Description of artificial sequence: Translation of
                        PCR product
source                  1..113
                        mol_type = protein
                        organism = synthetic construct
SEQUENCE: 35
DIVMTQSPSS LTVTAGEKVT MSCKSSQSLL NSGNQKNYLT WYQQKPGQPP KLLIYWASTR    60
ESGVPDRFTG SGSGTDFTLT ISSVQAEDLA VYYCQNDYSY PLTFGAGTKL ELK         113

SEQ ID NO: 36           moltype = AA  length = 106
FEATURE                 Location/Qualifiers
REGION                  1..106
                        note = Description of artificial sequence: Translation of
                        PCR product
source                  1..106
                        mol_type = protein
                        organism = synthetic construct
SEQUENCE: 36
QIVLTQSPAI MSASPGEKVT ITCSASSSVS YMHWFQQKPG TSPKLWIYST SNLASGVPAR    60
FSGSGSGTSY SLTISRMEAE DAATYYCQQR SSYPPTFGGG TKLEIK                106

SEQ ID NO: 37           moltype = AA  length = 107
FEATURE                 Location/Qualifiers
REGION                  1..107
                        note = Description of artificial sequence: Translation of
                        PCR product
source                  1..107
                        mol_type = protein
                        organism = synthetic construct
SEQUENCE: 37
DIVMTQSQKF MSTSVGDRVS ITCKASQNVR TAVAWYQQKP GQSPKALIYL ASNRHTGVPD    60
RFTGSGSGTD FTLTISNVQS EDLADYFCLQ HWNYPLTFGG GTKLEIK                107

SEQ ID NO: 38           moltype = AA  length = 113
FEATURE                 Location/Qualifiers
REGION                  1..113
                        note = Description of artificial sequence: Translation of
```

```
                        PCR product
source                  1..113
                        mol_type = protein
                        organism = synthetic construct
SEQUENCE: 38
DIVMSQSPSS LAVSVGEKVT MSCKSSQSLL YSSNQKNYLA WYQQKPGQSP KLLIYWASTR    60
ESGVPDRFTG SGSGTDFTLT ISSVKAEDLA VYYCQQYYSY PLTFGAGTKL ELK          113

SEQ ID NO: 39           moltype = AA  length = 113
FEATURE                 Location/Qualifiers
REGION                  1..113
                        note = Description of artificial sequence: Translation of
                        PCR product
source                  1..113
                        mol_type = protein
                        organism = synthetic construct
SEQUENCE: 39
DIVMTQSPSS LTVTAGEKVT MSCKSSQSLL NSGNQKNYLT WYQQKPGQPP KLLIYWASTR    60
ESGVPDRFTG SGSGTDFTLT ISSVQAEDLA VYYCQNDYSY PFTFGSGTKL EIK          113

SEQ ID NO: 40           moltype = AA  length = 112
FEATURE                 Location/Qualifiers
REGION                  1..112
                        note = Description of artificial sequence: Translation of
                        PCR product
source                  1..112
                        mol_type = protein
                        organism = synthetic construct
SEQUENCE: 40
DIVMSQSPSS LAVSAGEKVT MSCKSSQSLL NSRTRKNYLA WYQQKPGQSP KLLIYWASTR    60
ESGVPDRFTG SGSGTDFTLT ISSVQAEDLA VYYCKQSYNL YTFGGGTKLE IK           112

SEQ ID NO: 41           moltype = AA  length = 113
FEATURE                 Location/Qualifiers
REGION                  1..113
                        note = Description of artificial sequence: Translation of
                        PCR product
source                  1..113
                        mol_type = protein
                        organism = synthetic construct
SEQUENCE: 41
DIVMSQSPSS LAVSVGEKVT MSCKSSQSLL YSSNQKNYLA WYQQKPGQSP KLLIYWASTR    60
ESGVPDRFTG SGSATDFTLT ISSVQAEDLA DYHCGQGYSY PYTFGGGTKL EIK          113

SEQ ID NO: 42           moltype = AA  length = 113
FEATURE                 Location/Qualifiers
REGION                  1..113
                        note = Description of artificial sequence: Translation of
                        PCR product
source                  1..113
                        mol_type = protein
                        organism = synthetic construct
SEQUENCE: 42
DIVMSQSPSS LAVSVGEKVT MSCKSSQSLL YSSNQKNYLA WYQQKPGQSP KLLIYWASTR    60
ESGVPDRFTG SGSGTDFTLT ISSVKAEDLA VYYCQQYYSY PLTFGAGTKL ELK          113

SEQ ID NO: 43           moltype = AA  length = 107
FEATURE                 Location/Qualifiers
REGION                  1..107
                        note = Description of artificial sequence: Translation of
                        PCR product
source                  1..107
                        mol_type = protein
                        organism = synthetic construct
SEQUENCE: 43
NIVMTQSPKS MSMSVGERVT LTCKASENVV TYVSWYQQKP EQSPKLLIYG ASNRYTGVPD    60
RFTGSGSATD FTLTISSVKA EDLAVYYCQQ YYSYPLTFGA GTKLELK                 107

SEQ ID NO: 44           moltype = AA  length = 15
FEATURE                 Location/Qualifiers
REGION                  1..15
                        note = Epitope
source                  1..15
                        mol_type = protein
                        organism = synthetic construct
SEQUENCE: 44
MDQWSTQDLY NNPVT                                                     15

SEQ ID NO: 45           moltype = AA  length = 15
```

```
FEATURE                   Location/Qualifiers
REGION                    1..15
                          note = Epitope
source                    1..15
                          mol_type = protein
                          organism = synthetic construct
SEQUENCE: 45
STQDLYNNPV TAVFN                                                         15

SEQ ID NO: 46             moltype = AA   length = 15
FEATURE                   Location/Qualifiers
REGION                    1..15
                          note = Epitope
source                    1..15
                          mol_type = protein
                          organism = synthetic construct
SEQUENCE: 46
LYNNPVTAVF NYQGL                                                         15

SEQ ID NO: 47             moltype = AA   length = 15
FEATURE                   Location/Qualifiers
REGION                    1..15
                          note = Epitope
source                    1..15
                          mol_type = protein
                          organism = synthetic construct
SEQUENCE: 47
PVTAVFNYQG LWRSC                                                         15

SEQ ID NO: 48             moltype = AA   length = 15
FEATURE                   Location/Qualifiers
REGION                    1..15
                          note = Epitope
source                    1..15
                          mol_type = protein
                          organism = synthetic construct
SEQUENCE: 48
VFNYQGLWRS CVRES                                                         15

SEQ ID NO: 49             moltype = AA   length = 15
FEATURE                   Location/Qualifiers
REGION                    1..15
                          note = Epitope
source                    1..15
                          mol_type = protein
                          organism = synthetic construct
SEQUENCE: 49
QGLWRSCVRE SSGFT                                                         15

SEQ ID NO: 50             moltype = AA   length = 15
FEATURE                   Location/Qualifiers
REGION                    1..15
                          note = Epitope
source                    1..15
                          mol_type = protein
                          organism = synthetic construct
SEQUENCE: 50
RSCVRESSGF TECRG                                                         15

SEQ ID NO: 51             moltype = AA   length = 467
FEATURE                   Location/Qualifiers
REGION                    1..467
                          note = chimeric monoclonal antibody
source                    1..467
                          mol_type = protein
                          organism = synthetic construct
SEQUENCE: 51
MGWSCIILFL VATATGVHSQ VQLQQPGAEL VRPGASVKLS CKASGYTFTS YWINWVKQRP        60
GQGLEWIGNI YPSDSYTNYN QKFKDKATLT VDKSSSTAYM QLSSPTSEDS AVYYCTRSWR       120
GNSFDYWGQG TTLTVSSAST KGPSVFPLAP SSKSTSGGTA ALGCLVKDYF PEPVTVSWNS       180
GALTSGVHTF PAVLQSSGLY SLSSVVTVPS SSLGTQTYIC NVNHKPSNTK VDKRVEPKSC       240
DKTHTCPPCP APELLGGPSV FLFPPKPKDT LMISRTPEVT CVVVDVSHED PEVKFNWYVD       300
GVEVHNAKTK PREEQYNSTY RVVSVLTVLH QDWLNGKEYK CKVSNKALPA PIEKTISKAK       360
GQPREPQVYT LPPSREEMTK NQVSLTCLVK GFYPSDIAVE WESNGQPENN YKTTPPVLDS       420
DGSFFLYSKL TVDKSRWQQG NVFSCSVMHE ALHNHYTQKS LSLSPGK                    467

SEQ ID NO: 52             moltype = DNA   length = 51
FEATURE                   Location/Qualifiers
misc_feature              26
```

```
                        note = n may be C or T
source                  1..51
                        mol_type = other DNA
                        organism = Homo sapiens
SEQUENCE: 52
tgggatggag aaggtgggat ccaaanggga gaatttctgg gattttccat t          51

SEQ ID NO: 53           moltype = DNA  length = 51
FEATURE                 Location/Qualifiers
misc_feature            26
                        note = n may be A or G
source                  1..51
                        mol_type = other DNA
                        organism = Homo sapiens
SEQUENCE: 53
cccctaaacc cgcaacagtt gttacnggtt ctggtcatgc aagctctacc c          51

SEQ ID NO: 54           moltype = DNA  length = 51
FEATURE                 Location/Qualifiers
misc_feature            26
                        note = n may be A or G
source                  1..51
                        mol_type = other DNA
                        organism = Homo sapiens
SEQUENCE: 54
caacactact aaggcttctt tgggangggg aagtagggat aggtaagagg a          51

SEQ ID NO: 55           moltype = DNA  length = 51
FEATURE                 Location/Qualifiers
misc_feature            26
                        note = n may be A or G
source                  1..51
                        mol_type = other DNA
                        organism = Homo sapiens
SEQUENCE: 55
aattccacca gcacagccac tcactntgtg ctcatctcac tcctccagca g          51

SEQ ID NO: 56           moltype = DNA  length = 51
FEATURE                 Location/Qualifiers
misc_feature            26
                        note = n may be A or G
source                  1..51
                        mol_type = other DNA
                        organism = Homo sapiens
SEQUENCE: 56
aggtccagag ccagtgttct tgttcnacct gaaagtaatg gctctgggtt g          51

SEQ ID NO: 57           moltype = DNA  length = 51
FEATURE                 Location/Qualifiers
misc_feature            26
                        note = n may be A or G
source                  1..51
                        mol_type = other DNA
                        organism = Homo sapiens
SEQUENCE: 57
ctttcagccc caatccaagg gttgtngctg gaactttcca tcagttcttc c          51

SEQ ID NO: 58           moltype = DNA  length = 51
FEATURE                 Location/Qualifiers
misc_feature            26
                        note = n may be A or C
source                  1..51
                        mol_type = other DNA
                        organism = Homo sapiens
SEQUENCE: 58
ctagcaactc caggctagag ggtcancgcg tctatgcgag gccgggtggg c          51

SEQ ID NO: 59           moltype = DNA  length = 51
FEATURE                 Location/Qualifiers
misc_feature            26
                        note = n may be C or T
source                  1..51
                        mol_type = other DNA
                        organism = Homo sapiens
SEQUENCE: 59
atcccgtact gaagttcgtg cgcaangtgc cctgggaatt tggcgacgta a          51

SEQ ID NO: 60           moltype = DNA  length = 51
FEATURE                 Location/Qualifiers
```

```
misc_feature          26
                      note = n may be G or T
source                1..51
                      mol_type = other DNA
                      organism = Homo sapiens
SEQUENCE: 60
cggctcctac ttctgcaggg ggcttnttgg gagtaaaaat gtgtcttcag a              51

SEQ ID NO: 61         moltype = DNA  length = 2429
FEATURE               Location/Qualifiers
source                1..2429
                      mol_type = genomic DNA
                      organism = Homo sapiens
SEQUENCE: 61
ctctttctta agcttgtctc ttaaaaccca ctggacgttg cacagtgct gggatgacta      60
tggagaccca aatgtctcag aatgtatgtc ccagaaacct gtggctgctt caaccattga    120
cagttttgct gctgctggct tctgcagaca gtcaagctgc agctccccca aaggctgtgc    180
tgaaacttga gcccccgtgg atcaacgtgc tccaggagga ctctgtgact ctgacatgcc    240
aggggggctcg cagccctgag agcgactcca ttcagtggtt ccacaatggg aatctccattc   300
ccacccacac gcagcccagc tacaggttca aggccaacaa caatgacagc ggggagtaca    360
cgtgccagac tggccagacc agcctcagcg acccctgtgca tctgactgtg ctttccgaat    420
ggctgtgct ccagacccct cacctggagt tccaggaggg agaaaccatc atgctgaggt      480
gccacagctg gaaggacaag cctctggtca aggtcacatt cttccagaat ggaaaatccc    540
agaaattctc ccatttggat cccaccttct ccatcccaca agcaaccac agtcacagtg      600
gtgattacca ctgcacagga acataggct acacgctgtt ctcatccaag cctgtgacca    660
tcactgtcca agtgcccagc atgggcagct cttcaccaat ggggatcatt gtggctgtgg   720
tcattgcgac tgctgtagca gccattgttg ctgctgtagt ggccttgatc tactgcagga    780
aaaagcggat ttcagccaat tccactgatc ctgtgaaggc tgcccaattt gagccacctg   840
gacgtcaaat gattgccatc agaaagagac aacttgaaga aaccaacaat gactatgaaa    900
cagctgacgg cggctacatg actctgaacc ccagggcacc tactgacgat gataaaaaca    960
tctacctgac tcttcctccc aacgaccatg tcaacagtaa taactaagaa gtaacgttat    1020
gccatgtggt catactctca gcttgctgag tggatgacaa aaagaggga attgttaaag     1080
gaaaattaa atggagactg gaaaaatcct gagcaaacaa aaccacctgg cccttagaaa    1140
tagctttaac tttgcttaaa ctacaaacac aagcaaaact ccgggggtc atactacata    1200
caagcataaa caaacttaa cttggatcat ttctggtaaa tgcttatgtt agaaataaga    1260
caacccagc caatcacaag cagcctacta acatataatt aggtgactag ggactttcta    1320
agaagatacc taccccaaa aaacaattat gtaattgaaa accaaccgat tgcctttatt     1380
ttgcttccac attttcccaa taaatacttg cctgtgacat tttgccactg gaacactaaa   1440
cttcatgaat tgcgcctcag atttttcctt taacatcatt ttttttttg acagagtcat    1500
aatctgttac ccaggctgga gtgcagtggt gctatcttgg ctcactgcaa acccgcctcc    1560
caggtttaag cgattctcat gcctcagcct cccagtagct gggattagag gcatgtgcca    1620
tcatacccag ctaatttttg tatttttat ttttttttt tagtagagac agggtttcgc     1680
aatgttggcc aggccgatct cgaacttctg gcctctaagtg atctgcccgc tcggcctcc    1740
caaagtgctg ggatgaccag catcagcccc aatgtccagc ctctttaaca tcttctttcc    1800
tatgccctct ctgtggatcc ctactgctgg tttctgcctt ctccatgctg agaacaaaat    1860
cacctattca ctgcttatgc agtcggaagc tccagaagaa caaagagccc aattaccaga    1920
accacattaa gtctccattg tttttgcttg ggatttgaga agagaattag agaggtgagg    1980
atctggtatt tcctggacta aattcccctt ggggaagacg aagggatgct gcagttccaa    2040
aagagaagga ctcttccaga gtcatctacc tgagtcccaa agctcccctg cctgaaagcc    2100
acagacaata tggtcccaaa tgactgactg caccttctgt gcctcagccg ttcttgacat    2160
caagaatctt ctgttccaca tccacacagc caatacaact agtcaaacca ctgttattaa    2220
cagatgtagc aacatgagaa acgcttatgt tacaggttac atgagagcaa tcatgtaagt    2280
ctatatgact tcagaaatgt taaaatagac taacctctaa caacaaatta aaagtgattg    2340
tttcaaggtg atgcaattat tgatgaccta ttttattttt ctataatgat catatattac    2400
ctttgtaata aacattata accaaaaca                                        2429

SEQ ID NO: 62         moltype = AA  length = 317
FEATURE               Location/Qualifiers
source                1..317
                      mol_type = protein
                      organism = Homo sapiens
SEQUENCE: 62
MTMETQMSQN VCPRNLWLLQ PLTVLLLLAS ADSQAAAPPK AVLKLEPPWI NVLQEDSVTL     60
TCQGARSPES DSIQWFHNGN LIPTHTQPSY RFKANNNDSG EYTCQTGQTS LSDPVHLTVL    120
SEWLVLQTPH LEFQEGETIM LRCHSWKDKP LVKVTFFQNG KSQKFSHLDP TFSIPQANHS    180
HSGDYHCTGN IGYTLFSSKP VTITVQVPSM GSSSPMGIIV AVVIATAVAA IVAAVVALIY    240
CRKKRISANS TDPVKAAQFE PPGRQMIAIR KRQLEETNND YETADGGYMT LNPRAPTDDD    300
KNIYLTLPPN DHVNSNN                                                    317

SEQ ID NO: 63         moltype = DNA  length = 1193
FEATURE               Location/Qualifiers
source                1..1193
                      mol_type = genomic DNA
                      organism = Homo sapiens
SEQUENCE: 63
cgctccacct tcaagcagc cagcgcctgc ctgaatctgt tctgccccct ccccacccat      60
ttcaccacca ccatgacacc gggcacccag tctcctttct cctgctgct gctcctcaca    120
gtgcttacag ctaccacagc ccctaaaccc gcaacagttg ttacgggttc tggtcatgca    180
agctctaccc caggtggaga aaaggagact tcggctaccc agaagagttc agtgcccagc    240
```

```
tctactgaga agaatgcttt taattcctct ctggaagatc ccagcaccga ctactaccaa    300
gagctgcaga gagacatttc tgaaatgttt ttgcagattt ataaacaagg gggttttctg    360
ggcctctcca atattaagtt caggccagga tctgtggtgg tacaattgac tctgccttc     420
cgagaaggta ccatcaatgt ccacgacgtg gagacacagt tcaatcagta taaaacggaa    480
gcagcctctc gatataacct gacgatctca gacgtcagtg tgagtgatgt gccatttcct    540
ttctctgccc agtctggggc tggggtgcca ggctggggca tcgcgctgct ggtgctggtc    600
tgtgttctgg ttgcgctggc cattgtctat ctcattgcct ggctgtctg tcagtgccgc     660
cgaaagaact acgggcagct ggacatcttt ccagcccggg ataccacca tcctatgagc     720
gagtaccca cctaccacac ccatgggcgc tatgtgcccc ctagcagtac cgatcgtagc     780
ccctatgaga aggtttctgc aggtaatggt ggcagcagcc tctcttacac aaacccagca    840
gtggcagcca cttctgccaa cttgtagggg cacgtcgccc gctgagctga gtggccagcc    900
agtgccattc cactccactc aggttcttca gggccagagc ccctgcaccc tgtttgggct    960
ggtgagctgg gagttcaggt gggctgctca cagcctcctt cagaggcccc accaatttct   1020
cggacacttc tcagtgtgtg gaagctcatg tgggccccatg agggctcatg cctgggaagt   1080
gttgtggtgg gggctcccag gaggactggc ccagagagcc ctgagatagc ggggatcctg   1140
aactggactg aataaaacgt ggtctcccac tgcgccaaaa aaaaaaaaaa aaa          1193

SEQ ID NO: 64           moltype = AA   length = 264
FEATURE                 Location/Qualifiers
source                  1..264
                        mol_type = protein
                        organism = Homo sapiens
SEQUENCE: 64
MTPGTQSPFF LLLLLTVLTA TTAPKPATVV TGSGHASSTP GGEKETSATQ RSSVPSSTEK     60
NAFNSSLEDP STDYYQELQR DISEMFLQIY KQGGFLGLSN IKFRPGSVVV QLTLAFREGT    120
INVHDVETQF NQYKTEAASR YNLTISDVSV SDVPFPFSAQ SGAGVPGWGI ALLVLVCVLV    180
ALAIVYLIAL AVCQCRRKNY GQLDIFPARD TYHPMSEYPT YHTHGRYVPP SSTDRSPYEK    240
VSAGNGGSSL SYTNPAVAAT SANL                                           264

SEQ ID NO: 65           moltype = DNA   length = 1629
FEATURE                 Location/Qualifiers
source                  1..1629
                        mol_type = genomic DNA
                        organism = Homo sapiens
SEQUENCE: 65
acacatcagg ggcttgctct tgcaaaacca aaccacaaga cagacttgca aaagaaggca     60
tgcacagctc agcactgctc tgttgcctgg tcctcctgac tggggtgagg gccagcccag    120
gccagggcac ccagtctgag aacagctgca cccacttccc aggcaacctg cctaacatgc    180
ttcgagatct ccgagatgcc ttcagcagag tgaagactt ctttcaaatg aaggatcagc     240
tggacaactt gttgttaaag gagtccttgc tggaggactt taaggggttac ctgggttgcc    300
aagccttgtc tgagatgatc cagttttacc tggaggaggt gatgccccaa gctgagaacc    360
aagacccaga catcaaggcg catgtgaact ccctggggga gaacctgaag accctcaggc    420
tgaggctacg gcgctgtcat cgatttcttc cctgtgaaaa caagagcaag gccatgaagc    480
aggtgaagaa tgcctttaat aagctccaag agaaaggcat ctacaaagcc atgagtgagt    540
ttgacatctt catcaactac atagaagcct acatgacaat gaagatacga aactgagaca    600
tcagggtggc gactctatag actctaggac ataaattaga ggtctccaaa atcggatctg    660
gggctctggg atagctgacc cagccccttg agaaaccttat tgtacctct cttatagaat     720
atttattacc tctgataccct caaccccat ttctatttat ttactgagct tctctgtgaa     780
cgatttagaa agaagcccaa tattataatt tttttcaata tttattattt tcacctgttt     840
ttaagctgtt tccatagggt gacacactat ggtatttgag tgttttaaga taaattataa     900
gttacataag gggaggaaaa aaatgttctt tggggagcca acagaagctt ccattccaag     960
cctgaccacg cttttctagct gttgagctgt ttccctgac ctccctctaa ttttatcttgt    1020
ctctgggctt ggggcttcct aactgctaca aatactctta ggaagagaaa ccagggagcc    1080
cctttgatga ttaattcacc ttccagtgtc tcggaggat tccctaacc tcattcccca      1140
accacttcat tcttgaaagc tgtggccagc ttgttattta taacaaccta aatttggttc    1200
taggccgggc gcggtggctc acgcctgtaa tcccagcact tgggaggct gaggcgggtg     1260
gatcacttga ggtcaggagt tcctaaccag cctggtcaac atggtgaaac cccgtctcta    1320
ctaaaaatac aaaaattagc cgggcatggt ggcgcgcacc tgtaatccca gctacttggg    1380
aggctgaggc aagagaattg cttgaaccca ggagatggaa gttgcagtga gctgatatca    1440
tgccctgta ctccagcctg ggtgacagag caagactctg tctcaaaaaa taaaaataaa     1500
aataaatttg gttctaatag aactcagttt taactagaat ttattcaatt cctctgggaa    1560
tgttacattg tttgtctgtc ttcatagcag attttaattt tgaataaata aatgtatctt    1620
attcacatc                                                           1629

SEQ ID NO: 66           moltype = AA   length = 178
FEATURE                 Location/Qualifiers
source                  1..178
                        mol_type = protein
                        organism = Homo sapiens
SEQUENCE: 66
MHSSALLCCL VLLTGVRASP GQGTQSENSC THFPGNLPNM LRDLRDAFSR VKTFFQMKDQ     60
LDNLLLKESL LEDFKGYLGC QALSEMIQFY LEEVMPQAEN QDPDIKAHVN SLGENLKTLR    120
LRLRRCHRFL PCENKSKAVE QVKNAFNKLQ EKGIYKAMSE FDIFINYIEA YMTMKIRN      178

SEQ ID NO: 67           moltype = DNA   length = 4324
FEATURE                 Location/Qualifiers
source                  1..4324
                        mol_type = genomic DNA
                        organism = Homo sapiens
```

```
SEQUENCE: 67
cggcggcggc gagagcagag gacgagccgg gacgcggcgc cgcggcacca gggcgcgcag   60
ccgggccggc ccgaccccac cggccatacg gtggagccat cgaagccccc acccacaggc  120
tgacagaggc accgttcacc agagggctca acaccgggac ctatgtttaa gttttaactc  180
tcgcctccaa agaccacgat aattccttcc ccaaagccca gcagccccca agccccgcgc  240
agcccccagcc tgcctcccgg cgcccagatg cccgccatgc cctccagcgg ccccgggggac  300
accagcagct ctgctgcgga gcgggaggag gaccgaaagg acggagagga gcaggaggag  360
ccgcgtggca aggaggagcg ccaagagccc agcaccacgg cacggaaggt ggggcggcct  420
gggaggaagc gcaagcaccc cccggtggaa agcggtgaca cgccaaagga ccctgcggtg  480
atctccaagt ccccatccat ggcccaggac tcaggcgcct caggctatt acccaatggg  540
gacttggaga agcggagtga gccccagcca gaggagggga gccctgctgg ggggcagaag  600
ggcgggggccc cagcagaggg agagggtgca gctgagaccc tgcctgaagc ctcaagagca  660
gtggaaaatg gctgctgcac ccccaaggag ggccgaggag cccctgcaga agcgggcaaa  720
gaacagaagg agaccaacat cgaatccatg aaaatggagg gctcccgggg ccggctgcgg  780
ggtggcttgg gctgggagtc cagcctccgt cagcggccca tgccgaggct caccttccag  840
gcgggggacc cctactacat cagcaagcgc aagcgggacg agtggctggc acgctggaaa  900
agggaggctg agaagaaagc caaggtcatt gcaggaatga atgctgtgga agaaaaccag  960
gggcccgggg agtctcagaa ggtggaggag gccagccctc ctgctgtgca gcagcccact 1020
gaccccgcat cccccactgt ggctaccacg cctgagcccg tggggtccga tgctggggac 1080
aagaatgcca ccaaagcagg cgatgacgag ccagagtacg aggacggccg gggctttggc 1140
attggggagc tggtgtgggg gaaactgcgg ggcttctcct ggtggccagg ccgcattgtg 1200
tcttggtgga tgacgggccg gagccgagca gctgaaggca cccgctgggt catgtggttc 1260
ggagacggca aattctcagt ggtgtgtgtt gagaagctga tgccgctgag ctcgttttgc 1320
agtgcgttcc accaggccac gtacaacaag cagcccatgt accgcaaagc catctacgag 1380
gtcctgcagg tggccagcag ccgcgcgggg aagctgttcc cggtgtgcca cgacagcgat 1440
gagagtgaca ctgccaaggc cgtggaggtg cagaacaccc catgattga atgggcctg 1500
ggggcttcc agccttctgg ccctaaggc ctggagccac cagaagaaga gaagaatccc 1560
tacaaagaag tgtacacgga catgtgggtg aacctgagg cagctgccta cgcaccacct 1620
ccaccagcca aaaagcccg gaagagcaca gcggagaagc ccaaggtcaa ggagattatt 1680
gatgagcca aagagagcg gctggtgtac gaggtgcgac agaagtgccg gaacattgag 1740
gacatctgca tctcctgtgg gagcctcaat gttaccctgg aacaccccct cttcgttgga 1800
ggaatgtgcc aaaactgcaa gaactgcttt ctggagtgtg cgtaccagta cgacgacgac 1860
ggctaccagt cctactgcac catctgctgt gggggccgtg aggtgctcat gtgcggaaac 1920
aacaactgct gcaggtgctt ttgcgtggag tgtgtggacc tcttggtggg gccgggggct 1980
gcccaggcag ccattaagga agaccccgg aactgctaca tgtgcgggca caagggtacc 2040
tacgggctgc tgcggcggcg agaggactgg ccctccccgg ctcagatgtt cttcgctaat 2100
aaccacgacc aggaatttga cctccaaag gtttacccac ctgtcccagc tgagaagagg 2160
aagcccatcc gggtgctgtc tctctttgat ggaatcgcta cagggctcct ggtgctgaag 2220
gacttggga ttcaggtgga ccgctacatt gcctcggaag tgtgtgagga ctccatccag 2280
gtgggcatgg tgcggcacca ggggaagatc atgtacgtcg gggacgtccg cagcgtcaca 2340
cagaagcata tccaggagtg gggccattc gatctggtga ttgggggcag tccctgcaat 2400
gacctctcca tcgtcaaccc tgctcgcaag ggcctctacg agggcactgg ccggctcttc 2460
tttgagttct accgcctcct gcatgatgcg cggcccaagg aggagatga tcgccccttc 2520
ttctggctct tgagaatgt ggtggccatg ggcgttagtg acaagaggga catctcgcga 2580
ttttctcgagt ccaaccctgt gatgattgat gccaaagaag tgtcagctgc cacagggcc 2640
cgctacttct ggggtaacct tcccggtatg aacaggccgt tggcatccac ctgtgaatgat 2700
aagctggagc tgcaggagtg tctggagcat ggcaggatca ccaagttcag caaagtgagg 2760
accattacta cgaggtcaaa ctccataaag cagggcaaag accagcattt tcctgtcttc 2820
atgaatgaga aagaggacat cttatggtgc actgaaatgg aaagggtatt tggtttccca 2880
gtccactata ctgacgtctc caacatgagc cgcttggcga ggcagagact gctgggccgg 2940
tcatggacg tgcagtcat ccgccacctc ttcgctccgc tgaaggagta ttttgcggg 3000
gtgtaaggga catgggggca aactgaggta gcgacacaaa gttaaacaaa caaacaaaaa 3060
acacaaaaca taataaaaca ccaagaacat gaggatggag agaagtatca gcacccagaa 3120
gagaaaaagg aatttaaaac aaaaaccaca gaggcgaaa taccggaggg cttttgcctg 3180
cgaaaagggt tggacatcat ctcctgattt tcaatgtta ttcttcagtc ctatttaaaa 3240
acaaaaccaa gctcccttcc cttcctcccc cttcccttt tttcggtca gacctttat 3300
tttctactct tttcagaggg gttttctgtt tgtttgggtt tgtttcttg ctgtgactga 3360
aacaagaagg ttattgcagc aaaaatcagt aacaaaaaat agtaacaata ccttgcagag 3420
gaaaggtggg agagaggaaa aaaggaaatt ctatagaaat ctatatattg ggttgttttt 3480
ttttttgttt tttgtttttt tttttgggt ttttttttt actatatatc ttttttttgt 3540
tgtctctagc ctgatcagat aggagcacaa gcagggacg gaaagagaga gacactcagg 3600
cggcagcatt cctcccagc cactgagctg tcgtgccagc accatcctg gtcacgcaaa 3660
acagaaccca gttagcagca gggagacgag aacaccacac aagacatttt tctacagtat 3720
ttcaggtgcc taccacacag gaaaccttga agaaaatcag tttctagaag ccgctgttac 3780
ctcttgttta cagtttatat atatatgata gatatgagat atatatataa aaggtactgt 3840
taactactgt acaacccgac ttcataatgg tgctttcaaa cagcgagatg agtaaaaaca 3900
tcagcttcca cgttgccttc tgcgcaaagg gtttcaccaa ggatgagaa agggagacag 3960
cttgcagatg gcgcgttctc acggtgggct cttcccttg gtttgtaacg aagtgaagga 4020
ggagaacttg ggagccaggt tctccctgcc aaaaagggg ctagatggg tggtcgggcc 4080
cgtggacagc tgagagtggg attcatccag actcatgcaa taaccctttg attgttttct 4140
aaaaggagac tccctcggca agatggcaga gggtacggag tcttcaggcc cagttctca 4200
ctttagccaa ttcgagggct ccttgtggtg ggatcagaac taatccagag tgtgggaaag 4260
tgacagtcaa accccaccct ggagcaaata aaaaacata caaacgtac tggtgcttc 4320
ctgt                                                              4324

SEQ ID NO: 68         moltype = AA    length = 912
FEATURE               Location/Qualifiers
source                1..912
                      mol_type = protein
```

```
                        organism = Homo sapiens
SEQUENCE: 68
MPAMPSSGPG DTSSSAAERE EDRKDGEEQE EPRGKEERQE PSTTARKVGR PGRKRKHPPV    60
ESGDTPKDPA VISKSPSMAQ DSGASELLPN GDLEKRSEPQ PEEGSPAGGQ KGGAPAEGEG   120
AAETLPEASR AVENGCCTPK EGRGAPAEAG KEQKETNIES MKMEGSRGRL RGGLGWESSL   180
RQRPMPRLTF QAGDPYYISK RKRDEWLARW KREAEKKAKV IAGMNAVEEN QGPGESQKVE   240
EASPPAVQQP TDPASPTVAT TPEPVGSDAG DKNATKAGDD EPEYEDGRGF GIGELVWGKL   300
RGFSWWPGRI VSWWMTGRSR AAEGTRWVMW FGDGKFSVVC VEKLMPLSSF CSAFHQATYN   360
KQPMYRKAIY EVLQVASSRA GKLFPVCHDS DESDTAKAVE VQNKPMIEWA LGGFQPSGPK   420
GLEPPEEEKN PYKEVYTDMW VEPEAAAYAP PPPAKKPRKS TAEKPKVKEI IDERTRERLV   480
YEVRQKCRNI EDICISCGSL NVTLEHPLFV GGMCQNCKNC FLECAYQYDD DGYQSYCTIC   540
CGGREVLMCG NNNCCRCFCV ECVDLLVGPG AAQAAIKEDP WNCYMCGHKG TYGLLRRRED   600
WPSRLQMFFA NNHDQEFDPP KVYPPVPAEK RKPIRVLSLF DGIATGLLVL KDLGIQVDRY   660
IASEVCEDSI TVGMVRHQGK IMYVGDVRSV TQKHIQEWGP FDLVIGGSPC NDLSIVNPAR   720
KGLYEGTGRL FFEFYRLLHD ARPKEGDDRP FFWLFENVVA MGVSDKRDIS RFLESNPVMI   780
DAKEVSAAHR ARYFWGNLPG MNRPLASTVN DKLELQECLE HGRIAKFSKV RTITTRSNSI   840
KQGKDQHFPV FMNEKEDILW CTEMERVFGF PVHYTDVSNM SRLARQRLLG RSWSVPVIRH   900
LFAPLKEYFA CV                                                       912

SEQ ID NO: 69           moltype = DNA   length = 8789
FEATURE                 Location/Qualifiers
source                  1..8789
                        mol_type = genomic DNA
                        organism = Homo sapiens
SEQUENCE: 69
atgctcagtg gcttctcgac aagttggcag caacaacacg gccctggtcg tcgtcgccgc     60
tgcggtaacg gagcggtttg ggtggcggag cctgcgttcg cgccttcccg ctctcctcgg    120
gaggcccttc ctgctctccc ctaggctccg cggccgccca ggggtggga gcgggtgagg    180
ggagccaggc gcccagcgag agaggccccc cgccgcaggg cggcccggga gctcgaggcg    240
gtccggcccg cgcgggcagc ggcgcggcgc tgaggagggg cggcgcaggg gggacgcctc    300
ggggcgggg ccgaggagct ctccggccg ccggggaaaa ctacgggccc ggtgcgtccg    360
cggaccagca gcgcgggaga gcggactccc ctcgccaccg cccgagccca ggttatcctg    420
aatacatgtc taacaatttt ccttgcaacg ttagctgttg ttttcactg tttccaaagg    480
atcaaaattg cttcagaaat tggagacata tttgatttaa aaggaaaaac ttgaacaaat    540
ggacaatatg tctattacga atacaccaac aagtaatgat gcctgtctga gcattgtgca    600
tagtttgatg tgccatagac aaggtggaga gagtgaaaca tttgcaaaaa gagcaattga    660
aagtttggta aagaagctga aggagaaaaa agatgaattg gattcttaa taacagctat    720
aactacaaat ggagctcatc ctagtaaatg tgttaccata cagagaacat tggatgggag    780
gcttcaggtg gctggtcgga aaggattcc tcatgtgatc tatgcccgtc tctgaggtg    840
gcctgatctt cacaaaaatg aactaaaaca tgttaaatat tgtcagtatg cgttgactt    900
aaaatgtgat agtgtctgtg tgaatccata tcactacgaa cgagttgtat cacctggaat    960
tgatctctca ggattaacac tgcagagtaa tgctccatca agtatgatgg tgaaggatga   1020
atatgtgcat gactttgagg acagccatc gttgtccact gaaggacatt caattcaaac   1080
catccagcat ccaccaagta atcgtgcatc gacagagaca tacagcaccc cagctctgtt   1140
agccccatct gagtctaatg ctaccagcac tgccaacttt cccaacattc ctgtggcttc   1200
cacaagtcag cctgccagta tactggggg cagcccatag taaggactgt tgcagatagc   1260
atcagggcct cagccaggac agcagcagaa tggatttact ggtcagccag ctacttacca   1320
tcataacagc actaccacct ggactggaag taggactgca ccatacacac taatttgcc   1380
tcaccaccaa aacggccatc ttcagcacca cccgcctatg ccgcccatc ccggacatta   1440
ctggcctgtt cacaatgagc ttgcattcca gcctcccatt ccaatcatc ctgctcctga   1500
gtattggtgt tccattgctt actttgaaat ggatgttcag gtaggagaga catttaaggt   1560
tccttcaagc tgcccctatg ttactgttga tggatacgtg gacccttctg gaggagatca   1620
cttttgtttg ggtcaactct ccaatgtcca caggacagaa gccattgaga gagcaaggtt   1680
gcacataggc aaaggtgtgc agttggaatg taaaggtgaa ggtgatgttt gggtcaggtg   1740
ccttagtgac cacgcggtct ttgtacagag ttactacta acagagaag tgggcgtgca   1800
acctggagat gctgttcata agatctaccc aagtgcatat ataaaggtct ttgatttgcg   1860
tcagtgtcat cgacagatgc agcagcaggc ggctactgca caagctgcag cagctgccca   1920
ggcagcagcc gtgcaggaa acatccctgg cccaggatca gtaggtggaa tagctccagc   1980
tatcagtctg tcagctgctg ctggaattgg tgttgatgac cttcgtcgct tatgcatact   2040
caggatgagt tttgtgaaag gctggggacc ggattcccca agacagagca tcaaagaaac   2100
accttgctgg attgaaattc acttacaccg ggccctccag ctcctagacg aagtacttca   2160
taccatgccg attgcagacc cacaaccttt agactgaggt cttttaccgt tggggcctt   2220
aaccttatca ggatggtgga ctacaaaata caatcctgtt tataatctga agatatattt   2280
cactttgtt ctgctttatc ttttcataaa gggttgaaaa tgtgttgct gcttgctcc   2340
tagcagacag aaactggatt aaaacaattt ttttttttcct cttcagaact tgtcaggcat   2400
ggctcagagc ttgaagatta ggagaaacac attcttatta attcttcacc tgttatgtat   2460
gaaggaatca ttccagtgct agaaaattta gccctttaaa acgtcttaga gccttttatc   2520
tgcagaacat cgatatgtat atcattctac agaataatcc agtattgctg atttttaaagg   2580
cagagaagtt ctcaaagtta attcacctat gttattttgt gtacaagttg ttattgttga   2640
acatacttca aaaataatgt gccatgtggg tgagttaatt ttaccaagag taactttact   2700
ctgtgtttaa aaagtaagtt aataatgtat tgtaatcttt catccaaaat atttttttgca   2760
agttatatta gtgaagatgg tttcaattca gattgtcttg caacttcagt tttatttttg   2820
ccaaggcaaa aaactcttaa tctgtgtgta tattgagaat cccttaaaat taccagacaa   2880
aaaaatttaa aattacgttt gttattccta gtggatgact gttgatgaag tatacttttg   2940
ccctgttaaa cagtagttgt attcttctgt atttctaggc acaaggttgg ttgctaagaa   3000
gcctataaga ggaatttctt ttccttcatt cataggaaa ggttttgtat tttttaaaac   3060
actaaaagca gcgtcactct acctaatgtc tcactgttct gcaaaggtgg caatgcttaa   3120
actaaataat gaataaactg aatatttgg aaactgctaa attctatgtt aaatactgtg   3180
cagaataatg gaaacattac agttcataat aggtagtttg gatattttg tacttgattt   3240
```

```
gatgtgactt tttttggtat aatgtttaaa tcatgtatgt tatgatattg tttaaaattc   3300
agttttttgta tcttggggca agactgcaaa cttttttata tcttttggtt attctaagcc  3360
cttttgccatc aatgatcata tcaattggca gtgactttgt atagagaatt taagtagaaa  3420
agttgcagat gtattgactg taccacagac acaaatgta  tgcttttac  ctagctggta   3480
gcataaataa aactgaatct caacatacaa agttgaattc taggtttgat ttttaagatt   3540
ttttttttct tttgcacttt tgagtccaat ctcagtgatg aggtaccttc tactaaatga   3600
caggcaacag ccagttctat tgggcagctt tgttttttttc cctcacactc taccgggact  3660
tccccatgga cattgtgtat catgtgtaga gttggttttt ttttttttta atttttattt   3720
tactatagca gaaatagacc tgattatcta caagatgata aatagattgt ctacaggata   3780
aatagtatga aataaaatca aggattatct ttcagatgtg tttactttttg cctggagaac  3840
ttttagctat agaaacactt gtgtgatgat agtcctcctt atatcacctg gaatgaacac   3900
agcttctact gccttgctca gaaggtcttt taaatagacc atcctagaaa ccactgagtt   3960
tgcttattc  tgtgatttaa acatagatct tgatccaagc tacatgactt ttgtctttaa   4020
ataacttatc taccacctca tttgtactct tgattactta caaattcttt cagtaaacac   4080
ctaattttct tctgtaaaag tttggtgatt taagtttat  tggcagtttt ataaaaagac   4140
atcttctcta gaaattgcta actttaggtc cattttactg tgaatgagga ataggagtga   4200
gttttagaat aacagatttt taaaaatcca gatgatttga ttaaaaccttt aatcatacat   4260
tgacataatt cattgcttct ttttttgag  atatggagtc ttgctgtgtt gcccaggcag   4320
gagtgcagtg gtatgatctc agctcactgc aacctctgcc tcccgggttc aactgattct   4380
cctgcctcag cctccctggt agctaggatt acaggtgccc gccaccatgc ctggctaact   4440
tttgtagttt tagtagagac ggggttttgc ctgttggcca ggctggtctt gaactcctga   4500
cctcaagtga tccatccacc ttggcctccc aaagtgctgg gattacgggc gtgagccact   4560
gtccctggcc tcattgttcc cttttctact ttaaggaaag ttttcatgtt taatcatctg   4620
gggaaagtat gtgaaaaata tttgttaaga agtatctctt tggagccaag ccacctgtct   4680
tggtttcttt ctactaagag ccataaagta tagaaatact tctagttgtt aagtgcttat   4740
atttgtacct agatttagtc acacgctttt gagaaaacat ctagtatgtt atgatcagct   4800
attcctgaga gcttggttgt taatctatat ttctatttct tagtggtagt catctttgat   4860
gaataagact aaagattctc acaggtttaa aattttatgt ctactttaag ggtaaaatta   4920
tgaggttatg gttctgggtg ggtttctctt agctaattca tatctcaaag agtctcaaaa   4980
tgttgaattt cagtgcaagc tgaatgagag atgagccatg tacacccacc gtaagaccctc  5040
attccatgtt tgtccagtgc ctttcagtgc attatcaaag ggaatccttc atggtgttgc   5100
ctttattttc cggggagtag atcgtgggat atagtctatc tcattttttaa tagtttaccg   5160
cccctggtat acaaagataa tgacaataaa tcactgccat ataaccttgc ttttttccaga  5220
aacatggctg ttttgtattg ctgtaaccac taaataggtt gcctatacca ttcctcctga   5280
gaacagtgca gatttgacagg ttgcatggtc tggcttaagg agagccatac ttgagacatg   5340
tgagtaaact gaactcatat tagctgtgct gcatttcaga cttaaaatcc attttttgtgg  5400
ggcagggtgt ggtgtgtaaa gggggggtgtt tgtaatacaa gttgaaggca aaataaaatg   5460
tcctgtctcc cagatgatat acatcttatt atttttaaag tttattgcta attgtaggaa   5520
ggtgagttgc aggtatcttt gactatggtc atctggggaa ggaaaatttt acatttttact  5580
attaatgctc cttaagtgtc tatggaggtt aaagaataaa atggtaaatg tttctgtgcc   5640
tggtttgatg gtaactggtt aatagttact caccattta  tgcagagtca cattagttca   5700
caccctttct gagagccttt tgggagaagc agtttttattc tctgagtgga acagagttct   5760
ttttgttgat aatttctagt ttgctccctt cgttattgcc aactttactg gcattttatt   5820
taatgatagc agattgggaa aatggcaaat ttaggttacg gaggtaaatg agtatatgaa   5880
agcaattacc tctaaagcca gttaacaatt attttgtagg tggggtacac tcagcttaaa   5940
gtaatgcatt tttttttccc gtaaaggcag aatccatctt gttgcagata gctatctaaa   6000
taatctcata tcctcttttg caaagactac agagaatagg ctatacaaat cttgttcaag   6060
cctttccatt tttttccctg ataactaagt aatttctttg aacataccaa gaagtatgta   6120
aaaagtccat ggccttattc atccacaaag tggcatccta ggcccagcct tatccctagc   6180
agttgtccca gtgctgctag gttgcttatc ttgtttatct ggaatcactg tggagtgaaa   6240
ttttccacat catccagaat tgccttattt aagaagtaaa acgttttaat ttttagcctt   6300
ttttttggtgg agttatttaa tatgtatatc agaggatata ctagatggta acatttcttt   6360
ctgtgcttgg ctatctttgt ggacttcagg ggcttctaaa acagacagga ctgtgttgcc   6420
tttactaaat ggtctgagac agctatggtt ttgaattttt agttttttttt ttttaaccca   6480
cttccctcc  tggtctcttc cctctctgat aattaccatt catatgtag  tgttagtgtg   6540
cctccttttta gcatttttctt cttctctttc tgattcttca tttctgactg cctaggcaag   6600
gaaaccagat aaccaaactt actagaacgt tcttttaaaac acaagtacaa actctgggac   6660
aggacccaag acactttcct gtgaagtgct gaaaagagacc tcattgtatt ggcatttgat   6720
atcagtttga tgtagcttag agtgcttcct gattcttgct gagtttcagg tagttgagat   6780
agagagaagt gagtcatatt catatttttcc cccttagaat aatatttga aaggtttcat   6840
tgcttccact tgaatgctgc tcttacaaaa actggggtta caagggttac taaattagca   6900
tcagtagcca gaggcaatac cgttgtctgg aggacaccag caaacaacac acaacaaagc   6960
aaaacaaacc ttgggaaact aaggccattt gttttgtttt ggtgtcccct ttgaagccct   7020
gccttctggc cttactcctg tacagatatt tttgacctat aggtgccttt atgagaattg   7080
agggtctgac atcctgcccc aaggagtagc taaagtaatt gctagtgttt tcagggattt   7140
taacatcaga ctgaatgaa  tgaatgaaac tttttgtcct ttttttttct gttttttttt   7200
ttctaatgta gtaaggacta aggaaaacct tggtgaaga  caatcatttc tctctgttga   7260
tgtggatact tttcacaccg tttatttaaa tgctttctca ataggtccag agccagtgtt   7320
cttgttcaac ctgaaagtaa tggctctggg ttgggccaga cagttgcact ctctagtttg   7380
ccctctgcca caaatttgat gtgtgaccttt ggggcaagtc atttatcttc tctgggcctt   7440
agttgcctca tctgtaaaat gagggagttg gagtagatta attattccag ctctgaaatt   7500
ctaagtgacc ttggctaccct tgcagcagtt ttggatttct tccttatctt tgttctgctg   7560
tttgagggggg ctttttactt atttccatgt tattcaaagg agactaggct tgatattta   7620
ttactgttct tttatggaca aaaggttaca tagtagctta ttaagactta atttaacca    7680
aaggcctagc accaccttag gggctgcaat aaacacttaa cgcgcgtgcg cacgcgcgcg   7740
cgcacacaca cacacacaca cacacacaca caggtcag   agtttaaggc tttcgagtca   7800
tgacattcta gcttttgaat tgcgtgcaca cacacgcga cgcacacact ctggtcagag    7860
tttattaagg ctttcgagtc atgacattat agcttttgag ttggtgtgtg tgacaccacc    7920
ctcctaagtg gtgtgtgctt gtaattttttt tttttcagtga aaatgattg aaaacctgtt   7980
```

```
gttaatgctt agtgatatta tgctcaaaac aaggaaattc ccttgaaccg tgtcaattaa    8040
actggtttat atgactcaag aaaacaatac cagtagatga ttattaactt tattcttggc    8100
tcttttaggg tccattttga ttaagtgact tttggctgga tcattcagag ctctcttcta    8160
gcctacccatt ggatgagtac aattaatgaa attcatattt tcaaggacct gggagccttc    8220
cttggggctg ggttgagggt gggggggttgg ggagtcctgg tagaggccag ctttgtggta    8280
gctggagagg aagggatgaa accagctgct gttgcaaagg ctgcttgtca ttgatagaag    8340
gactcacggg cttggattga ttaagactaa acatggagtt ggcaaacttt cttcaagtat    8400
tgagttctgt tcaatgcatt ggacatgtga tttaagggaa aagtgtgaat gcttatagat    8460
gatgaaaacc tggtgggctg cagagcccag tttagaagaa gtgagttggg ggtggggac    8520
agatttggtg gtgtatttc ccaactgttt cctcccctaa attcagagga atgcagctat    8580
gccagaagcc agagaagagc cactcgtagc ttctgctttg gggacaactg gtcagttgaa    8640
agtcccagga gttcctttgt ggctttctgt atacttttgc ctggttaaag tctgtggcta    8700
aaaaatagtc gaacctttct tgagaactct gtaacaaagt atgtttttga ttaaaagaga    8760
aagccaacta aaaaaaaaaa aaaaaaaa                                        8789

SEQ ID NO: 70           moltype = AA  length = 552
FEATURE                 Location/Qualifiers
source                  1..552
                        mol_type = protein
                        organism = Homo sapiens
SEQUENCE: 70
MDNMSITNTP TSNDACLSIV HSLMCHRQGG ESETFAKRAI ESLVKKLKEK KDELDSLITA    60
ITTNGAHPSK CVTIQRTLDG RLQVAGRKGF PHVIYARLWR WPDLHKNELK HVKYCQYAFD    120
LKCDSVCVNP YHYERVVSPG IDLSGLTLQS NAPSSMMVKD EYVHDFEGQP SLSTEGHSIQ    180
TIQHPPSNRA STETYSTPAL LAPSESNATS TANFPNIPVA STSQPASILG GSHSEGLLQI    240
ASGPQPGQQQ NGFTGQPATY HHNSTTTWTG SRTAPYTPNL PHHQNGHLQH HPPMPPHPGH    300
YWPVHNELAF QPPISNHPAP EYWCSIAYFE MDVQVGETFK VPSSCPIVTV DGYVDPSGGD    360
RPFCLGQLSNV HRTEAIERAR LHIGKGVQLE CKGEGDVWVR CLSDHAVFVQ SYYLDREAGR    420
APGDAVHKIY PSAYIKVFDL RQCHRQMQQQ AATAQAAAAA QAAAVAGNIP GPGSVGGIAP    480
AISLSAAAGI GVDDLRRLCI LRMSFVKGWG PDYPRQSIKE TPCWIEIHLH RALQLLDEVL    540
HTMPIADPQP LD                                                        552

SEQ ID NO: 71           moltype = DNA  length = 5477
FEATURE                 Location/Qualifiers
source                  1..5477
                        mol_type = genomic DNA
                        organism = Homo sapiens
SEQUENCE: 71
aaaaagagaa actgttggga gaggaatcgt atctccatat ttcttctttc agccccaatc    60
caagggttgt agctggaact ttccatcagt tcttcctttc tttttcctct ctaagccttt    120
gccttgctct gtcacagtga agtcagccag agcagggctg ttaaactctg tgaaatttgt    180
cataaggggtg tcaggtattt cttactggct tccaaagaaa catagataaa gaaatctttc    240
ctgtgcctc ccttggcagg ctgcattcag aaggtctctc agttgaagaa agacgttcag    300
ggacaacagc acaacaggag agtaaaagat gccccagggc tgaggcctcc gctcaggcag    360
ccgcatctgg ggtcaatcat actcaccttg cccgggccat gctccagcaa aatcaagctg    420
ttttcttttg aaagttcaaa ctcatcaaga ttatgctgct cactcttatc attctgttgc    480
cagtagtttc aaaatttagt tttgttagtc tctcagcacc gcagcactgg agctgtcctg    540
aaggtactct cgcaggaaat gggaattcta cttgtgtggg tcctgcaccc ttcttaattt    600
tctcccatgg aaatagtatc tttaggattg acacagaagg aaccaattat gagcaattgg    660
tggtggatgc tggtgtctca gtgatcatgg attttcatta taatgagaaa agaatctatt    720
gggtgatttt agaaagacaa cttttgcaaa gagtttttct gaatgggtca aggcaagaga    780
gagtatgtaa tatagagaaa aatgtttctg gaatggcaat aaaattggata aatgaagaag    840
ttatttggtc aaatcaacag gaaggaatca ttacagtaaac agatatgaaa ggaaataatt    900
cccacattct tttaagtgct ttaaaatatc ctgcaaatgt agcagttgat ccagtagaaa    960
ggtttatatt ttggtcttca gaggtggctg gaagccttta tagagcagat ctcgatggtg    1020
tgggagtgaa ggctctgttg gagacatcag agaaaataac agctgtgtca ttggatgtgc    1080
ttgataagcg gctgtttttgg attcagtaca acagagaagg aagcaattct cttatttgct    1140
cctgtgatta tgatgggagt tctgtccaca ttagtaaaca tccaacacag cataatttgt    1200
ttgcaatgtc ccttttggt gaccgtatct tctattcaac atggaaaatg aagacaattt    1260
ggatagccaa caaacacact ggaaaggaca tggttagaat taacctccat tcatcatttg    1320
taccacttgg tgaactgaaa gtagtgcatc cacttgcaca acccaaggca gaagatgaca    1380
cttgggagcc tgagcagaaa cttttgcaaat tgaggaaagg aaactgcagc agcactgtgt    1440
gtgggcaaga cctccagtca cacttgtgca tgtgtgcaga gggatacgcc ctaagtcgag    1500
accggaagta ctgtgaagat gttaatgaat gtgcttttg gaatcatgcc tgtactctg    1560
ggtgtaaaaa cacccctgga tcctattact gcacgtgccc tgtaggattt gttctgcttc    1620
ctgatgggaa acgatgtcat caacttgttt cctgtccacg caatgtgtct gaatgcagcc    1680
atgactgtgt tctgacatca gaaggtccct tatgtttctg tcctgaaggc tcagtgcttg    1740
agagagatgg gaaaacatgt agcggttgtt cctcacccga taatggtgga tgtgccagc    1800
tctcgttcc tcttagccca gtatcctggg aatgtgattg ctttctggg tatgaccatc    1860
aactggatga aaaaagctgt gcagcttcag gaccacaacc atttttgctg tttgccaatt    1920
ctcaagatat tcgacacatg cattttgatg aacagactc tggaactctg ctcagccagc    1980
agatgggaat ggtttatgcc ctagatcatg acctgtgga aaataagata tactttgccc    2040
atacagcccct gaagtggata gagagcta atatggatgg ttcccagcga gaaaggctta    2100
ttgagggagg agtagatgtg caaagttc ttgctgtga ctggattgc cgtagatct    2160
attggacaga cagagggaaa tctctgattg gaagagtga tttaaatggg aaacgttcca    2220
aaataatcac taaggagaac atctctcaac cacgaggaat tgctgttcat ccaatggcca    2280
agagattatt ctggactgat acagggatta tccacgaat tgaaagttct ccctccaag    2340
gccttggccg tctggttata gccagctctg atctaatctg gccagtggaa ataacgattg    2400
acttcttaac tgacaagttg tactggtgcg atgccaagca gtctgtgatt gaaatggca    2460
```

-continued

```
atctggatgg ttcaaaacgc cgaagactta cccagaatga tgtaggtcac ccatttgctg  2520
tagcagtgtt tgaggattat gtgtggttct cagattgggc tatgccatca gtaatgagag  2580
taaacaagag gactggcaaa gatagagtac gtctccaagg cagcatgctg aagccctcat  2640
cactggttgt ggttcatcca ttggcaaaac caggagcaga tccctgctta tatcaaaacg  2700
gaggctgtga acatatttgc aaaaagaggc ttggaactgc ttggtgttcg tgtcgtgaag  2760
gttttatgaa agcctcagat gggaaaacgt gtctggctct ggatggtcat cagctgttgg  2820
caggtggtga agttgatcta agaaccaag taacaccatt ggacatcttg tccaagacta  2880
gagtgtcaga agataacatt acagaatctc aacacatgct agtggctgaa atcatggtgt  2940
cagatcaaga tgactgtgct cctgtgggat gcagcatgta tgctcggtgt atttcagagg  3000
gagaggatgc cacatgtcag tgtttgaaag gatttgctgg ggatggaaaa ctatgttctg  3060
atatagatga atgtgagatg ggtgtcccag tgtgcccccc tgcctcctcc aagtgcatca  3120
acaccgaagg tggttatgtc tgccggtgct cagaaggcta ccaaggagat gggattcact  3180
gtcttgactc tactccaccc cctcacctca gggaagatga ccaccactat tccgtaagaa  3240
atagtgactc tgaatgtccc ctgtcccacg atgggtactg cctccatgat ggtgtgtgca  3300
tgtatattga agcattggac aagtatgcat gcaactgtgt tgttggctac atcggggagc  3360
gatgtcagta ccgagacctg aagtggtggg aactgcgcca cgctgccac gggcagcagc  3420
agaaggtcat cgtggtggct gtctgcgtgg tggtgcttgt catgctgctc ctcctgagcc  3480
tgtggggggc ccactactac aggactcaga agctgctatc gaaaaaccca aagaatcctt  3540
atgaggagtc gagcagagat gtgaggagtc gcaggcctgc tgacactgag gatgggatgt  3600
cctcttgccc tcaaccttgg tttgtggtta taaaagaaca ccaagacctc aagaatgggg  3660
gtcaaccagt ggctggtgag gatggccagg cagcagatgg gtcaatgcaa ccaacttcat  3720
ggaggcagga gccccagtta tgtggaatgg gcacagagga aggctgctgg attccagtat  3780
ccagtgataa gggctcctgt ccccaggtaa tggagcgaag cttcatatg ccctcctatg  3840
ggacacagac ccttgaaggg ggtgtcgaga agccccattc tctcctatca gctaacccat  3900
tatggcaaca aagggccctg gacccaccac accaaatgga gctgactcag tgaaaactgg  3960
aattaaaagg aaagtcaaga agaatgaact atgtcgatgc agatatctt ttcttcaa  4020
agtagagcaa aactataggt tttgttcca caatctctac gactaatcac ctactcaatg  4080
cctggagaca gatacgtagt tgtgcttttg tttgctcttt taagcagtct cactgcagtc  4140
ttatttccaa gtaagagtac tgggagaatc actaggtaac ttattagaaa cccaaattgg  4200
gacaacagtg ctttgtaaat tgtgttgtct tcagcagtca atacaaatag attttttgtt  4260
ttgttgttcc tgcagcccca gaagaaatta ggggttaaag cagacagtca cactggtttg  4320
gtcagttaca aagtaatttc tttgatctgg acagaacatt tatatcagtt tcatgaaatg  4380
attggaatat tacaataccg ttaagataca gtgtaggcat ttaactcctc attggcgtgg  4440
tccatgctga tgatttttgca aaatgagttg tgatgaatca atgaaaaatg taatttagaa  4500
actgatttct tcagaattag atggcttatt ttttaaaata tttgaatgata aacattttat  4560
ttttaaaata ttcacagga ggcttcggag tttcttagtc attactgtcc ttttcccta  4620
cagaattttc cctcttggtg tgattgcaca gaatttgtat gtattttcag ttacaagatt  4680
gtaagtaaat tgcctgattt gtttttcatta tagacaacga tgaattcttt ctaattattt  4740
aaataaaatc accaaaaaca taaacatttt attgtatgcc tcattaagta gttaattata  4800
gtctaaggca gtactagagt tgaaccaaaa tgatttgtca agcttgctga tgtttctgtt  4860
tttcgttttt ttttttttc cggagagagg ataggatctc actctgttat ccaggctgga  4920
gtgtgcaatg gcacaatcat agctcagtgc agccctcaaac tcctgggctc aagcaatcct  4980
cctgcctcag cctcccgagt aacaggaccc acaggcagc agccaccatgc ctggctaagg  5040
ttttattttt tatttttttgt agacatgggg atcacacaat gttgcccagg ctggtcttga  5100
actcctggcc tcaagcaagg tcgtgctggt aatttgcaa aatgaattgt gattgacttt  5160
cagcctccca acgtattaga ttataggcat tagccatggt gcccagcctt gtaacttta  5220
aaaaattt ttaatctaca actctgtaga ttaaaattc actggtgtt ctaattaaat  5280
attttcttg cagccaagat attgttacta cagataacac aacctgatat ggtaacttta  5340
aattttgggg gctttgaatc attcagtttta tgcattaact agtccctttg tttatctttc  5400
atttctcaac cccttgtact ttggtgatac cagacatcag aataaaaaga aattgaagta  5460
aaaaaaaaaa aaaaaaa                                                  5477
```

```
SEQ ID NO: 72           moltype = AA   length = 1166
FEATURE                 Location/Qualifiers
source                  1..1166
                        mol_type = protein
                        organism = Homo sapiens
SEQUENCE: 72
MLLTLIILLP VVSKFSFVSL SAPQHWSCPE GTLAGNGNST CVGPAPFLIF SHGNSIFRID   60
TEGTNYEQLV VDAGVSVIMD FHYNEKRIYW VDLERQLLQR VFLNGSRQER VCNIEKNVSG  120
MAINWINEEV IWSNQQEGII TVTDMKGNNS HILLSALKYP ANVAVDPVER FIFWSSEVAG  180
SLYRADLDGV GVKALLETSE KITAVSLDVL DKRLFWIQYN REGSNSLICS CDYDGGSVHI  240
SKHPTQHNLF AMSLFGDRIF YSTWKMKTIW IANKHTGKDM VRINLHSSFV PLGELKVVHP  300
LAQPKAEDDT WEPEQKLCKL RKGNCSSTVC GQDLQSHLCM CAEGYALSRD RKYCEDVNEC  360
AFWNHGCTLG CKNTPGSYYC TCPVGFVLLP DGKRCHQLVS CPRNVSECSH DCVLTSEGPL  420
CFCPEGSVLE RDGKTCSGCS SPDNGGCSQL CVPLSPVSWE CDCFPGYDLQ LDEKSCAASG  480
PQPFLLFANS QDIRHMHFDG TDYGTLLSQQ MGMVYALDHD PVENKIYFAH TALKWIERAN  540
MDGSQRERLI EEGVDVPEGL AVDWIGRRFY WTDRGKSLIG RSDLNGKRSK IITKENISQP  600
RGIAVHPMAK RLFWTDTGIN PRIESSSLQG LGRLVIASSD LIWPSGITID FLTDKLYWCD  660
AKQSVIEMAN LDGSKRRRLT QNDVGHPFAV AVFEDYVWFS DWAMPSVMRV NKRTGKDRVR  720
LQGSMLKPSS LVVVHPLAKP GADPCLYQNG GCEHICKKRL GTAWCSCREG FMKASDGKTC  780
LALDGHQLLA GGEVDLKNQV TPLDILSKTR VSEDNITESQ HMLVAEIMVS DQDDCAPVGC  840
SMYARCISEG EDATCQCLKG FAGDGKLCSD IDECEMGVPV CPPASSKCIN TEGGYVCRCS  900
EGYQGDGIHC LDSTPPPHLR EDDHHYSVRN SDSECPLSHD GYCLHDGVCM YIEALDKYAC  960
NCVVGYIGER CQYRDLKWWE LRHAGHGQQQ KVIVVAVCVV VLVMLLLLSL WGAHYYRTQK 1020
LLSKNPKNPY EESSRDVRSR RPADTEDGMS SCPQPWFVVI KEHQDLKNGG QPVAGEDGQA 1080
ADGSMQPTSW RQEPQLCGMG TEQGCWIPVS SDKGSCPQVM ERSFHMPSYG TQTLEGGVEK 1140
PHSLLSANPL WQQRALDPPH QMELTQ                                      1166
```

| SEQ ID NO: 73 | moltype = DNA length = 4815 |
|---|---|
| FEATURE | Location/Qualifiers |
| source | 1..4815 |
| | mol_type = genomic DNA |
| | organism = Homo sapiens |

SEQUENCE: 73

```
agtggcgtcg gaactgcaaa gcacctgtga gcttgcggaa gtcagttcag actccagccc    60
gctccagccc ggcccgaccc gaccgcaccc ggcgcctgcc ctcgctcggc gtccccggcc   120
agccatgggc ccttggagcc gcagcctctc ggcgctgctg ctgctgctgc aggtctcctc   180
ttggctctgc caggagccgg agccctgcca ccctggcttt gacgccgaga gctacacgtt   240
cacggtgccc cggcgccacc tggagagagg ccgcgtcctg ggcagagtga attttgaaga   300
ttgcaccggt cgacaaagga cagcctattt ttccctcgac acccgattca aagtgggcac   360
agatggtgtg attacagtca aaaggcctct acggtttcat aacccacaga tccatttctt   420
ggtctacgcc tgggactcca cctacagaaa gttttccacc aaagtcacgc tgaatacagt   480
ggggcaccac caccgccccc cgccccatca ggcctccgtt tctggaatcc aagcagaatt   540
gctcacattt cccaactcct ctcctggcct cagaagacag aagagagact gggttattcc   600
tcccatcagc tgcccagaaa atgaaaaagg cccatttcct aaaaacctgg ttcagatcaa   660
atccaacaaa gacaaagaag gcaaggtttt ctacagcatc actggccaag gagctgacac   720
accccctgtt ggtgtcttta ttattgaaag agaaacagga tggctgaagg tgacagagcc   780
tctggataga aacgcattgc cacatacac tctcttctct cacgctgtgt catccaacgg   840
gaatgcagtt gaggatccaa tggagatttt gatcacggta accgatcaga atgacaacaa   900
gcccgaattc acccaggagg tctttaaggg gtctgtcatg gaagtgctc ttccaggaac   960
ctctgtgatg gaggtcacag ccacagacgc ggacgatgat gtgaacacct acaatgccgc  1020
catcgcttac accatcctca gccaagatcc tgagctccct gacaaaaata tgttcaccat  1080
taacaggaac acaggagtca tcagtgtggt caccactggg ctggaccgag agtttccc    1140
tacgtatacc ctggtggttc aagctgctga ccttcaaggt gagggggttaa gcacaacagc  1200
aacagctgtg atcacagtca ctgacaccaa cgataatcct ccgatcttca atcccaccac  1260
gtacaagggt caggtgcctg agaacgaggc taacgtcgta atcaccacac tgaaagtgac  1320
tgatgctgat gccccccaata cccagcgtg ggaggctgta tacaccatat gaatgatga   1380
tggtggacaa tttgtcgtca ccacaaatcc agtgaacaac gatgcatt tgaaaacgat  1440
aaagggcttg gattttgagg ccaagcagca gtacattcta cacgtagcag tgacgaatgt  1500
ggtaccttt gaggtctctc tcaccacctc cacagccacc gtcaccgtgg atgtgctgga  1560
tgtgaatgaa gcccccatct ttgtgcctcc tgaaaagaga gtggaagtgt ccgaggactt  1620
tggcgtgggc caggaaatca catcctacac tgcccaggag ccagacacat ttatggaaca  1680
gaaaataaca tatcggattt ggagagacac tgccaactgg ctggagatta atccggacac  1740
tggtgccatt tccactcggg ctgagctgga cagggaggat tttgagcacg tgaagaacag  1800
cacgtacaca gccctaatca tagctacaga caatggttct ccagttgcta ctggaacagg  1860
gacacttctg ctgatcctgt ctgatgtgaa tgacaacgc cccataccag aacctcgaac  1920
tatattcttc tgtgagagga atccaaagcc tcaggtcata aacatcattg atgcagacct  1980
tcctcccaat acatctccct tcacagcaga actaacacac ggggcgagtg ccaactggac  2040
cattcagtac aacgacccaa cccaagaatc tatcattttg aagccaaaga tggccttaga  2100
ggtgggtgac tacaaaatca atctcaagct catggataac cagaataaag accaagtgac  2160
caccttagag gtcagcgtgt gtgactgtga agggcgcgct ggcgtctgta ggaaggcaca  2220
gcctgtcgaa gcaggattgc aaattcctgc cattctgggg attcttggag gaattcttgc  2280
tttgctaatt ctgattctgc tgctcttgct gtttcttcgg aggagagcgg tggtcaaaga  2340
gcccttactg ccccagagg atgacacccg ggacaacgtt tattactatg atgaagaagg  2400
aggcggagaa gaggaccagg actttgactt gagccagctc cacaggggcc tggacgctg   2460
gcctgaagtg actcgtaacg acgttgcacc aaccctcatg agtgtccccc ggtatcttcc  2520
ccgccctgcc aatcccgatg aaattggaaa ttttattgat gaaaatctga aagcggctga  2580
tactgaccc acagccccgc cttatgattc tctgctcgtg tttgactatg aaggaagcgg  2640
ttccgaagct gctagtctga gctccctgaa ctcctcagag tcagacaaag accaggacta  2700
tgactacttg aacgaatggg gcaatcgctt caagaagctg gctgacatgt acggaggcgg  2760
cgaggacgac tagggggactc gagagaggcg ggcccagac ccatgtgctg ggaaatgcag  2820
aaatcacgtt gctggtggtt tttcagctcc cttcccttga tgagtttc tggggaaaaa  2880
aaagagactg gttagtgatg cagttagtat agctttatac tctctccact ttatagctct  2940
aataagtttg tgttagaaaa gtttcgactt atttcttaaa gcttttttt ttttcccatc  3000
actctttaca tggtggtgat gtccaaaaga tacccaaatt ttaatattcc agaagaacaa  3060
ctttagcatc agaaggttca cccagcacct tgcagatttt cttaaggaat tttgtctcac  3120
ttttaaaaag aaggggagaa gtcagctact ctagttctgt tgtttttgtg atataattt   3180
ttaaaaaaaa tttgtgtgct tctgctcatt actacactgg tgtgtccctc tgccttttt   3240
tttttttaa gacagggtct cattctatcg gccaggctgg agtgcagtgg tgcaatcaca   3300
gctcactgca gccttgtcct cccaggctca agctatcctt gcacctcagc ctcccaagta   3360
gctgggacca caggcatgca ccactacgca tgactaattt tttaaatatt tgagacgggg   3420
tctccctgtg ttacccaggc tggtctcaaa ctcctggcct caagtgatcc tcccatcttg   3480
gcctcccaga gtattgggat tacagacatg agccactgca cctgcccagc tcccaactc    3540
cctgccattt tttaagagac agtttcgctc catcgcccag gctgggatg cagtgatgtg   3600
atcatagctc actgtaacct caaactctgg ggctcaagca gttctccac cagcctcctt   3660
tttatttttt tgtacagatg gggtcttgct atgttccca agctggtctt aaactcctgg   3720
cctcaagcaa tccttctgcc ttggccccc aaagtgctgg gattgtgggc atgagctgct   3780
gtgcccagcc tccatgtttt aatatcaact ctcactcctg aattcagttg ctttgcccaa   3840
gataggagtt ctctgatgca gaaattattg ggctctttta gggtaagaag tttgtgtctt   3900
tgtctggcca catcttgact aggtattgtc tactctgaag acctttaatg gcttccctct   3960
ttcatctcct gagtatgtaa cttgcaatgg gcagctatcc agtgacttgt tctgagtaag   4020
tgtgttcatt aatgtttatt tagctctgaa gcaagagtaa tatctccag gacttagaat   4080
agtgcctaaa gtgctgcagc caaagacaga gcgaactat gaaaagtggg cttgagatg    4140
gcaggagagc ttgtcattga gcctggcaat ttagcaaact gatgctgagg atgattgagg   4200
tgggtctacc tcatctctga aaattctgga aggaatggag gagtctcaac atgtgtttct   4260
gacacaagat ccgtggtttg tactcaaagc ccagaatccc caagtgcctg cttttgatga   4320
tgtctacaga aaatgctggc tgagctgaac acatttgccc aattccaggt gtgcacagaa   4380
```

-continued

```
aaccgagaat attcaaaatt ccaaattttt ttcttaggag caagaagaaa atgtggccct    4440
aaaggggtt  agttgagggg taggggggtag tgaggatctt gatttggatc tcttttatt    4500
taaatgtgaa tttcaacttt tgacaatcaa agaaaagact tttgttgaaa tagctttact    4560
gtttctcaag tgttttggag aaaaaaatca accctgcaat cacttttggg aattgtcttg    4620
attttccggc agttcaagct atatcgaata tagttctgtg tagagaatgt cactgtagtt    4680
ttgagtgtat acatgtgtgg gtgctgataa ttgtgtattt tctttggggg tggaaaagga    4740
aaacaattca agctgagaaa agtattctca aagatgcatt tttataaatt ttattaaaca    4800
attttgttaa accat                                                    4815

SEQ ID NO: 74           moltype = AA  length = 882
FEATURE                 Location/Qualifiers
source                  1..882
                        mol_type = protein
                        organism = Homo sapiens
SEQUENCE: 74
MGPWSRSLSA LLLLLQVSSW LCQEPEPCHP GFDAESYTFT VPRRHLERGR VLGRVNFEDC     60
TGRQRTAYFS LDTRFKVGTD GVITVKRPLR FHNPQIHFLV YAWDSTYRKF STKVTLNTVG    120
HHHRPPPHQA SVSGIQAELL TFPNSSPGLR RQKRDWVIPP ISCPENEKGP FPKNLVQIKS    180
NKDKEGKVFY SITGQGADTP PVGVFIIERE TGWLKVTEPL DRERIATYTL FSHAVSSNGN    240
AVEDPMEILI TVTDQNDNKP EFTQEVFKGS VMEGALPGTS VMEVTATDAD DDVNTYNAAI    300
AYTILSQDPE LPDKNMFTIN RNTGVISVVT TGLDRESFPT YTLVVQAADL QGEGLSTTAT    360
AVITVTDTND NPPIFNPTTY KGQVPENEAN AVYITLNDDG                         420
GQFVVTTNPV NNDGILKTAK GLDFEAKQQY ILHVAVTNVV PFEVSLTTST ATVTVDVLDV    480
NEAPIFVPPE KRVEVSEDFG VGQEITSYTA QEPDTFMEQK ITYRIWRDTA NWLEINPDTG    540
AISTRAELDR EDFEHVKNST YTALIIATDN GSPVATGTGT LLLILSDVND NAPIPEPRTI    600
FFCERNPKPQ VINIIDADLP PNTSPFTAEL THGASANWTI QYNDPTQESI ILKPKMALEV    660
GDYKINLKLM DNQNKDQVTT LEVSVCDCEG AAGVCRKAQP VEAGLQIPAI LGILGGILAL    720
LILILLLLLF LRRRAVVKEP LLPPEDDTRD NVYYYDEEGG GEEDQDFDLS QLHRGLDARP    780
EVTRNDVAPT LMSVPRYLPR PANPDEIGNF IDENLKAADT DPTAPPYDSL LVFDYEGSGS    840
EAASLSSLNS SESDKDQDYD YLNEWGNRFK KLADMYGGGE DD                      882

SEQ ID NO: 75           moltype = DNA  length = 3328
FEATURE                 Location/Qualifiers
source                  1..3328
                        mol_type = genomic DNA
                        organism = Homo sapiens
SEQUENCE: 75
ccggaagtgc tgcgagccct gggccacgct ggccgtgctg gcagtgggcc gcctcgatcc      60
ctctgcagtc tttcccttga ggctccaaga ccagcaggtg aggcctcgcg cgctgaaac     120
cgtgaggccc ggaccacagg ctccagatgg accctgggaa ggacaaagag ggggtgcccc     180
agccctcagg gccgccagca aggaagaaat ttgtgatacc cctcgacgag gatgaggtcc     240
ctcctggagt ggcaagccc  ttattccgat ctacacagag ccttcccact gtggacacct     300
cggccaggc  ggccccctcag acctacgcg  aaatatgcca ctcacagcct ctggaagggg    360
ctggggccac gtgccccaca gggtcagagc ccctggcagg agagacgccc aaccaggccc     420
tgaaaccggg ggcaaaatcc aacagcatca ttgtgagccc tcggcagagg ggcaatcccg     480
tactgaagtt cgtgcgcaat gtgccctggg aatttggcga cgtaattccc gactatgtgc     540
tgggccagag cacctgtgcc ctgttcctca gcctccgtca ccacaacctg cacccagact     600
acatccatgg gcggctgcag agcctggggta agaacttcgc cttgcgggtc ctgcttgtcc     660
aggtggatgt gaaagatccc cagcaggccc tcaaggagct ggctaagatg tgtatcctgg     720
ccgactgcac attgatcctc gcctggagcc ccgaggaagc tgggcggtac ctggagacct     780
acaaggccta tgagcagaaa ccagcaggac tcctgatgga gaagctagag caggacttcg     840
tctcccggtc tctggaacag ctcatcgccg catcaagaga agatctggcc ttatgccag     900
gcctgggccc tcagaaagcc cggaggctgt tgatgtcct gcacgagccc ttcttgaaag     960
taccctgatg accccagctg ccaaggaaac ccccagtgta ataataaatc gtcctcccag    1020
gccaggctcc tgctggctgc gctggtgcag tctctgggga gggattctgg gggtgtcacc    1080
ttctggtggc ccaggtgggc accttcagct ttcttttagt cctcagtttc ccggggcag    1140
actacacagg ctgctgctgc tgctgcttcc gcttcttgtc ccggcctgtg ggagcctcct    1200
ccccagactc tgaattcagt ggcggccctg gcatctcctc ttggggcact gtctctggca    1260
tccggctttc ctgactctgc ttcttcctct tcttggtgga tcccggagtt gccctggctt    1320
caggctgtcc ctcccctggc agttcaggct ctagtggctg aattgctca gtcactgtgt    1380
gacctctctc tttcttcttc ttcttcttct tggtggatgt gggagctgcc tgaggctcaa    1440
ggtcatccgg cagctcaggc cccaccacct ctgtctctgg ctccactgtg gcatcttgct    1500
gttttctttt cttcgtcttc ttttttgggag ctgccagagc tgcctgggcc tgaggcttcg    1560
ctccttctgg ctgttgaggc gccatggtcc ccctgggga tctcagagga ttcatcctcg    1620
gctccactgg ctccatcgcc tccgtccctg gctccatcat tgccatctgt ccctttttctt    1680
ttttcctctt cttcgtaggg ggcagaggga tggcttcctc cagtggctcc accttcacct    1740
gtggctgaga ctcaactgtc acccctcct ctggctccat cccttccgtc cccttttgcc    1800
tcttttctctt tttggtcggg gacaggactg tgtcttctag aggctcagtg ttaatctgtt    1860
cctgcttcac tgtcttgtct gctgtcga  aggttttctt cccttgggc ttcttcctct    1920
tcttggtggt ggacgggaac agcactccca gaggctccag tgtctccact gtgggctctg    1980
tccccacagg ccctgctgcc tctgttcttc tcagctgctg attttttttc ttcttcttct    2040
tccgcacatc catttctggc gaccccaaag ccatgtccac ctccagggcc ccgtgccat     2100
tcactgcctc ctgagtgact ggggcctctg tcacctgcat ctccttttct tcttccctg     2160
aggtgagcag gttggggggc aaggctgacc taggcccctg gggtgggg ttgccccaa      2220
aggcacagaa ccgaggcctc aggcaggag  ggatctgtgg tggggacttt gctgggatgg    2280
gctgcagagg gctccctgac agggattgct ggggaccctc aaggatcctt agggtgccct    2340
gggggggctga ggcacaggtg agtccacctc ctgcctccgt tgagggggcc agcagggtcg    2400
cttcctccagc ttggggacag ctgctgagga ctcgatagcg tgccgcttg cctgccaatt    2460
tgcccttgac gatctgggag ccagagagag gcacatgccg cccattgaag ctacagagag    2520
```

```
aaacagggag ggcagaggct taagtgaac aggagaggga aggttttttg attttttttt  2580
tgttttttt  tgagagagtc ttgctctgtt gcctaggctg gagtgcagtg gcatgatctc  2640
ggctcactgc aatgtccacc tcctgggttc aagcgattct cctgcctcag cctctcaagt  2700
agctgggatt acaggcacct gccaccacgc ccagccaatt tttgtatttt tagtagagac  2760
aatttcacta tgttggccag gctggtcttg aactcctgac ctcaagtgat ctgctcgcct  2820
cggcctccca aggatgggga ttacaggcac cagccactgc gcctggctgg cctctggttt  2880
ttaataaaac atgactagag tgactccatc ttaaagtgag tagctaggca cttacaaggt  2940
tcatgcttat ggcctgaaaa taaccacatc ccaggctgac caccaattat aattacagaa  3000
tatttatggc catacagaac atgttccacc aagcctgcaa aatgtccaaa tgtcctaaga  3060
atgcagcccc cattacttaa atataacata aatgagcaag cttaggttgc aggattaatg  3120
gtcgtggata acaccaatag cccctacctt tagtgagctt atctgcacac tccaagttta  3180
actatagttc cttatagttt cttataagta gaaatactaa caaagggctg tgggtttctc  3240
cccctgcttt ctgaggacac tctactctgt aaaggagtag tttccaataa acttgtttct  3300
ttcactgtgc aaaaaaaaaa aaaaaaaa                                    3328

SEQ ID NO: 76          moltype = AA   length = 273
FEATURE                Location/Qualifiers
source                 1..273
                       mol_type = protein
                       organism = Homo sapiens
SEQUENCE: 76
MDPGKDKEGV PQPSGPPARK KFVIPLDEDE VPPGVAKPLF RSTQSLPTVD TSAQAAPQTY   60
AEYAISQPLE GAGATCPTGS EPLAGETPNQ ALKPGAKSNS IIVSPRQRGN PVLKFVRNVP  120
WEFGDVIPDY VLGQSTCALF LSLRYHNLHP DYIHGRLQSL GKNFALRVLL VQVDVKDPQQ  180
ALKELAKMCI LADCTLILAW SPEEAGRYLE TYKAYEQKPA DLLMEKLEQD FVSRSLEQLI  240
AASREDLALC PGLGPQKARR LFDVLHEPFL KVP                              273

SEQ ID NO: 77          moltype = DNA   length = 2204
FEATURE                Location/Qualifiers
source                 1..2204
                       mol_type = genomic DNA
                       organism = Homo sapiens
SEQUENCE: 77
ggagccccgg ctcctaggct gacagaccag cccagatcca gtggcccgga ggggcctgag   60
ctaaatccgc aggacctggg taacacgagg aagtcggttt ggtccccttta gggctccgga  120
tatctttggt gacttgtcca ctccagtgtg gcatcatgtg gcagctgctc ctcccaactg  180
ctctgctact tctagtttca gctggcatgc ggactgaaga tctcccaaag gctgtggtgt  240
tcctggagcc tcaatgggta caggggctcg agaaggacaa tgtgactctg aagtgccagg  300
gagcctactc ccctgaggac aattccacac agtggttcca caatgagagc ctcatctcca  360
gccaggcctc gagctacttc attgacgctg ccacagtcga cgacagtgga gagtacaggt  420
gccagacaaa cctctccacc ctcagtgacc cggtgcagct agaagtccat atcggctggc  480
tgttgctcca ggccctcggt gggtgttca aggaggaaga cccattcac ctgaggtgtc   540
acagctggaa gaacactgct ctgcataagg tcacatattt acagaatgcc aaaggcagga  600
agtattttca tcataattct gacttctaca ttccaaaagc cacactcaaa gacagcggcc  660
cctacttctg cagggggctt tttgggagta aaaatgtgtc ttcagagact gtgaacatca  720
ccatcactca aggtttggca gtgtcaacca tctcatcatt ctttccacct gggtaccaag  780
tctctttctg cttggtgatg gtactccttt ttgcagtgga cacagacta tatttctctg  840
tgaagacaaa cattcgaagc tcaacaagag actggaagga ccataaattt aaatggagaa  900
aggaccctca agacaaatga ccccccatccc atggggtaa taagagcagt agcagcagca  960
tctctgaaca tttctctgga tttgcaaccc catcatcctc aggcctctct acaagcagca 1020
ggaaacatag aactcagagc cagatcccttt atccaactct cgacttttcc ttggtctcca 1080
gtggaaggga aaagcccatg atcttcaagc agggaagccc cagtgagtag ctgcattcct 1140
agaaattgaa gttcagagc tacacaaaca cttttttctgt cccaaccgtt ccctcacagc 1200
aaagcaacaa tacaggctag ggatggtaat cctttaaaca tacaaaaatt gctcgtgtta 1260
taaattaccc agtttagagg ggaaaaaaaa acaattatct ctaaataaat ggataagtag 1320
aattaatggt tgaggcagga ccatacagag tgtgggaact gctggggatc tagggaattc 1380
agtgggacca atgaaagcat ggctgagaaa tagcaggtag tccaggatag tctaagggag 1440
gtgttcccat ctgagcccag agataagggt gtcttcctag aacattagcc gtagtggaat 1500
taacaggaaa tcatgagggt gacgtagaat tgagtcttcc aggggactct atcagaactg 1560
gaccatctcc aagtatataa cgatgagtcc tcttaatgct aggagtagaa aatggtccta 1620
ggaagggggac tgaggattgc ggtgggggt ggggtggaaa agaaagtaca gaacaaaccc 1680
tgtgtcactg tcccaagttg ctaagtgaac agaactatct cagcatcaga atgagaaagc 1740
ctgagaagaa agaaccaacc acaagcacac aggaaggaaa gcgcaggagg tgaaaatgct 1800
ttcttggcca gggtagtaag aattagaggt taatgcaggt actgtaaaac caccttttct 1860
gcttcaatat ctaattcctg tgtagctttg ttcattgcat ttattaaaca aatgttgtat 1920
aaccaatact aaatgtacta ctgagcttcg ctgagttaag ttatgaaact ttcaaatcct 1980
tcatcatgtc agttccaatg aggtggggat ggagaagaca attgttgctt atgaaagaaa 2040
gctttagctg tctctgtttt gtaagcttta agcgcaacat ttcttggttc caataaagca 2100
tttacaaga tcttgcatgc tactcttaga tagaagatgg gaaaaccatg gtaataaaat 2160
atgaatgata aaaaaaaaaa aaaaaaaa aaaaaaaaaa aaaa                   2204

SEQ ID NO: 78          moltype = AA   length = 254
FEATURE                Location/Qualifiers
source                 1..254
                       mol_type = protein
                       organism = Homo sapiens
SEQUENCE: 78
MWQLLLLPTAL LLLVSAGMRT EDLPKAVVFL EPQWYRVLEK DSVTLKCQGA YSPEDNSTQW   60
FHNESLISSQ ASSYFIDAAT VDDSGEYRCQ TNLSTLSDPV QLEVHIGWLL LQAPRWVFKE  120
```

-continued

```
EDPIHLRCHS WKNTALHKVT YLQNGKGRKY FHHNSDFYIP KATLKDSGSY FCRGLFGSKN    180
VSSETVNITI TQGLAVSTIS SFFPPGYQVS FCLVMVLLFA VDTGLYFSVK TNIRSSTRDW    240
KDHKFKWRKD PQDK                                                     254
```

METHODS AND COMPOSITIONS FOR PREDICTION OF THERAPEUTIC EFFICACY OF CANCER TREATMENTS AND CANCER PROGNOSIS

CROSS REFERENCE TO RELATED APPLICATIONS

This application is a divisional application of U.S. patent application Ser. No. 17/133,107, which was filed on Dec. 23, 2020 as a divisional application of U.S. patent application Ser. No. 15/565,306, issued as U.S. Pat. No. 10,927,412, which was filed as a national stage entry of international application PCT/EP2016/058061, which was filed on Apr. 13, 2016 and claimed priority to international application PCT/EP2015/058212, which was filed on Apr. 15, 2015, the entire contents of which are incorporated herein by reference.

SEQUENCE LISTING

The instant application contains a Sequence Listing which has been submitted electronically in XML format and is hereby incorporated by reference in its entirety. Said XML copy, created on Jun. 5, 2023, is named "026156-8046 Sequence Listing.xml" and is 135,500 bytes in size.

TECHNICAL FIELD OF THE INVENTION

The invention generally relates to methods and compositions for the prediction of therapeutic efficacy of cancer treatments and the prognosis of cancer. The invention discloses markers that are associated with favorable and unfavorable outcomes, respectively, in certain cancer treatments and are useful as prognostic markers for cancer. Methods involving these markers are disclosed for predicting cancer therapy benefit and prognosing clinical outcome for cancer patients.

BACKGROUND OF THE INVENTION

Cancers of the stomach and the esophagus (gastroesophageal; GE) are among the malignancies with the highest unmet medical need. Gastric cancer is the second leading cause of death worldwide. The incidence of esophageal cancer has increased in recent decades and the overall five-year survival rate for GE cancer is 20-25%, despite the aggressiveness of established standard treatment associated with substantial side effects. The medical need of patients suffering from this cancer type is high and innovative drugs are required.

The tight junction molecule claudin 18 isotype 2 (CLDN18.2) is a cancer-associated splice variant of Claudin 18 [Niimi, T., et al., Mol Cell Biol, 2001. 21(21): p. 7380-90; Tureci, O., et al., Gene, 2011. 481(2): p. 83-92]. CLDN18.2 is a 27.8 kDa transmembrane protein comprising four membrane spanning domains with two small extracellular loops (loop1 embraced by hydrophobic region 1 and hydrophobic region 2; loop2 embraced by hydrophobic regions 3 and 4). CLDN18.2 is a highly selective gastric lineage antigen, exclusively expressed on short-lived differentiated gastric epithelial cells and not detectable in any other normal human tissue. The antigen is ectopically expressed at significant levels in a diversity of human cancers including gastroesophageal and pancreatic cancer [Sahin, U., et al., Clin Cancer Res, 2008. 14(23): p. 7624-34]. The CLDN18.2 protein is also frequently detected in lymph node metastases of gastric cancer and in distant metastases. CLDN18.2 seems to be involved in proliferation of CLDN18.2 positive tumor cells, since down regulation of the target by siRNA technology results in inhibition of proliferation of gastric cancer cells.

IMAB362 is a chimeric monoclonal antibody of IgG1 subtype directed against CLDN18.2. IMAB362 recognizes the first extracellular domain of CLDN18.2 with high affinity and specificity and does not bind to any other claudin family member including the closely related splice variant 1 of Claudin 18 (CLDN18.1).

In human xenografts expressing CLDN18.2 survival benefit and tumor regressions have been observed in mice after administration of IMAB362. When administered intravenously in relevant animal species, no toxicity in gastric tissue is observed as the target epitope is not accessible. However, the tumor target becomes accessible for IMAB362 during malignant transformation. IMAB362 bundles four independent highly potent mechanisms of action: (i) antibody-dependent cellular cytotoxicity (ADCC), (ii) complement-dependent cytotoxicity (CDC), (iii) induction of apoptosis induced by cross linking of the target at the tumor surface and (iv) direct inhibition of proliferation.

A previous phase I trial has evaluated IMAB362 as monotherapy in a single dose in patients with late-stage gastroesophageal cancer. In this trial five IMAB362 doses (33, 100, 300, 600 and 1000 mg/m$^2$) were applied as monotherapy. This study shows that a single administration of this antibody is safe and well tolerated in a dosage of up to 1000 mg/m$^2$, as no relevant differences in AE profile and other safety parameters between the dose groups could be seen (AE=adverse event). Best results with regard to antitumoral activity were obtained for the 300 mg/m$^2$ and 600 mg/m$^2$ groups. In two patients of the 300 mg/m$^2$ group the disease was controlled and as they had only non-target lesions they were rated as non-CR, non-PD (CD=complete response; PD=progressive disease). The duration of non-CR, non-PD was about two months and six weeks, respectively. Tumor marker levels of these three patients remained stable. One patient in the 600 mg/m$^2$ group presented with stable disease (SD). The duration of the SD was about 2 months.

On basis of the highly potent mechanisms of action for the induced cell killing of IMAB362, the survival benefit of IMAB362-treated mice bearing a CLDN18.2-positive tumor, the absence of any indication for IMAB362-related toxicity, and the promising results of the phase I trial a phase IIa study was initialized. This phase IIa clinical trial was conducted to determine safety, tolerability and antitumoral activity of repetitive doses of IMAB362 in patients with metastatic, refractory or recurrent disease of advanced adenocarcinoma of the stomach or the lower esophagus proven by histology.

In this phase IIa trial the investigational drug was applied in three cohorts, which were recruited sequentially. A first cohort of three patients received repeated doses of IMAB362 at a lower dose level (300 mg/m$^2$ body surface area). The antibody was given as a 2 h intravenous infusion. Since no indication for IMAB362-related toxicity was detected in the first cohort, the IMAB362 dose of the second cohort (three patients) was increased to 600 mg/m$^2$ body surface area. In a third cohort 19 patients were allocated with the same dose (repetitive application of 600 mg/m$^2$ body surface area). Patient samples from this cohort were analyzed for several accompanying analytics i.e. ADCC, CDC, immunophenotyping and genetic immune polymorphisms.

All patients of all cohorts have received repeated doses of IMAB362 every two weeks on visits 2, 5, 6, 7 and 8 (5 applications).

The discrepancy of antigen positive tumors (overexpressing the target antigen to similar extent) with regard to responsiveness to intervention with therapeutic monoclonal antibodies such as IMAB362 suggests that there are additional factors which are associated with therapy outcome. This demands careful selection of patients who may have a benefit from antibody therapy.

Therefore, there is a need to develop a test to measure the eligibility of patients for antibody therapy. The present invention addresses this need by providing markers which are associated with favorable and unfavorable outcomes, respectively, in antibody therapy. Furthermore, the present invention demonstrates that these markers are useful as markers for prognosing clinical outcome for cancer patients.

The findings presented herein may be used to select a suitable treatment for a cancer patient and, in particular, to decide whether antibody therapy should be administered to a cancer patient.

SUMMARY OF THE INVENTION

The present invention provides methods of SNP (single-nucleotide polymorphism) genotyping, such as for use in evaluating an individual's likelihood of responding to a therapeutic treatment for cancer, in selecting a treatment or preventive regimen (e.g., in deciding whether or not to administer a particular therapeutic agent to an individual having cancer, or who is at increased risk for developing cancer in the future), or in evaluating an individual's prognosis for disease severity and recovery.

The present invention is based on the finding that certain genotypes for SNPs are associated with sensitivity/insensitivity of cancer towards antibody treatment such as treatment of CLDN18.2 positive cancer, in particular CLDN18.2 positive gastroesophageal cancer with IMAB362. The present invention is further based on the finding that certain genotypes for SNPs are associated with clinical outcome for cancer patients and thus are useful for prognosing cancer.

In one aspect, the invention relates to a method of assessing
  (i) if a cancer patient having a tumor antigen-positive tumor is a responder to treatment with an antibody against the tumor antigen, and/or
  (ii) if a cancer patient, preferably a cancer patient having a tumor antigen-positive tumor, will experience progression-free survival, said method comprising determining the genotype for one or more single-nucleotide polymorphisms selected from the group consisting of FCGR2A rs1801274, MUC1 rs4072037, IL-10 rs1800896, DNMT3A rs1550117, SMAD4 rs12456284, EGF rs4444903, CDH1 rs16260, ERCC1 rs11615, and FCGR3A rs396991 in a sample obtained from the patient.

In one embodiment, the presence of the heterozygous FCGR2A rs1801274 [CT] genotype indicates a reduced risk of a cancer patient not being a responder to treatment with the antibody and/or a reduced risk of a cancer patient not experiencing progression-free survival.

In one embodiment, the presence of the homozygous FCGR2A rs1801274 [TT] genotype and/or the homozygous FCGR2A rs1801274 [CC] genotype indicates an increased risk of a cancer patient not being a responder to treatment with the antibody and/or an increased risk of a cancer patient not experiencing progression-free survival.

In one embodiment, the presence of the homozygous MUC1 rs4072037 [AA] genotype indicates a reduced risk of a cancer patient not being a responder to treatment with the antibody and/or a reduced risk of a cancer patient not experiencing progression-free survival.

In one embodiment, the presence of the homozygous MUC1 rs4072037 [GG] genotype indicates an increased risk of a cancer patient not being a responder to treatment with the antibody and/or an increased risk of a cancer patient not experiencing progression-free survival.

In one embodiment, the presence of the homozygous IL-10 rs1800896 [GG] genotype indicates a reduced risk of a cancer patient not being a responder to treatment with the antibody and/or a reduced risk of a cancer patient not experiencing progression-free survival.

In one embodiment, the presence of the heterozygous DNMT3A rs1550117 [GA] genotype indicates a reduced risk of a cancer patient not being a responder to treatment with the antibody and/or a reduced risk of a cancer patient not experiencing progression-free survival.

In one embodiment, the presence of the heterozygous SMAD4 rs12456284 [GA] genotype indicates a reduced risk of a cancer patient not being a responder to treatment with the antibody and/or a reduced risk of a cancer patient not experiencing progression-free survival.

In one embodiment, the presence of the homozygous EGF rs4444903 [AA] genotype indicates a reduced risk of a cancer patient not being a responder to treatment with the antibody and/or a reduced risk of a cancer patient not experiencing progression-free survival.

In one embodiment, the presence of the homozygous CDH1 rs16260 [AA] genotype indicates a reduced risk of a cancer patient not being a responder to treatment with the antibody and/or a reduced risk of a cancer patient not experiencing progression-free survival.

In one embodiment, the presence of the homozygous ERCC1 rs11615 [TT] genotype indicates a reduced risk of a cancer patient not being a responder to treatment with the antibody and/or a reduced risk of a cancer patient not experiencing progression-free survival.

In one embodiment, the presence of the heterozygous FCGR3A rs396991 [TG] genotype and/or the homozygous FCGR3A rs396991 [TT] genotype indicates a reduced risk of a cancer patient not being a responder to treatment with the antibody and/or a reduced risk of a cancer patient not experiencing progression-free survival.

In one embodiment, the presence of the homozygous FCGR3A rs396991 [GG] genotype indicates an increased risk of a cancer patient not being a responder to treatment with the antibody and/or an increased risk of a cancer patient not experiencing progression-free survival.

In one embodiment, the tumor antigen is the CLDN18.2 protein.

In one aspect, the invention relates to a method of assessing
  (i) if a cancer patient having a CLDN18.2-positive tumor is a responder to treatment with an antibody against the CLDN18.2 protein, and/or
  (ii) if a cancer patient, preferably a cancer patient having a CLDN18.2-positive tumor, will experience progression-free survival,
  said method comprising determining the genotype for one or more single-nucleotide polymorphisms selected from the group consisting of FCGR2A rs1801274, MUC1 rs4072037, IL-10 rs1800896, DNMT3A rs1550117, SMAD4 rs12456284, EGF rs4444903, CDH1 rs16260, ERCC1 rs11615, and FCGR3A rs396991 in a sample obtained from the patient.

In one embodiment, the presence of the heterozygous FCGR2A rs1801274 [CT] genotype indicates a reduced risk of a cancer patient not being a responder to treatment with the antibody and/or a reduced risk of a cancer patient not experiencing progression-free survival.

In one embodiment, the presence of the homozygous FCGR2A rs1801274 [TT] genotype and/or the homozygous FCGR2A rs1801274 [CC] genotype indicates an increased risk of a cancer patient not being a responder to treatment with the antibody and/or an increased risk of a cancer patient not experiencing progression-free survival.

In one embodiment, the presence of the homozygous MUC1 rs4072037 [AA] genotype indicates a reduced risk of a cancer patient not being a responder to treatment with the antibody and/or a reduced risk of a cancer patient not experiencing progression-free survival.

In one embodiment, the presence of the homozygous MUC1 rs4072037 [GG] genotype indicates an increased risk of a cancer patient not being a responder to treatment with the antibody and/or an increased risk of a cancer patient not experiencing progression-free survival.

In one embodiment, the presence of the homozygous IL-10 rs1800896 [GG] genotype indicates a reduced risk of a cancer patient not being a responder to treatment with the antibody and/or a reduced risk of a cancer patient not experiencing progression-free survival.

In one embodiment, the presence of the heterozygous DNMT3A rs1550117 [GA] genotype indicates a reduced risk of a cancer patient not being a responder to treatment with the antibody and/or a reduced risk of a cancer patient not experiencing progression-free survival.

In one embodiment, the presence of the heterozygous SMAD4 rs12456284 [GA] genotype indicates a reduced risk of a cancer patient not being a responder to treatment with the antibody and/or a reduced risk of a cancer patient not experiencing progression-free survival.

In one embodiment, the presence of the homozygous EGF rs4444903 [AA] genotype indicates a reduced risk of a cancer patient not being a responder to treatment with the antibody and/or a reduced risk of a cancer patient not experiencing progression-free survival.

In one embodiment, the presence of the homozygous CDH1 rs16260 [AA] genotype indicates a reduced risk of a cancer patient not being a responder to treatment with the antibody and/or a reduced risk of a cancer patient not experiencing progression-free survival.

In one embodiment, the presence of the homozygous ERCC1 rs11615 [TT] genotype indicates a reduced risk of a cancer patient not being a responder to treatment with the antibody and/or a reduced risk of a cancer patient not experiencing progression-free survival.

In one embodiment, the presence of the heterozygous FCGR3A rs396991 [TG] genotype and/or the homozygous FCGR3A rs396991 [TT] genotype indicates a reduced risk of a cancer patient not being a responder to treatment with the antibody and/or a reduced risk of a cancer patient not experiencing progression-free survival.

In one embodiment, the presence of the homozygous FCGR3A rs396991 [GG] genotype indicates an increased risk of a cancer patient not being a responder to treatment with the antibody and/or an increased risk of a cancer patient not experiencing progression-free survival.

In one embodiment of all aspects of the invention, the antibody acts through recruiting the patient's immune system to destroy tumor cells. In one embodiment, the antibody acts through antibody-dependent cell-mediated cytotoxicity (ADCC) and/or complement-dependent cytotoxicity (CDC).

In one embodiment, the antibody is a monoclonal antibody. In one embodiment of all aspects of the invention, the antibody comprises a heavy chain comprising an amino acid sequence represented by SEQ ID NO: 17 or 51 or a fragment thereof and a light chain comprising an amino acid sequence represented by SEQ ID NO: 24 or a fragment thereof.

In one embodiment of all aspects of the invention, non-responsiveness to treatment with the antibody comprises a relative reduction in one or more of survival, progression-free survival, recurrence-free survival, distant recurrence-free survival, and stable disease.

In one aspect, the invention relates to a method of treating a cancer patient, said method comprising
a. assessing if the cancer patient is a responder to treatment with an antibody by the method of the invention and
b. (i) treating the cancer patient with an antibody if the patient has a reduced risk for not being a responder to treatment with the antibody or (ii) not treating the cancer patient with an antibody and/or treating the cancer patient with a treatment regimen which comprises a treatment which is different from a treatment with an antibody if the patient has an increased risk for not being a responder to treatment with the antibody.

In one embodiment, the treatment regimen comprises a treatment not being dependent on the immune system of the patient. In one embodiment, the treatment regimen does not comprise a treatment with an antibody acting through recruiting the patient's immune system to destroy tumor cells. In one embodiment, the treatment regimen comprises surgery, chemotherapy and/or radiation. In one embodiment, the treatment regimen comprises a treatment with a small molecule inhibitor of the tumor antigen and/or an antibody-drug conjugate wherein the antibody is directed against the tumor antigen. In one embodiment, the antibody-drug conjugate is an antibody coupled to a radioactive, chemotherapeutic or toxin moiety. In one embodiment, the antibody-drug conjugate is an antibody coupled to a cytostatic or cytotoxic compound.

In one aspect, the invention relates to a method of assessing the clinical outcome for a cancer patient, said method comprising determining the genotype for one or more single-nucleotide polymorphisms selected from the group consisting of FCGR2A rs1801274, MUC1 rs4072037, IL-10 rs1800896, DNMT3A rs1550117, SMAD4 rs12456284, EGF rs4444903, CDH1 rs16260, ERCC1 rs11615, and FCGR3A rs396991 in a sample obtained from the patient.

In one embodiment, the presence of the heterozygous FCGR2A rs1801274 [CT] genotype indicates a reduced risk of poor clinical outcome.

In one embodiment, the presence of the homozygous FCGR2A rs1801274 [TT] genotype and/or the homozygous FCGR2A rs1801274 [CC] genotype indicates an increased risk of poor clinical outcome.

In one embodiment, the presence of the homozygous MUC1 rs4072037 [AA] genotype indicates a reduced risk of poor clinical outcome.

In one embodiment, the presence of the homozygous MUC1 rs4072037 [GG] genotype indicates an increased risk of poor clinical outcome.

In one embodiment, the presence of the homozygous IL-10 rs1800896 [GG] genotype indicates a reduced risk of poor clinical outcome.

In one embodiment, the presence of the heterozygous DNMT3A rs1550117 [GA] genotype indicates a reduced risk of poor clinical outcome.

In one embodiment, the presence of the heterozygous SMAD4 rs12456284 [GA] genotype indicates a reduced risk of poor clinical outcome.

In one embodiment, the presence of the homozygous EGF rs4444903 [AA] genotype indicates a reduced risk of poor clinical outcome.

In one embodiment, the presence of the homozygous CDH1 rs16260 [AA] genotype indicates a reduced risk of poor clinical outcome.

In one embodiment, the presence of the homozygous ERCC1 rs11615 [TT] genotype indicates a reduced risk of poor clinical outcome.

In one embodiment, the presence of the heterozygous FCGR3A rs396991 [TG] genotype and/or the homozygous FCGR3A rs396991 [TT] genotype indicates a reduced risk of poor clinical outcome.

In one embodiment, the presence of the homozygous FCGR3A rs396991 [GG] genotype indicates an increased risk of poor clinical outcome.

In one embodiment, assessing the clinical outcome for a cancer patient comprises predicting the likelihood of one or more of survival, progression-free survival, recurrence-free survival, distant recurrence-free survival and stable disease. In one embodiment, poor clinical outcome comprises a relative reduction in one or more of survival, progression-free survival, recurrence-free survival, distant recurrence-free survival and stable disease.

In one embodiment, the patient has a tumor antigen-positive tumor and receives a treatment with an antibody against the tumor antigen.

In one embodiment of all aspects of the invention, the sample is a sample comprising DNA. In one embodiment, the DNA has been extracted from a bodily sample of the patient. In one embodiment, the DNA has been extracted from blood.

In one embodiment of all aspects of the invention, the tumor is a solid tumor. In one embodiment, the tumor is a gastroesophageal tumor. In one embodiment, the tumor is an advanced adenocarcinoma of the stomach or the lower esophagus. In one embodiment, the cancer is gastroesophageal cancer. In one embodiment, the cancer is an advanced adenocarcinoma of the stomach or the lower esophagus.

In a further aspect, the present invention relates to a kit comprising means for determining the genotype for one or more single-nucleotide polymorphisms selected from the group consisting of FCGR2A rs1801274, MUC1 rs4072037, IL-10 rs1800896, DNMT3A rs1550117, SMAD4 rs12456284, EGF rs4444903, CDH1 rs16260, ERCC1 rs11615, and FCGR3A rs396991 in a sample obtained from the patient. In one embodiment, said kit is useful for conducting the methods of all aspects of the present invention. In one embodiment, said kit further comprises a data carrier. In one preferred embodiment, said data carrier is an electronic or a non-electronic data carrier. In one embodiment, said data carrier comprises instructions on how to carry out the methods of all aspects of the invention.

Other objects, advantages and features of the present invention will become apparent from the following detailed description when considered in conjunction with the accompanying figures.

Assignment of SNP-specific genotypes to bar sections is indicated. Pat. Patient population, Co. Control population.

Figure 2:
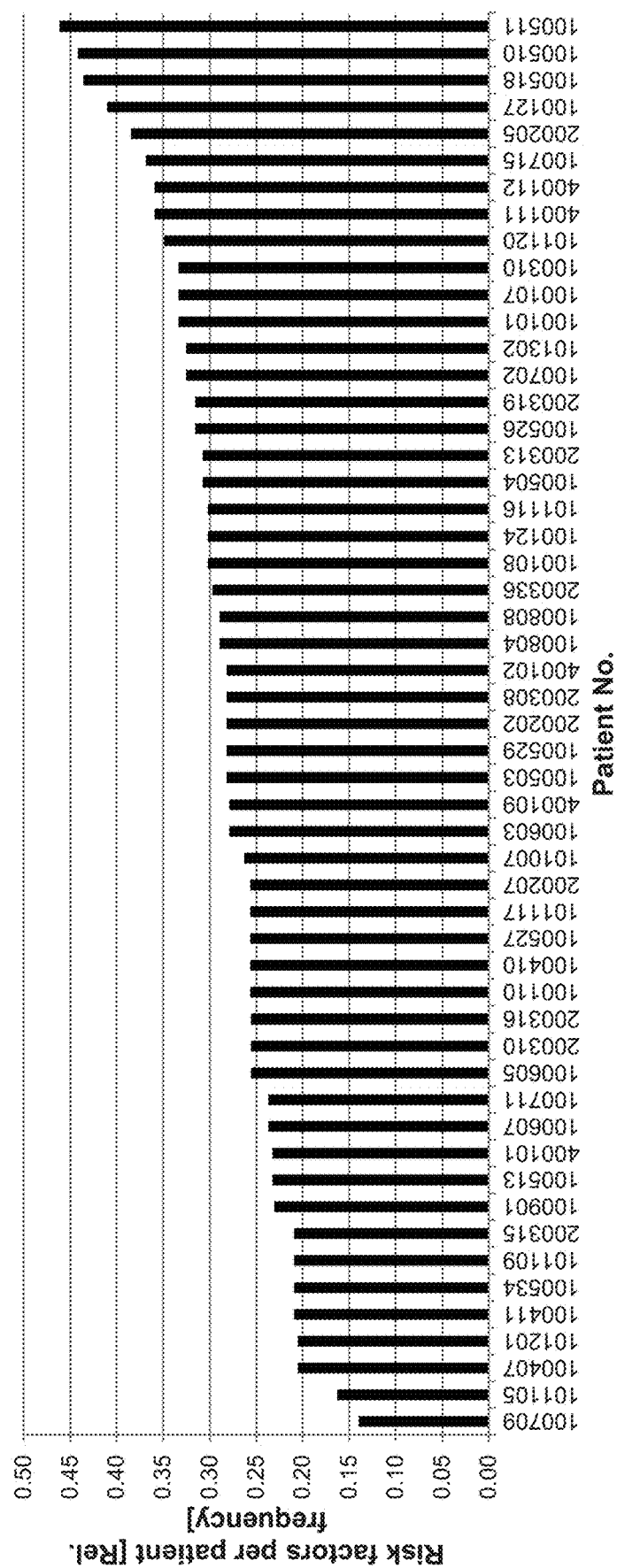

FIG. 2: Relative frequency of homozygous risk genotypes per patient in relation to the number of investigated SNP risk factors per patient. Patients are sorted by increasing frequency of accumulated homozygous risk factors.

Figure 3:
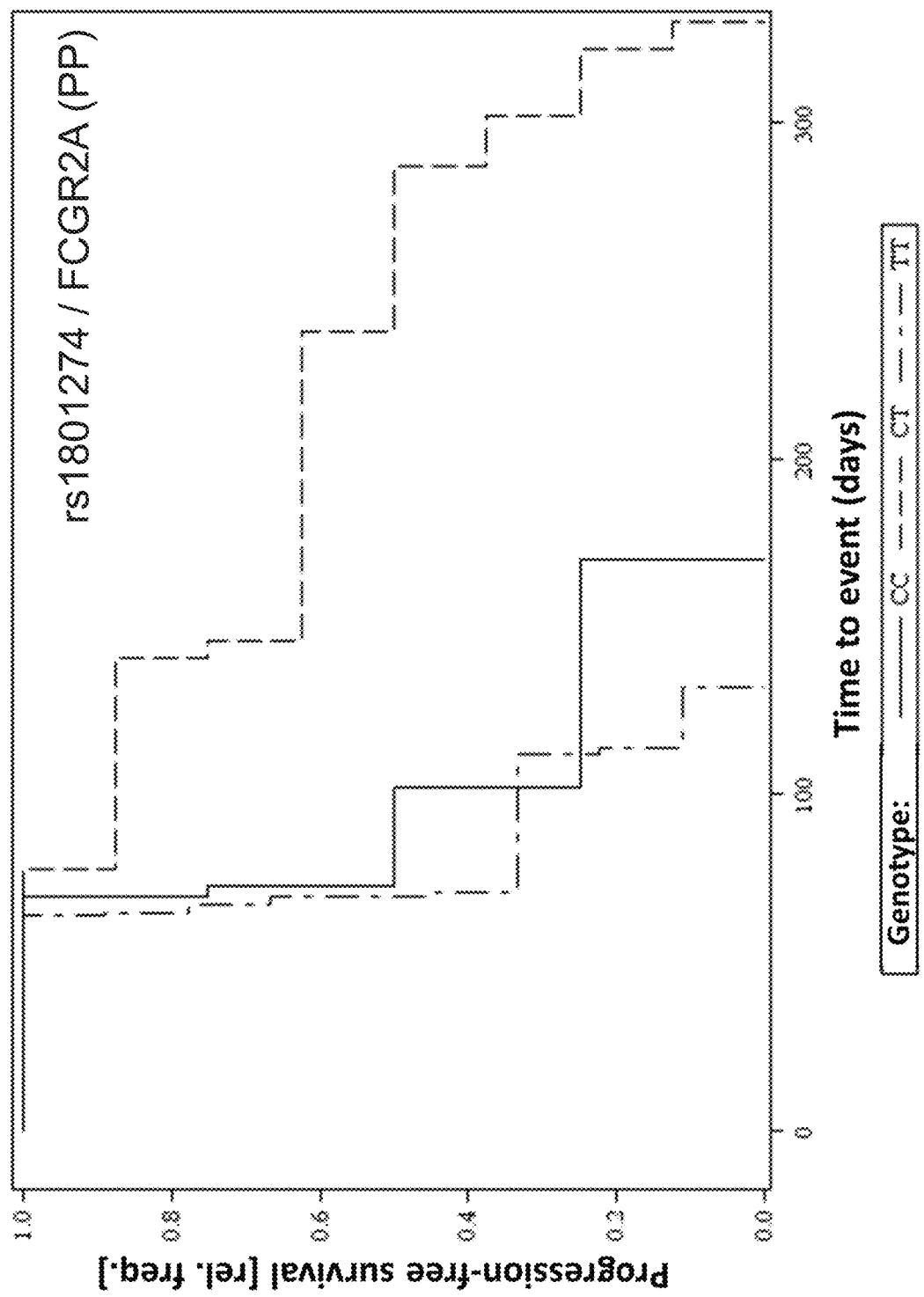

FIG. 3: Progression-free survival of PP patients differentiated by rs1801274 (FCGR2A) genotype (Kaplan-Meier curve)

Figure 4:
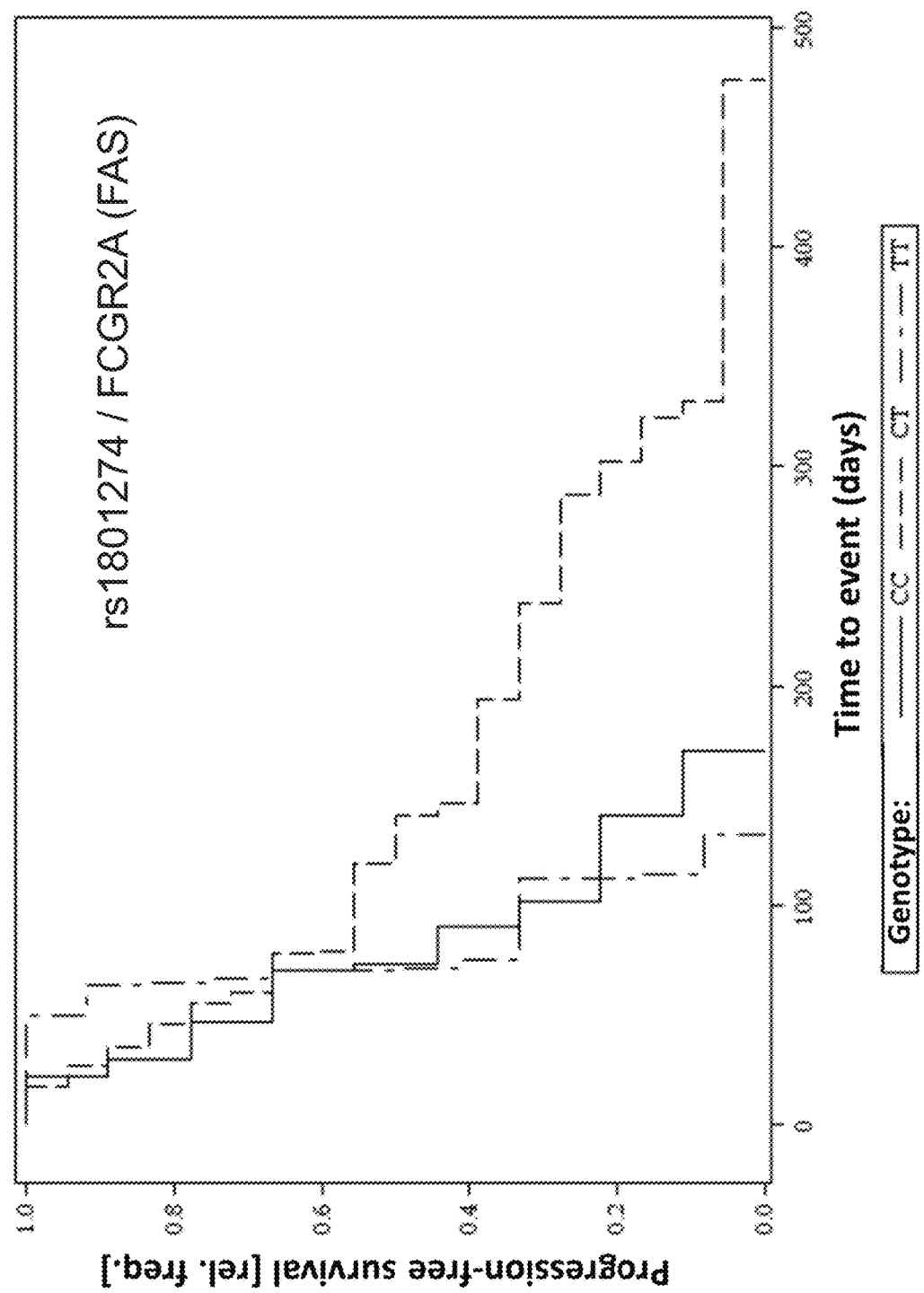

FIG. 4: Progression-free survival of FAS patients differentiated by rs1801274 (FCGR2A) genotype (Kaplan-Meier curve)

Figure 5:
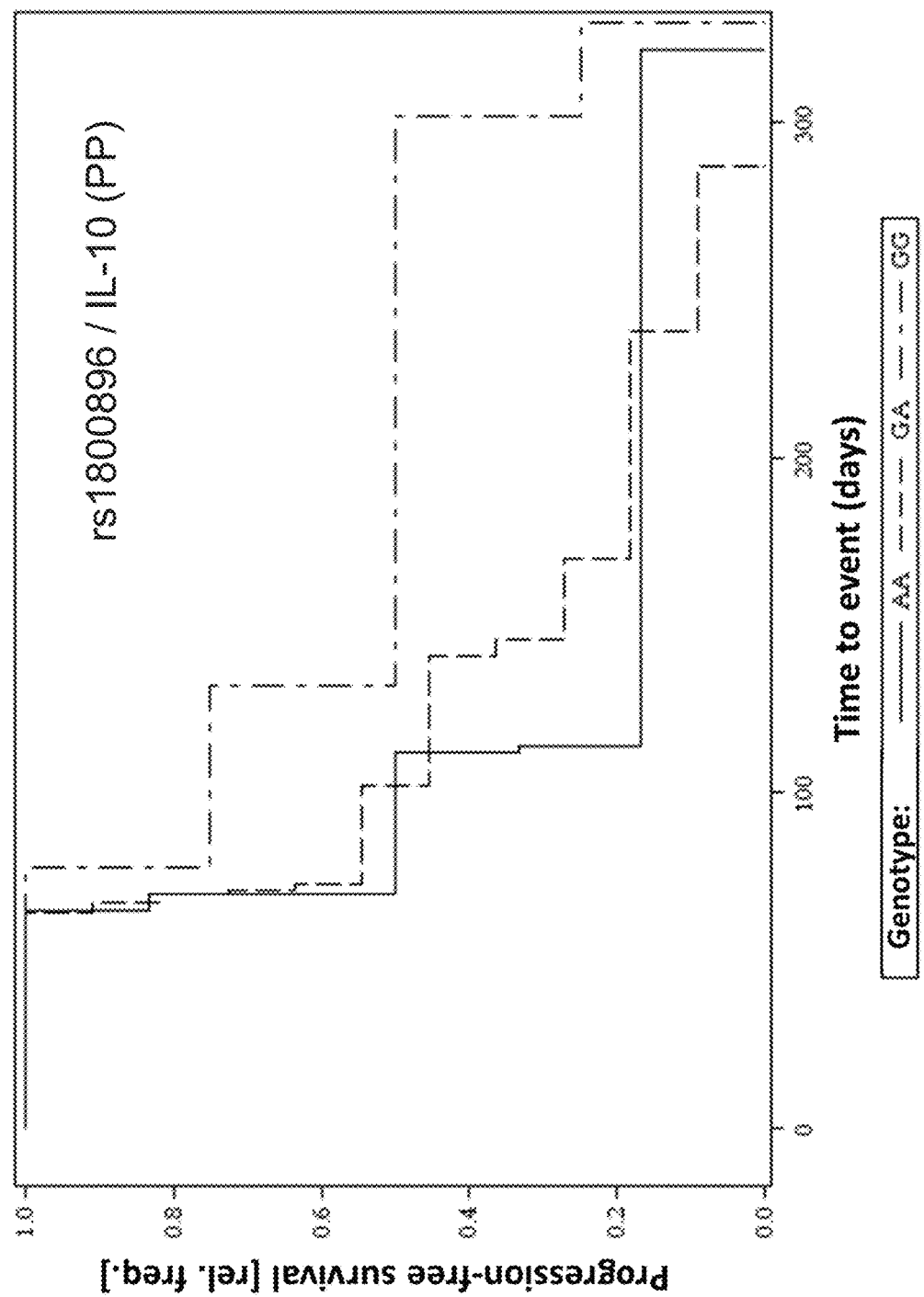

FIG. 5: Progression-free survival of PP patients differentiated by rs1800896 (IL-10) genotype (Kaplan-Meier curve)

Figure 6:
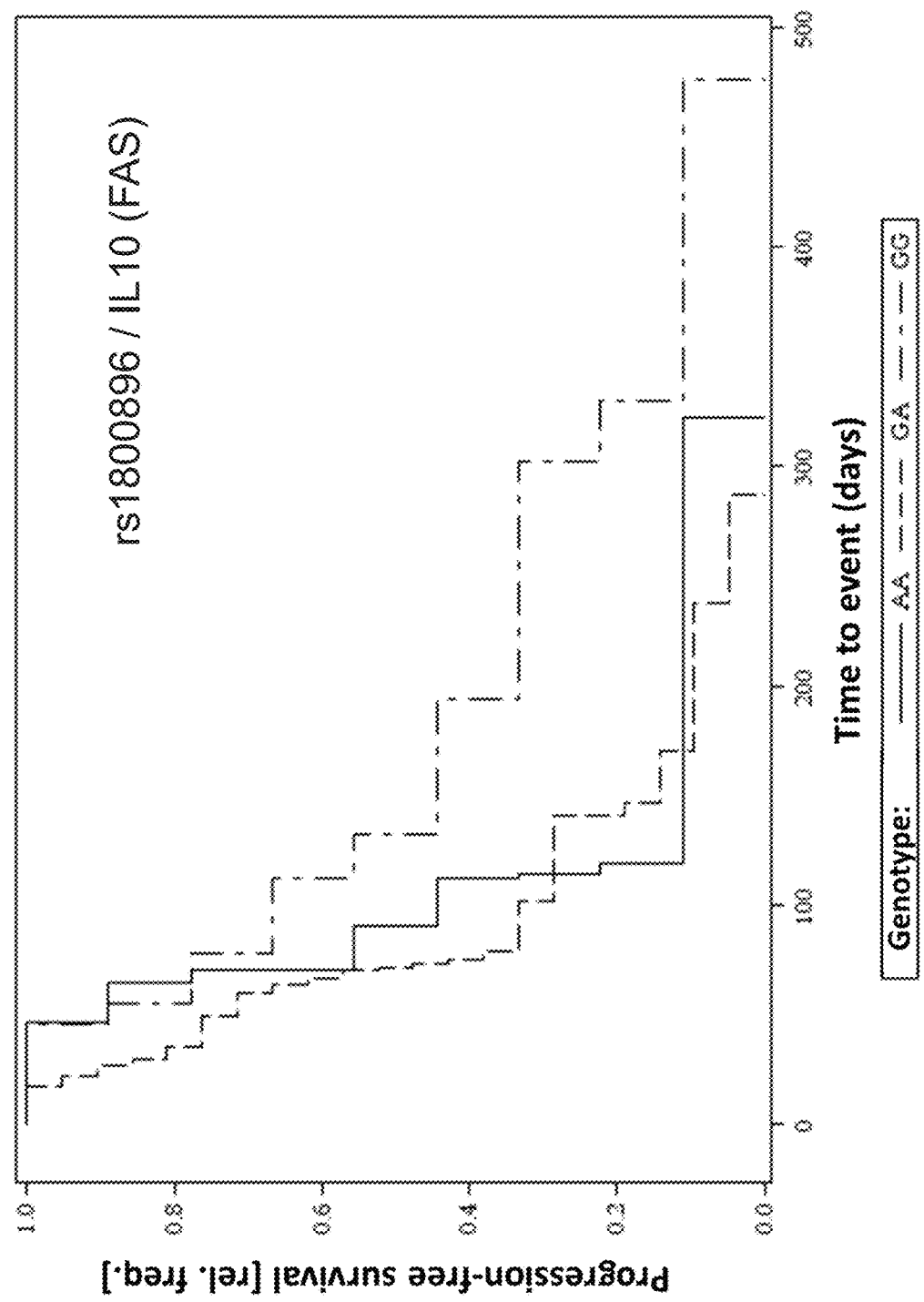

FIG. 6: Progression-free survival of FAS patients differentiated by rs1800896 (IL-10) genotype (Kaplan-Meier curve)

Figure 7:
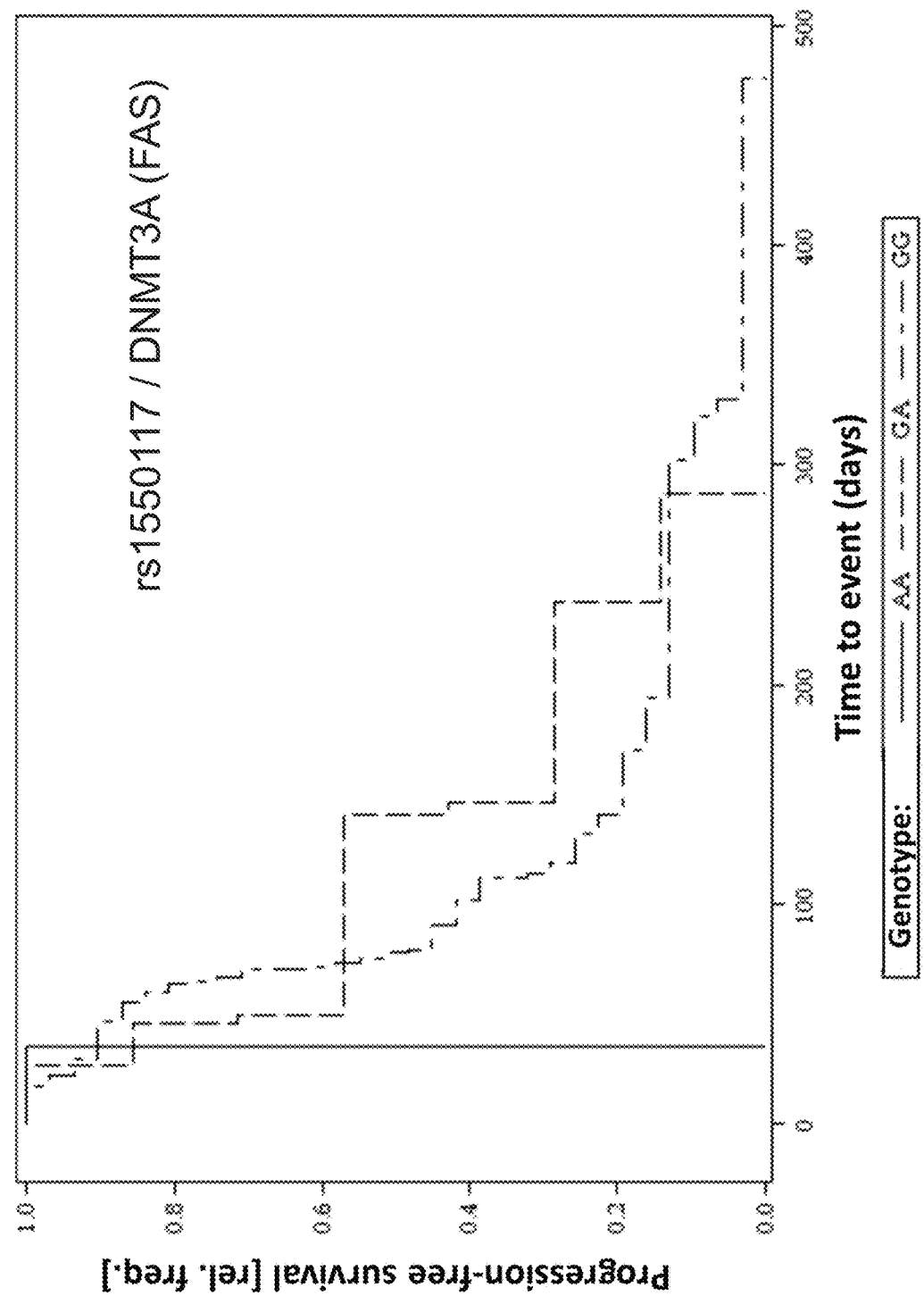

FIG. 7: Progression-free survival of FAS patients differentiated by rs1550117 (DNMT3A) genotype (Kaplan-Meier curve)

Figure 8:
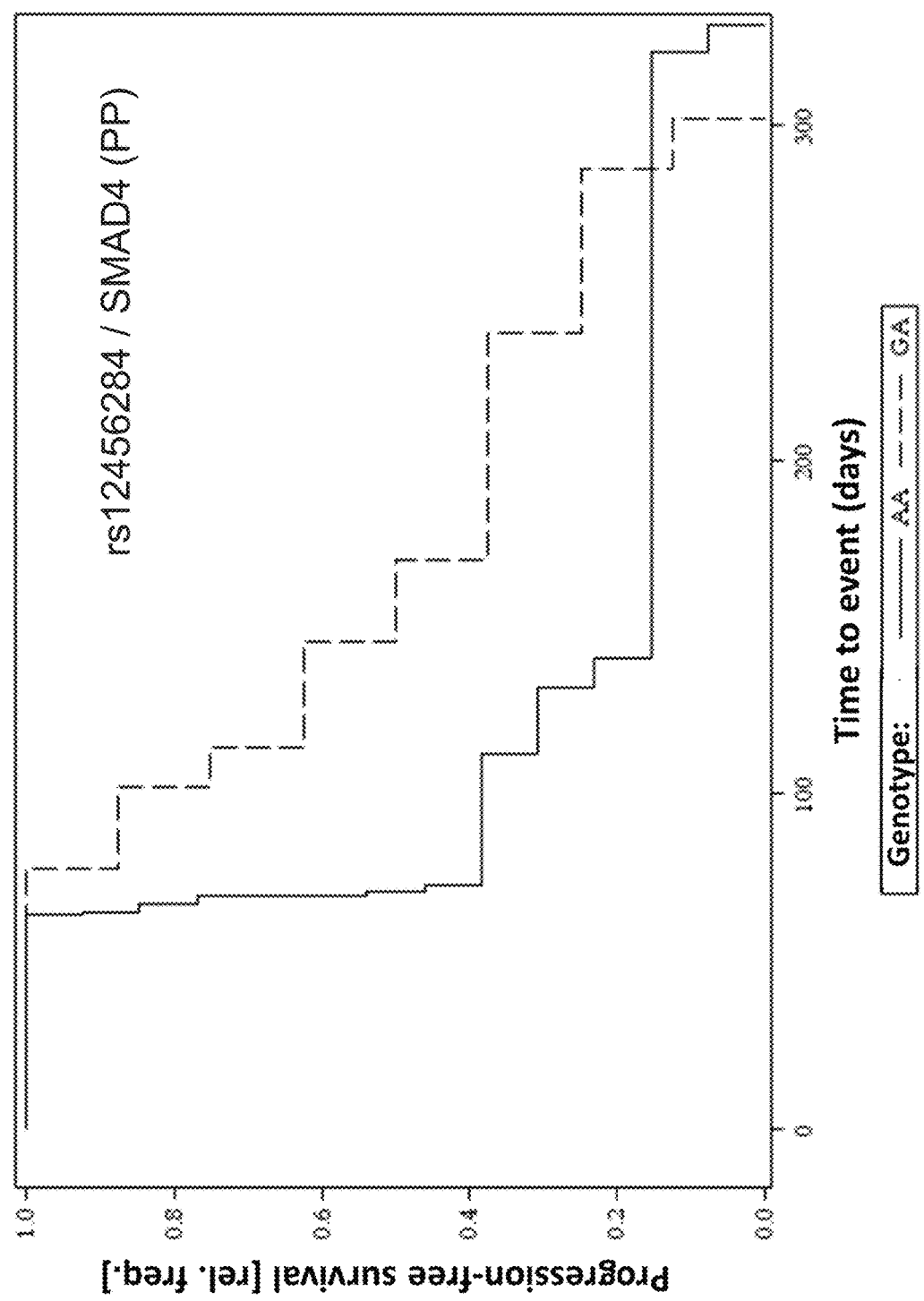

FIG. 8: Progression-free survival of PP patients differentiated by rs12456284 (SMAD4) genotype (Kaplan-Meier curve)

Figure 9:
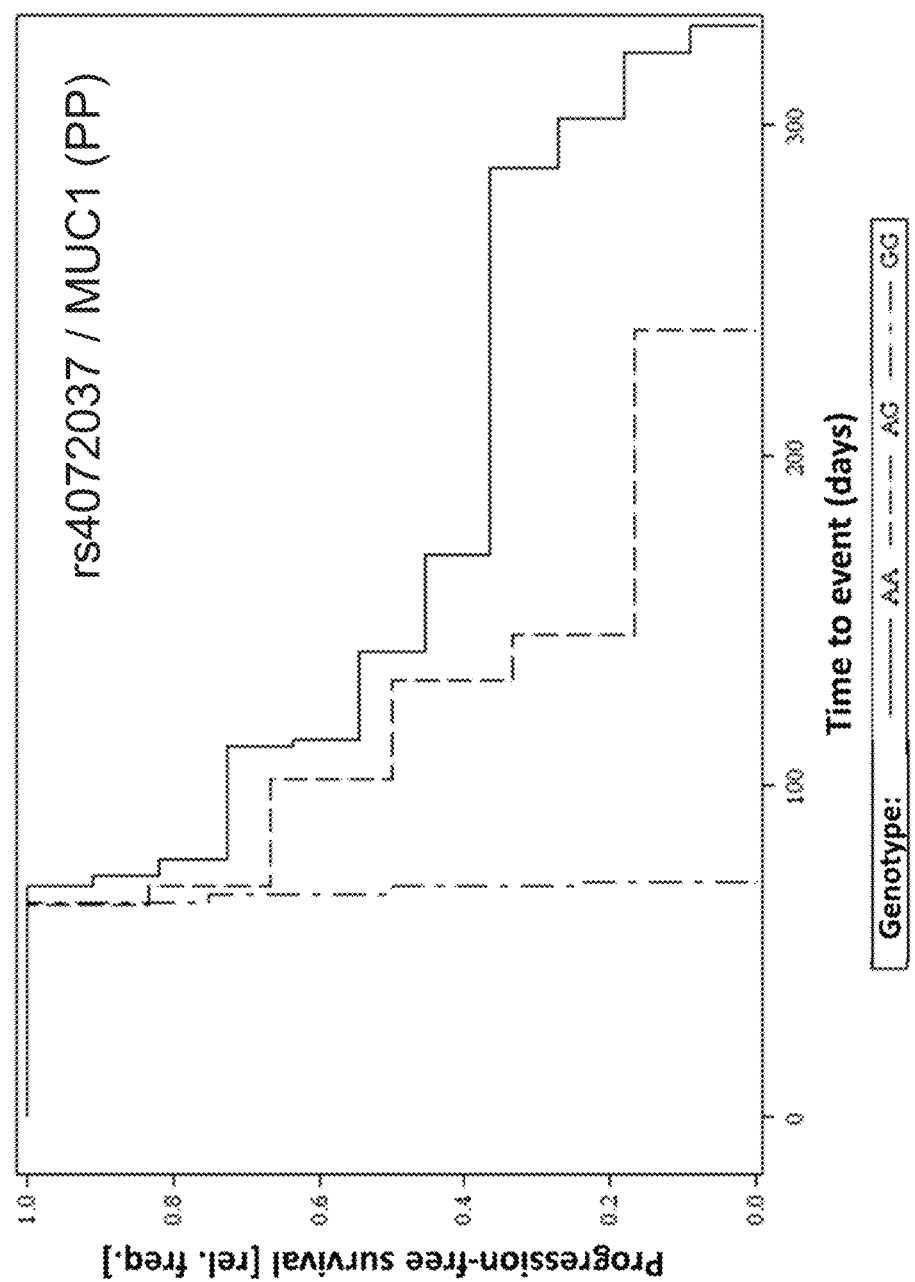

FIG. 9: Progression-free survival of PP patients differentiated by rs4072037 (MUC1) genotype (Kaplan-Meier curve)

Figure 10:
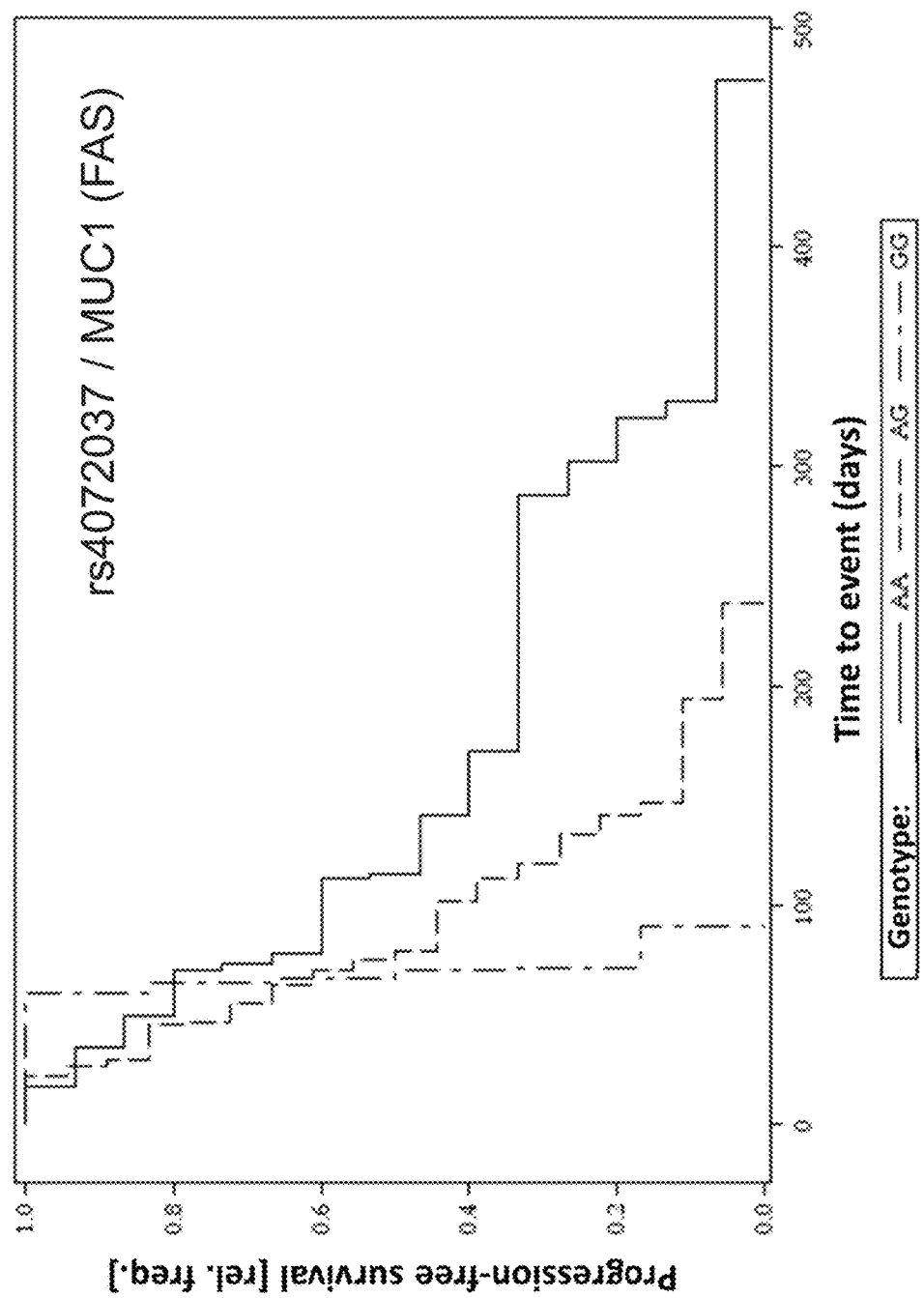

FIG. 10: Progression-free survival of FAS patients differentiated by rs4072037 (MUC1) genotype (Kaplan-Meier curve)

Figure 11:
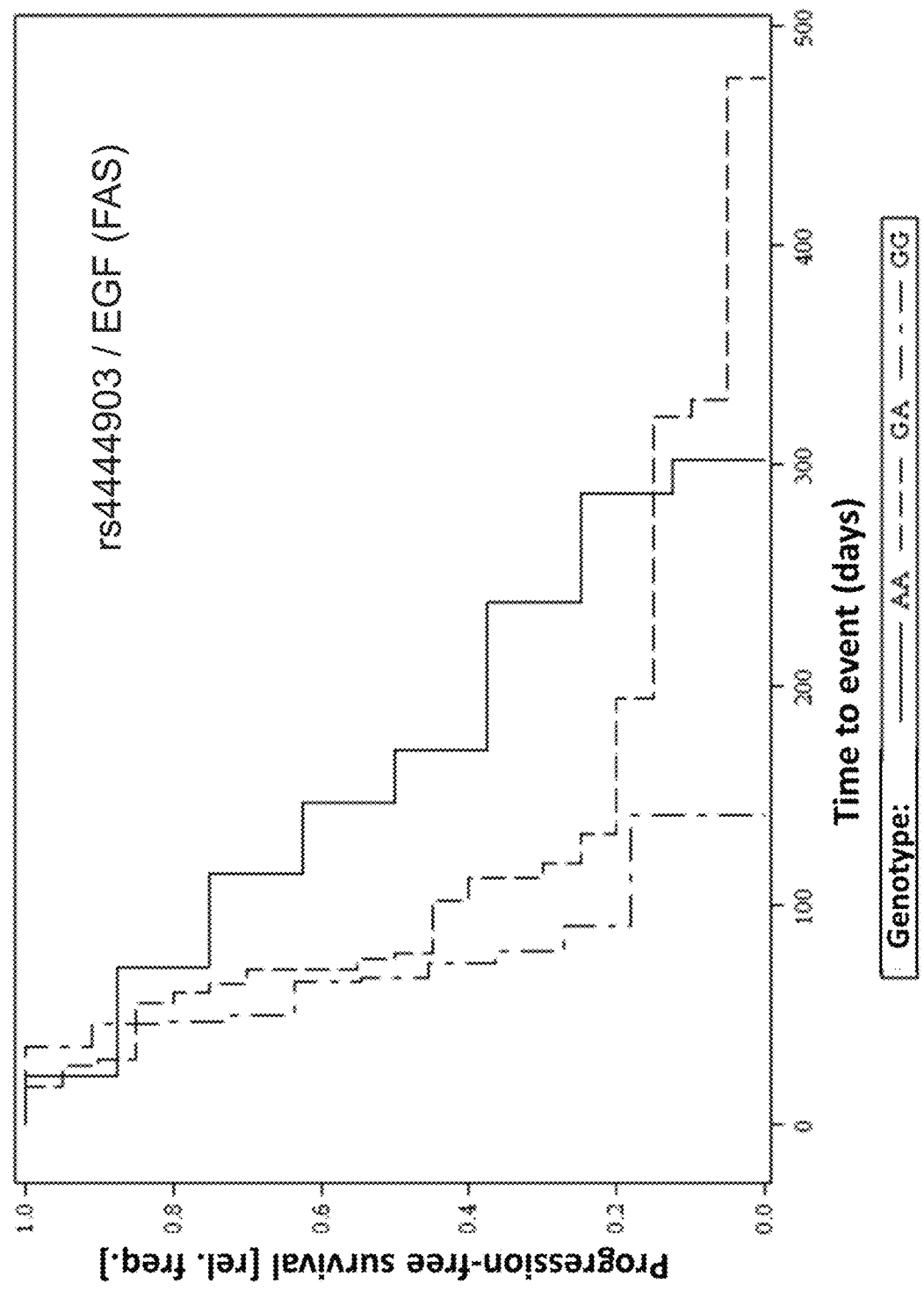

FIG. 11: Progression-free survival of FAS patients differentiated by rs4444903 (EGF) genotype (Kaplan-Meier curve)

Figure 12:
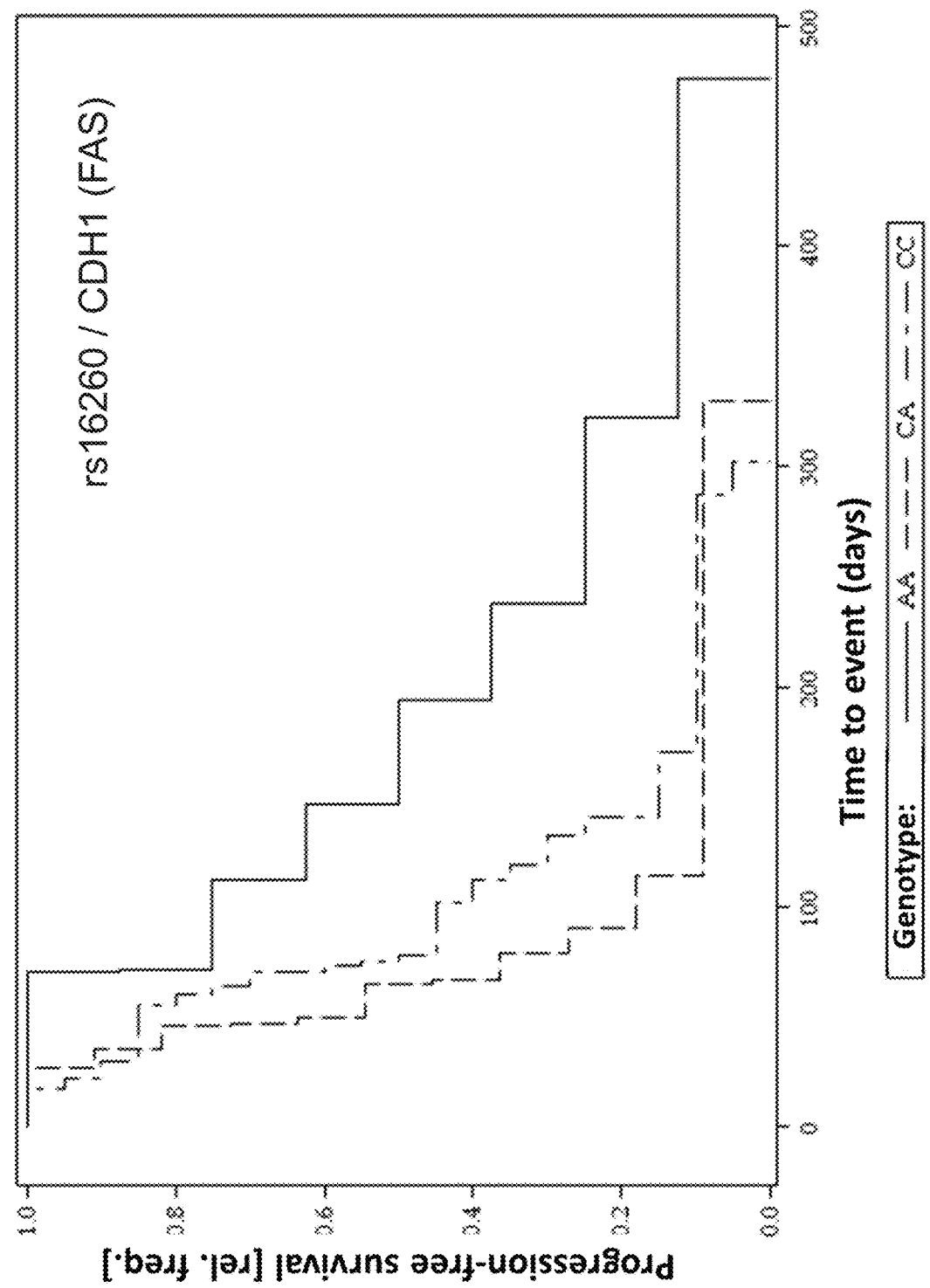

FIG. 12: Progression-free survival of FAS patients differentiated by rs16260 (CDH1) genotype (Kaplan-Meier curve)

Figure 13:
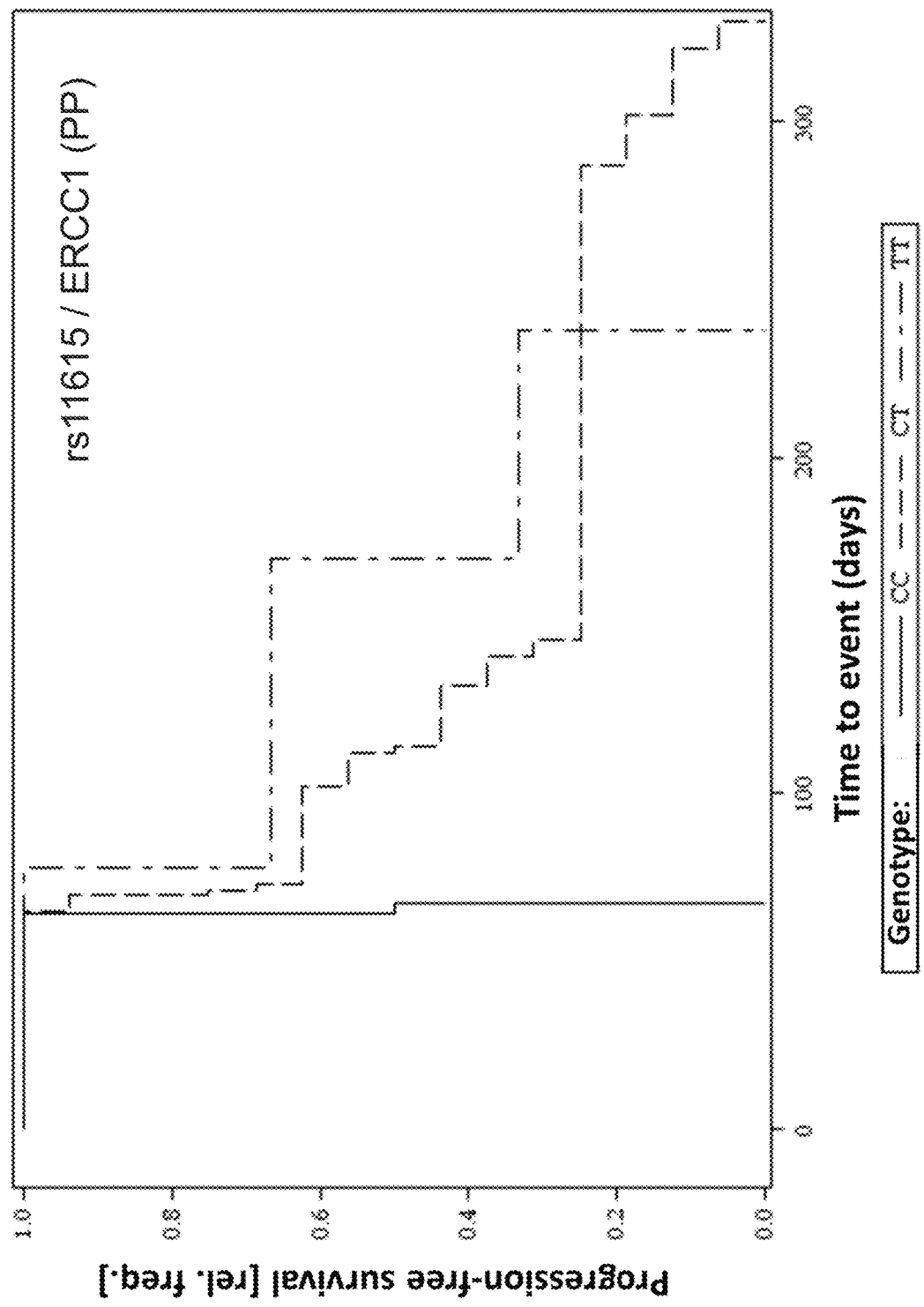

FIG. 13: Progression-free survival of PP patients differentiated by rs11615 (ERCC1) genotype (Kaplan-Meier curve)

Figure 14:
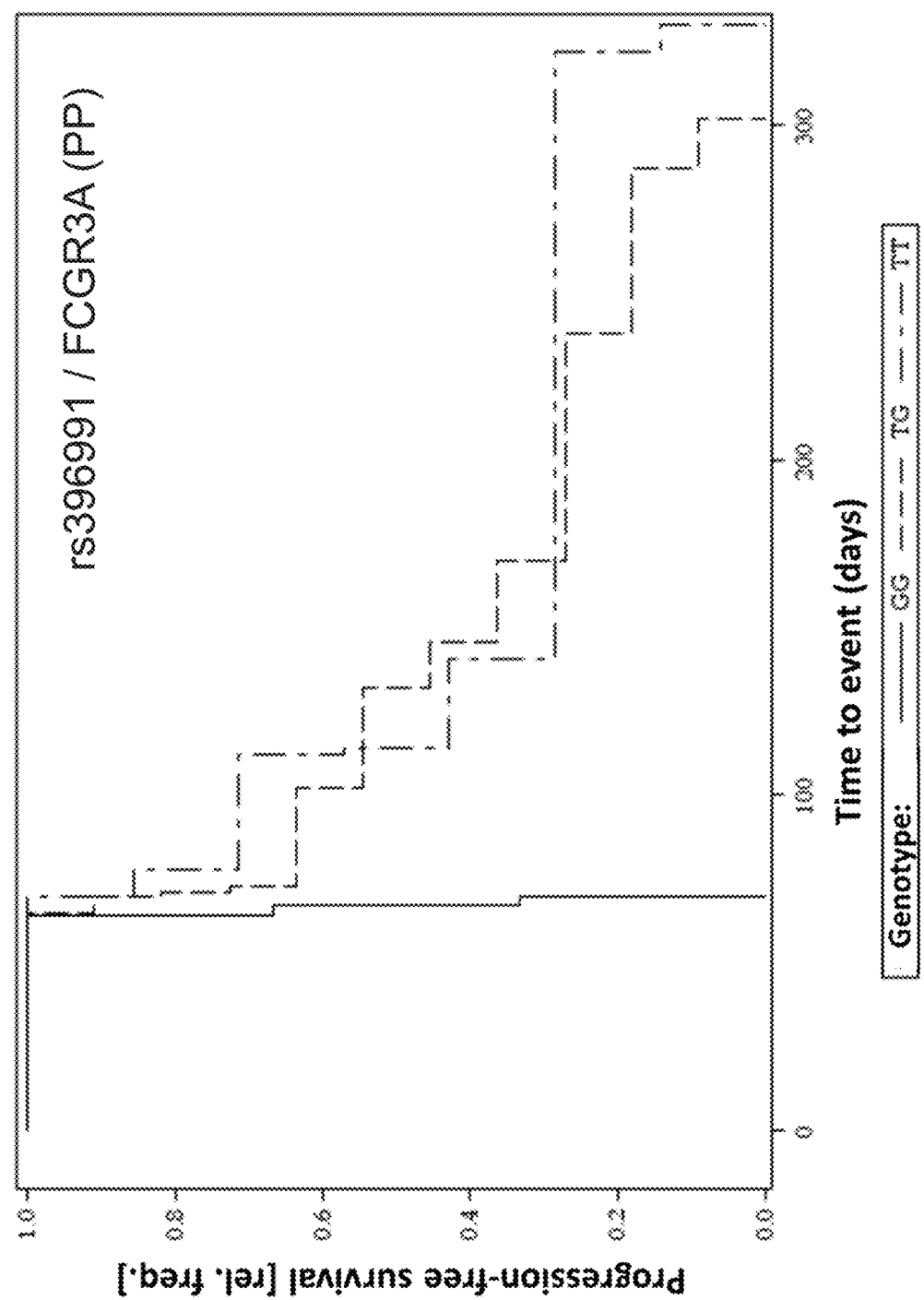

FIG. 14: Progression-free survival of PP patients differentiated by rs396991 (FCGR3A) genotype (Kaplan-Meier curve)

FIG. 15: an indication relating to deposited microorganism or other biological material for Accession Number DSM ACC2737.

FIG. 16: identification of further deposits having Accession Numbers DSM ACC2738, DSM ACC2739, DSM ACC2740, DSM ACC2741, DSM ACC2742, DSM ACC2743, DSM ACC2745, DSM ACC2746, DSM ACC2747, DSM ACC2748, DSM ACC2808, DSM ACC2809, and DSM2810.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present inventors provide tests to measure the eligibility of patients for certain cancer treatments, in particular antibody therapy, and to draw conclusions on the prognosis of a cancer patient. The results obtained using these tests enables the physician to decide on a suitable treatment for a cancer patient, and, in particular, to decide whether antibody therapy should be administered to a particular cancer patient.

The term "Single Nucleotide Polymorphism" or "SNP" relates to a DNA sequence variation occurring commonly within a population in which a single nucleotide in the genome (or other shared sequence) differs between members of a biological species or paired chromosomes. SNPs may occur in coding sequences of genes, non-coding regions of genes, or in intergenic regions (regions between genes). SNPs within a coding sequence may but do not necessarily change the amino acid sequence of the protein that is produced, due to degeneracy of the genetic code. Thus, SNPs in the coding region are of two types, synonymous and nonsynonymous SNPs. Synonymous SNPs do not affect the protein sequence while nonsynonymous SNPs change the amino acid sequence of protein. The nonsynonymous SNPs are of two types: missense and nonsense. SNPs that are not in protein-coding regions may still affect gene splicing, transcription factor binding, messenger RNA degradation, or the sequence of non-coding RNA. Gene expression affected by this type of SNP is referred to as an eSNP (expression SNP) and may be upstream or downstream from the gene.

Various methods known in the art can be used to determine the genotype for SNPs. Analytical methods to discover novel SNPs and detect known SNPs include, for example, DNA sequencing, capillary electrophoresis, mass spectrometry, single-strand conformation polymorphism (SSCP), electrochemical analysis, denaturating HPLC and gel electrophoresis, restriction fragment length polymorphism and hybridization analysis.

The process of determining which nucleotide is present at a particular SNP position described herein, for either or both alleles, can be referred to by such phrases as "determining the genotype for a SNP" or "SNP genotyping". Thus, these phrases can refer to detecting a single allele (nucleotide) at a SNP position or can encompass detecting both alleles (nucleotides) at a SNP position (such as to determine the homozygous or heterozygous state of a SNP position). Furthermore, these phrases may also refer to detecting an amino acid residue encoded by a SNP (such as alternative amino acid residues that are encoded by different codons created by alternative nucleotides at a SNP position).

A reagent that specifically detects a specific target SNP position disclosed herein, and that is preferably specific for a particular nucleotide (allele) of the target SNP position (i.e., the reagent preferably can differentiate between different alternative nucleotides at a target SNP position, thereby allowing the identity of the nucleotide present at the target SNP position to be determined) can be used for SNP detection. Typically, such detection reagent hybridizes to a target SNP-containing nucleic acid molecule by complementary base-pairing in a sequence specific manner, and discriminates the target variant sequence from other nucleic acid sequences such as an art-known form in a test sample. An example of a detection reagent is a non-naturally occurring nucleic acid primer or probe that hybridizes to a target nucleic acid containing a SNP disclosed herein. In a preferred embodiment, such a primer or probe can differentiate between nucleic acids having a particular nucleotide (allele) at the target SNP position from other nucleic acids that have a different nucleotide at the same target SNP position. In addition, a detection reagent may hybridize to a specific region 5' and/or 3' to the SNP position. It will be apparent to one of skill in the art that such detections reagents, such as such primers and probes are directly useful as reagents for genotyping one or more of the SNPs disclosed herein, and can be incorporated into any kit format.

For analyzing SNPs, it can be appropriate to use oligonucleotides specific for alternative SNP alleles. Such oligonucleotides that detect single nucleotide variations in target sequences may be referred to by such terms as "allele-specific oligonucleotides", "allele-specific probes", or "allele-specific primers".

A SNP detection reagent may be labeled with a reporter such as a fluorogenic reporter dye that emits a detectable signal. While the preferred reporter dye is a fluorescent dye, any reporter dye that can be attached to a detection reagent such as an oligonucleotide probe or primer is suitable according to the invention. In yet another embodiment, the detection reagent may be further labeled with a quencher dye, especially when the reagent is used as a self-quenching probe such as a TaqMan probe. The SNP detection reagents disclosed herein may also contain other labels, including but not limited to, biotin for streptavidin binding, hapten for antibody binding, and oligonucleotide for binding to another complementary oligonucleotide.

According to the present invention also reagents are contemplated that do not contain (or that are not complementary to) a SNP nucleotide to be identified but that are used to assay one or more SNPs disclosed herein. For example, primers that flank, but do not hybridize directly to a target SNP position are useful in primer extension reactions in which the primers hybridize to a region adjacent to the target SNP position (i.e., within one or more nucleotides from the target SNP site). During the primer extension reaction, a primer is typically not able to extend past a target SNP site if a particular nucleotide (allele) is present at that target SNP site, and the primer extension product can be detected in order to determine which SNP allele is present at the target SNP site. For example, particular ddNTPs are typically used in the primer extension reaction to terminate primer extension once a ddNTP is incorporated into the extension product. Thus, reagents that bind to a nucleic acid molecule in a region adjacent to a SNP site and that are used for assaying the SNP site, even though the bound sequences do not necessarily include the SNP site itself, are also contemplated according to the invention.

The term "FCGR2A" relates to the human FCGR2A gene. This gene encodes low affinity immunoglobulin gamma Fc region receptor II-a (CD32) and is one member of a family of immunoglobulin Fc receptor genes. The protein encoded by this gene is a cell surface receptor found on phagocytic cells such as macrophages and neutrophils, and is involved in the process of phagocytosis and clearing of immune complexes. Alternative splicing results in multiple transcript variants.

Preferably, the term "FCGR2A" relates to a nucleic acid comprising, preferably consisting of the nucleic acid sequence of SEQ ID NO: 61 of the sequence listing or a variant of said nucleic acid sequence and to a protein encoded by this nucleic acid, preferably to a protein comprising, preferably consisting of the amino acid sequence of SEQ ID NO: 62 of the sequence listing or a variant of said amino acid sequence.

rs1801274 is a SNP in the FCGR2A gene. rs1801274 (C) encodes the arginine (R) allele, with the (T) allele encoding the variant histidine (H). This SNP is an intragenic transition substitution with the following codon change: CAT,CGT and results in a missense mutation. The SNP is known in the literature by many names, including A519C and R131H. The context sequence is as follows:

TGGGATGGAGAAGGTGGGATCCAAA[C/T]GG-GAGAATTTCTGGGATTTTCCATT

The term "MUC1" relates to the human MUC1 gene. This gene encodes Mucin 1, cell surface associated (MUC1) or polymorphic epithelial mucin (PEM) which is a member of the mucin family and is a membrane bound, glycosylated phosphoprotein. The protein is anchored to the apical surface of many epithelia by a transmembrane domain. Beyond the transmembrane domain is a SEA domain that contains a cleavage site for release of the large extracellular domain. The protein serves a protective function by binding to pathogens and also functions in a cell signaling capacity.

Preferably, the term "MUC1" relates to a nucleic acid comprising, preferably consisting of the nucleic acid sequence of SEQ ID NO: 63 of the sequence listing or a variant of said nucleic acid sequence and to a protein encoded by this nucleic acid, preferably to a protein comprising, preferably consisting of the amino acid sequence of SEQ ID NO: 64 of the sequence listing or a variant of said amino acid sequence.

rs4072037 is a SNP in the MUC1 gene. This SNP is an intragenic transition substitution with the following codon change: ACA,ACG and results in a silent mutation. The context sequence is as follows:

CCCCTAAACCCGCAACAGTTGTTAC[A/G]GGTTCTGGTCATGCAAGCT

CTACCC

The term "IL-10" relates to the human IL-10 gene. This gene encodes interleukin-10 (IL-10), also known as human cytokine synthesis inhibitory factor (CSIF), which is an anti-inflammatory cytokine.

Preferably, the term "IL-10" relates to a nucleic acid comprising, preferably consisting of the nucleic acid sequence of SEQ ID NO: 65 of the sequence listing or a variant of said nucleic acid sequence and to a protein encoded by this nucleic acid, preferably to a protein comprising, preferably consisting of the amino acid sequence of SEQ ID NO: 66 of the sequence listing or a variant of said amino acid sequence.

rs1800896 is a SNP in the IL-10 gene. This SNP is an intergenic/unknown intragenic transition substitution. The context sequence is as follows:

CAACACTACTAAGGCTTCTTTGGGA[A/G]GGGGAAGTAGGGATAGGTA

AGAGGA

The term "DNMT3A" relates to the human DNMT3A gene. This gene encodes DNA (cytosine-5)-methyltransferase 3A. The protein encoded by this gene is an enzyme that catalyzes the transfer of methyl groups to specific CpG structures in DNA.

Preferably, the term "DNMT3A" relates to a nucleic acid comprising, preferably consisting of the nucleic acid sequence of SEQ ID NO: 67 of the sequence listing or a variant of said nucleic acid sequence and to a protein encoded by this nucleic acid, preferably to a protein comprising, preferably consisting of the amino acid sequence of SEQ ID NO: 68 of the sequence listing or a variant of said amino acid sequence.

rs1550117 is a SNP in the DNMT3A gene. This SNP is an intragenic transition substitution in the DNMT3A promoter region. The context sequence is as follows:

AATTCCACCAGCACAGCCACTCACT[A/G]TGTGCTCATCTCACTCCTC

CAGCAG

The term "SMAD4" relates to the human SMAD4 gene. This gene encodes Mothers against decapentaplegic homolog 4. The protein encoded by this gene is involved in cell signaling and belongs to the Darfwin family of proteins that modulate members of the TGFβ protein superfamily.

It binds receptor-regulated SMADs such as SMAD1 and SMAD2, and forms a complex that binds to DNA and serves as a transcription factor. It is the only known mammalian coSMAD.

Preferably, the term "SMAD4" relates to a nucleic acid comprising, preferably consisting of the nucleic acid sequence of SEQ ID NO: 69 of the sequence listing or a variant of said nucleic acid sequence and to a protein encoded by this nucleic acid, preferably to a protein comprising, preferably consisting of the amino acid sequence of SEQ ID NO: 70 of the sequence listing or a variant of said amino acid sequence.

rs12456284 is a SNP in the SMAD4 gene. This SNP is an intragenic transition substitution in the 3'-UTR. The context sequence is as follows:

AGGTCCAGAGCCAGTGTTCTTGTTC[A/G]ACCTGAAAGTAATGGCTCT

GGGTTG

The term "EGF" relates to the human EGF gene. This gene encodes epidermal growth factor. EGF is a growth factor that stimulates cell growth, proliferation, and differentiation by binding to its receptor EGFR.

Preferably, the term "EGF" relates to a nucleic acid comprising, preferably consisting of the nucleic acid sequence of SEQ ID NO: 71 of the sequence listing or a variant of said nucleic acid sequence and to a protein encoded by this nucleic acid, preferably to a protein comprising, preferably consisting of the amino acid sequence of SEQ ID NO: 72 of the sequence listing or a variant of said amino acid sequence.

rs4444903 is a SNP in the EGF gene. This SNP is an intragenic transition substitution in the 5'-UTR. The context sequence is as follows:

CTTTCAGCCCCAATCCAAGGGTTGT[A/G]GCTGGAACTTTCCATCAGT

TCTTCC

The term "CDH1" relates to the human CDH1 gene. This gene encodes cadherin-1 also known as CAM 120/80 or epithelial cadherin (E-cadherin) or uvomorulin. The protein is a classical member of the cadherin superfamily. It is a calcium-dependent cell-cell adhesion glycoprotein composed of five extracellular cadherin repeats, a transmembrane region, and a highly conserved cytoplasmic tail. Loss of function is thought to contribute to progression in cancer by increasing proliferation, invasion, and/or metastasis.

Preferably, the term "CDH1" relates to a nucleic acid comprising, preferably consisting of the nucleic acid sequence of SEQ ID NO: 73 of the sequence listing or a variant of said nucleic acid sequence and to a protein encoded by this nucleic acid, preferably to a protein comprising, preferably consisting of the amino acid sequence of SEQ ID NO: 74 of the sequence listing or a variant of said amino acid sequence.

rs16260 is a SNP in the CDH1 gene. This SNP is an intragenic transversion substitution located in the promoter region of the CDH1 gene. The context sequence is as follows:

CTAGCAACTCCAGGCTAGAGGGTCA[A/C]CGCGTCTATGCGAGGCCGG

GTGGGC

The term "ERCC1" relates to the human ERCC1 gene. This gene encodes DNA excision repair protein ERCC-1. The function of the ERCC1 protein is predominantly in nucleotide excision repair of damaged DNA.

Preferably, the term "ERCC1" relates to a nucleic acid comprising, preferably consisting of the nucleic acid sequence of SEQ ID NO: 75 of the sequence listing or a variant of said nucleic acid sequence and to a protein encoded by this nucleic acid, preferably to a protein comprising, preferably consisting of the amino acid sequence of SEQ ID NO: 76 of the sequence listing or a variant of said amino acid sequence.

rs11615 is a SNP in the ERCC1 gene. This SNP is a silent intragenic transition substitution. The context sequence is as follows:

ATCCCGTACTGAAGTTCGTGCGCAA[C/T]GTGCCCTGGGAATTTGGCG

ACGTAA

The term "FCGR3A" relates to the human FCGR3A gene. This gene encodes low affinity immunoglobulin gamma Fc region receptor III-A. The protein encoded by this gene is part of the cluster of differentiation cell surface molecules.

Preferably, the term "FCGR3A" relates to a nucleic acid comprising, preferably consisting of the nucleic acid sequence of SEQ ID NO: 77 of the sequence listing or a variant of said nucleic acid sequence and to a protein encoded by this nucleic acid, preferably to a protein comprising, preferably consisting of the amino acid sequence of SEQ ID NO: 78 of the sequence listing or a variant of said amino acid sequence.

rs396991 is a SNP in the FCGR3A gene. This SNP is an intragenic transversion substitution with the following codon change: GTT,TTT and results in a missense mutation. rs396991 (T) encodes the phenylalanine (F) allele, with the (G) allele encoding the variant valine (V). The context sequence is as follows:

CGGCTCCTACTTCTGCAGGGGGCTT[G/T]TTGGGAGTAAAAATGTGTC

TTCAGA

Claudins are a family of proteins that are the most important components of tight junctions, where they establish the paracellular barrier that controls the flow of molecules in the intercellular space between cells of an epithelium. Claudins are transmembrane proteins spanning the membrane 4 times with the N-terminal and the C-terminal end both located in the cytoplasm. The first extracellular loop or domain consists on average of 53 amino acids, and the second extracellular loop or domain consists of around 24 amino acids. Cell surface proteins of the claudin family, such as CLDN18.2, are expressed in tumors of various origins, and are particularly suited as target structures in connection with antibody-mediated cancer immunotherapy due to their selective expression (no expression in a toxicity relevant normal tissue) and localization to the plasma membrane.

The term "CLDN" as used herein means claudin and includes CLDN18.2. Preferably, a claudin is a human claudin.

The term "CLDN18" relates to claudin 18 and includes any variants, including claudin 18 splice variant 1 (claudin 18.1 (CLDN18.1)) and claudin 18 splice variant 2 (claudin 18.2 (CLDN18.2)).

The term "CLDN18.2" preferably relates to human CLDN18.2, and, in particular, to a protein comprising, preferably consisting of the amino acid sequence according to SEQ ID NO: 1 of the sequence listing or a variant of said amino acid sequence. The first extracellular loop or domain of CLDN18.2 preferably comprises amino acids 27 to 81, more preferably amino acids 29 to 78 of the amino acid sequence shown in SEQ ID NO: 1. The second extracellular loop or domain of CLDN18.2 preferably comprises amino acids 140 to 180 of the amino acid sequence shown in SEQ ID NO: 1. Said first and second extracellular loops or domains preferably form the extracellular portion of CLDN18.2.

CLDN18.2 is selectively expressed in normal tissues in differentiated epithelial cells of the gastric mucosa. CLDN18.2 is expressed in cancers of various origins such as pancreatic carcinoma, esophageal carcinoma, gastric carcinoma, bronchial carcinoma, breast carcinoma, and ENT tumors. CLDN18.2 is a valuable target for the prevention and/or treatment of primary tumors, such as gastric cancer, esophageal cancer, pancreatic cancer, lung cancer such as non small cell lung cancer (NSCLC), ovarian cancer, colon cancer, hepatic cancer, head-neck cancer, and cancers of the gallbladder, and metastases thereof, in particular gastric cancer metastasis such as Krukenberg tumors, peritoneal metastasis, and lymph node metastasis.

The term "CLDN18.1" preferably relates to human CLDN18.1, and, in particular, to a protein comprising, preferably consisting of the amino acid sequence according to SEQ ID NO: 2 of the sequence listing or a variant of said amino acid sequence.

"Prognosis" as used herein refers to a prediction of outcome and, in particular, the probability of progression-free survival (PFS) or disease-free survival (DFS). Survival is usually calculated as an average number of months (or years) that 50% of patients survive, or the percentage of patients that are alive after 1, 5, 15, and 20 years. Prognosis is important for treatment decisions because patients with a good prognosis are usually offered less invasive treatments, while patients with poor prognosis are usually offered more aggressive treatments, such as more extensive chemotherapy drugs.

"Prediction" as used herein refers to providing information about the possible response of a disease to a distinct therapeutic treatment.

The phrase "indicate a risk" refers to the indication of a certain degree of likelihood or probability. The phrase "indicate a reduced risk" refers to a low degree of likelihood or probability. The phrase "indicate an increased risk" refers to a certain, higher or high degree of likelihood or probability.

If an event "indicates a reduced risk of a cancer patient not being a responder to treatment with an antibody" said event is indicative for a cancer patient being a responder to treatment with the antibody, i.e. it is likely that the patient is a responder to treatment with the antibody and optionally it is more likely that the patient is a responder to treatment with the antibody than the patient not being a responder to treatment with the antibody.

If an event "indicates an increased risk of a cancer patient not being a responder to treatment with an antibody" said event is indicative for a cancer patient not being a responder to treatment with the antibody, i.e. it is likely that the patient is not a responder to treatment with the antibody and optionally it is more likely that the patient is not a responder to treatment with the antibody than the patient being a responder to treatment with the antibody.

If an event "indicates a reduced risk of poor clinical outcome" said event is indicative for a good clinical outcome, i.e. it is likely that there will be a good clinical outcome and optionally it is more likely that there will be a good clinical outcome than there being a poor clinical outcome.

If an event "indicates an increased risk of poor clinical outcome" said event is indicative for a poor clinical outcome, i.e. it is likely that there will be a poor clinical outcome and optionally it is more likely that there will be a poor clinical outcome than there being a good clinical outcome.

If an event "indicates a reduced risk of a cancer patient not experiencing progression-free survival" said event is indicative for a cancer patient experiencing progression-free survival, i.e. it is likely that the patient experiences progression-free survival and optionally it is more likely that the patient experiences progression-free survival than the patient not experiencing progression-free survival.

If an event "indicates an increased risk of a cancer patient not experiencing progression-free survival" said event is indicative for a cancer patient not experiencing progression-free survival, i.e. it is likely that the patient does not experience progression-free survival and optionally it is more likely that the patient does not experience progression-free survival than the patient experiencing progression-free survival.

The term "sample", as used herein, refers to any material which is obtained from a subject and which may be used for analytical purposes, in particular for the determination of the genotype for one or more single-nucleotide polymorphisms. In certain embodiments, the samples described herein can be or can be derived from any tissues, cells and/or cells in biological fluids from, for example, a mammal or human to be tested. A sample may be isolated from a patient, e.g. from the human body. A sample can be a fractionated and/or purified sample. For example, samples encompassed by the present invention may be or may be derived from tissue (e.g. section or explant) samples, single cell samples, cell colony samples, cell culture samples, blood (e.g. whole blood or blood fraction such as blood cell fraction, serum or plasma) samples, urine samples, or samples from other peripheral sources. In one particularly preferred embodiment, the sample is a tissue sample (e.g., a biopsy from a subject with or suspected of having cancerous tissue). For example, the sample may be a biopsy of a tumor. The sample may be obtained from a patient prior to initiation of a therapeutic treatment, during the therapeutic treatment, and/or after the therapeutic treatment, e.g. prior to, during or following the administration of cancer therapy.

Sample materials can be used to produce nucleic acid extracts (including DNA and/or RNA), proteins or membrane extracts from any bodily fluids (such as blood, serum, plasma, urine, saliva, phlegm, gastric juices, semen, tears, sweat, etc.), skin, hair, cells (especially nucleated cells), biopsies, buccal swabs or tissue or tumor specimens.

The present invention further relates to a kit comprising means such as reagents for determining the genotype for one or more single-nucleotide polymorphisms as described herein. In the context of the present invention, the term "kit of parts (in short: kit)" is understood to be any combination of at least some of the components identified herein, which are combined, coexisting spatially, to a functional unit, and which can contain further components. For example, the kit may comprise pre-selected primers or probes specific for nucleic acid sequences comprising one or more single-nucleotide polymorphisms the genotype of which is to be determined. The kit may also comprise enzymes suitable for amplifying nucleic acids (e.g., polymerases such as Taq), and deoxynucleotides and buffers needed for the reaction mixture for amplification. The kit may also comprise probes specific for one or more single-nucleotide polymorphisms. In certain embodiments, said means are detectably labeled.

A kit of the invention may comprise (i) a container, and/or (ii) a data carrier. Said container may be filled with one or more of the above mentioned means or reagents. Said data carrier may be a non-electronical data carrier, e.g. a graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g. an internet database, a centralized, or a decentralized database. Said data carrier may comprise instructions for allowing the analysis of results obtained with said kit and, in particular, for the use of the kit in the methods of the invention.

Additionally or alternatively, said kit may comprise materials desirable from a commercial and user standpoint including buffer(s), reagent(s) and/or diluent(s).

Based on the results obtained (i.e. on the basis of the genotype for one or more single-nucleotide polymorphisms), the medical practitioner may choose a cancer therapy to which the patient is predicted as being responsive, in particular antibody therapy. Preferably, a cancer therapy to which the patient is predicted as being non-responsive is not administered to the patient.

Based on the result that the patient is predicted as being non-responsive to antibody therapy, in particular antibody therapy acting through recruiting the patient's immune system to destroy tumor cells, the medical practitioner may choose to administer cancer therapy which is different from antibody therapy, in particular antibody therapy acting through recruiting the patient's immune system to destroy tumor cells. In particular, the medical practitioner may choose to administer chemotherapy.

Based on the result that the patient is predicted as being responsive to antibody therapy, in particular antibody therapy acting through recruiting the patient's immune system to destroy tumor cells, the medical practitioner may choose to administer antibody therapy, in particular antibody therapy acting through recruiting the patient's immune system to destroy tumor cells, optionally in combination with chemotherapy.

The term "(therapeutic) treatment", in particular in connection with the treatment of cancer as used herein, relates to any treatment which aims at improving the health status and/or prolonging (increasing) the lifespan of a patient. Said treatment may eliminate cancer, reduce the size or the number of tumors in a patient, arrest or slow the development of cancer in a patient, inhibit or slow the development of new cancer in a patient, decrease the frequency or severity of symptoms in a patient, and/or decrease recurrences in a patient who currently has or who previously has had cancer. A (therapeutic) treatment of cancer may be selected from the group consisting of surgery, chemotherapy, radiation therapy and targeted therapy. One particularly preferred treatment according to the invention is the treatment of cancer involving therapeutic monoclonal antibodies against tumor antigens such as CLDN18.2 expressed on target cells.

Adjuvant therapy is a treatment that is given in addition to the primary, main or initial treatment. The surgeries and complex treatment regimens used in cancer therapy have led the term to be used mainly to describe adjuvant cancer treatments. An example of adjuvant therapy is the additional treatment usually given after surgery where all detectable disease has been removed, but where there remains a statistical risk of relapse due to occult disease.

Terms such as "responsive", or "responder" refer, in a therapeutic setting, to the fact that a patient has a therapeutic benefit from a given mode of treatment and, in particular, to the observation of an alleviation, prevention or elimination of a disease including shortening the duration of a disease, arresting or slowing progression or worsening of a disease, inhibiting or slowing the development of a new disease and/or recurrences, preventing or delaying the onset of a disease or the symptoms thereof, decreasing the frequency or severity of symptoms in a patient who currently has or who previously has had a disease and/or prolonging the lifespan of the patient. In particular, they refer to the observation of a reduction in tumor mass or of an increase in tumor free time, recurrence free time or overall survival time.

Terms such as "non-responsive" or "non-responder" refer, in a therapeutic setting, to the fact that a patient has no therapeutic benefit from a given mode of treatment and, in particular, to no observation of an alleviation, prevention or elimination of a disease, i.e. the patient is resistant to treatment.

Complete response is defined as the absence of any residual disease such as cancer, and is usually assessed by pathological analysis of acquired tissue samples. In this context, the term "pathological complete response" (pCR) is frequently used. In particular, pCR is defined as the absence of any residual invasive tumour cells in the original tumor bed. However, the definition of pCR may vary between different grading systems. Pathological complete response has shown to be a prognostic factor for overall better survival, but also for disease-free survival and recurrence free survival.

Recurrence-free survival is defined as the time from randomization to the first of either recurrence or relapse, second cancer, or death.

Progression-free survival (PFS) is a type of survival rate that measures the length of time during and after medication or treatment during which the disease being treated (usually cancer) does not get worse. It is sometimes used as a metric to study the health of a person with a disease to try to determine how well a new treatment is working and it is often used as a clinical endpoint in randomized controlled trials for cancer therapies.

According to the invention, the term "cancer patient experiencing progression-free survival" relates to a cancer patient having a prolonged time period without progression of the disease, in particular when compared to the average of patients and/or when compared to patients which are non-responders to a given mode of treatment. Preferably, said prolonged time period is at least 4, preferably at least 5, more preferably at least 6 months, such as at least 7 months or at least 8 months, said time period starting e.g. from the time of a first administration of a treatment.

The term "clinical outcome" is defined as the clinical result of a disease, e.g. reduction or amelioration of symptoms, in particular following a treatment.

The term "recurrence" with respect to cancer includes occurrence of tumor cells at the same site and organ of the origin disease, distant metastasis that can appear even many years after the initial diagnosis and therapy of cancer, or to local events such as infiltration of tumor cells into regional lymph nodes.

The terms "individual" and "subject" are used herein interchangeably. They refer to human beings, non-human primates or other mammals (e.g. mouse, rat, rabbit, dog, cat, cattle, swine, sheep, horse or primate) that can be afflicted with or are susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In preferred embodiments of the present invention, the "individual" or "subject" is a "patient". The term "patient" means according to the invention a subject for treatment, in particular a diseased subject.

In one particularly preferred embodiment, a method of the invention is performed on a patient which is already diagnosed as having cancer.

"Target cell" shall mean any undesirable cell such as a cancer cell. In preferred embodiments, the target cell expresses CLDN18.2.

In the context of the present invention, terms such as "protect", "prevent" or "prophylactic" relate to the prevention of the occurrence and/or the propagation of a disease in a subject and, in particular, to minimizing the chance that a subject will develop a disease or to delaying the development of a disease. For example, a subject at risk for cancer would be a candidate for therapy to prevent cancer.

By "being at risk" is meant a subject that is identified as having a higher than normal chance of developing a disease, in particular cancer, compared to the general population. In addition, a subject who has had, or who currently has, a disease, in particular cancer, is a subject who has an increased risk for developing a disease, as such a subject may continue to develop a disease. Subjects who currently have, or who have had, a cancer also have an increased risk for cancer metastases.

As used herein, the term "combination" in the context of the administration of a therapy refers to the use of more than one therapy or therapeutic agent. The use of the term "in combination" does not restrict the order in which the therapies or therapeutic agents are administered to a subject. A therapy or therapeutic agent can be administered prior to, concomitantly with, or subsequent to the administration of a second therapy or therapeutic agent to a subject. Preferably, the therapies or therapeutic agents are administered to a subject in a sequence, amount and/or within a time interval such that the therapies or therapeutic agents can act together. In a particular embodiment, the therapies or therapeutic agents are administered to a subject in a sequence, amount and/or within a time interval such that they provide an increased benefit than if they were administered otherwise, in particular, independently from each other. Preferably, the increased benefit is a synergistic effect.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality. According to the invention, the term "disease" includes cancer, in particular those forms of cancer described herein. Any reference herein to cancer or particular forms of cancer also includes cancer metastasis thereof. In a preferred embodiment, a disease to be treated according to the present application involves cells expressing a tumor antigen such as CLDN18.2.

"Disease involving cells expressing a tumor antigen" means according to the invention that a tumor antigen such as CLDN18.2 is expressed in cells of a diseased tissue or organ. In one embodiment, expression of a tumor antigen in cells of a diseased tissue or organ is increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a corresponding healthy tissue is repressed. According to the invention, diseases involving cells expressing a tumor antigen include cancer diseases. Furthermore, according to the invention, cancer diseases preferably are those wherein the cancer cells express a tumor antigen.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases. Preferably, a "cancer disease" is characterized by cells expressing a tumor antigen such as CLDN18.2 and a cancer cell expresses such tumor antigen. A cell expressing a tumor antigen such as CLDN18.2 preferably is a cancer cell, preferably of the cancers described herein.

According to the invention, the term "tumor" or "tumor disease" refers to an abnormal growth of cells (called neoplastic cells, tumorigenous cells or tumor cells) preferably forming a swelling or lesion. By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

In one embodiment, a cancer according to the invention involves cancer cells expressing a tumor antigen such as CLDN18.2. In one embodiment, the cancer is tumor antigen positive such as CLDN18.2 positive. In one embodiment, expression of the tumor antigen such as CLDN18.2 is at the surface of the cells. In one embodiment, at least 50%, preferably 60%, 70%, 80% or 90% of the cancer cells are tumor antigen positive such as CLDN18.2 positive and/or at least 40%, preferably at least 50% of the cancer cells are positive for surface expression of the tumor antigen such as CLDN18.2. In one embodiment, at least 95% or at least 98% of the cancer cells are tumor antigen positive such as CLDN18.2 positive. In one embodiment, at least 60%, at least 70%, at least 80% or at least 90% of the cancer cells are positive for surface expression of the tumor antigen such as CLDN18.2.

In one embodiment, a cancer involving cancer cells expressing CLDN18.2 or a CLDN18.2 positive cancer is selected from the group consisting of gastric cancer, esophageal cancer, pancreatic cancer, lung cancer such as non small cell lung cancer (NSCLC), ovarian cancer, colon cancer, hepatic cancer, head-neck cancer, and cancer of the gallbladder and metastases thereof, in particular gastric cancer metastasis such as Krukenberg tumors, peritoneal metastasis and lymph node metastasis. In one embodiment, the cancer is an adenocarcinoma, in particular an advanced adenocarcinoma. Particularly preferred cancer diseases are adenocarcinomas of the stomach, the esophagus, the pancreatic duct, the bile ducts, the lung and the ovary. In one embodiment, the cancer is selected from the group consisting of cancer of the stomach, cancer of the esophagus, in particular the lower esophagus, cancer of the eso-gastric junction and gastroesophageal cancer. In a particularly preferred embodiment, the cancer is gastroesophageal cancer such as metastatic, refractory or recurrent advanced gastroesophageal cancer. In one embodiment, a CLDN18.2 positive tumor is a tumor of the above cancer types.

Embodiments involving a CLDN18.2 positive tumor or cancer cells expressing CLDN18.2 preferably involve the use of an antibody having the ability of binding to CLDN18.2. In one embodiment, an antibody having the ability of binding to CLDN18.2 is a monoclonal, chimeric or humanized antibody, or a fragment of an antibody.

According to the invention, a "carcinoma" is a malignant tumor derived from epithelial cells. This group represents the most common cancers, including the common forms of breast, prostate, lung and colon cancer.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer.

Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis. One particular form of metastasis which is treatable using the therapy of the invention is metastasis originating from gastric cancer as primary site. In preferred embodiments such gastric cancer metastasis is Krukenberg tumors, peritoneal metastasis and/or lymph node metastasis.

A refractory cancer is a malignancy for which a particular treatment is ineffective, which is either initially unresponsive to treatment, or which becomes unresponsive over time. The terms "refractory", "unresponsive" or "resistant" are used interchangeably herein.

Krukenberg tumor is an uncommon metastatic tumor of the ovary accounting for 1% to 2% of all ovarian tumors. Prognosis of Krukenberg tumor is still very poor and there is no established treatment for Krukenberg tumors. Krukenberg tumor is a metastatic signet ring cell adenocarcinoma of the ovary. Stomach is the primary site in most Krukenberg tumor cases (70%). Carcinomas of colon, appendix, and breast (mainly invasive lobular carcinoma) are the next most common primary sites. Rare cases of Krukenberg tumor originating from carcinomas of the gallbladder, biliary tract, pancreas, small intestine, ampulla of Vater, cervix, and urinary bladder/urachus have been reported.

The term "surgery", as used herein, includes the removal of tumors in an operation. It is a common treatment for cancer. A surgeon may remove the tumors using local excision.

The term "chemotherapy", as used herein, refers to the use of chemotherapeutic agents or combinations of chemotherapeutic agents, preferably to stop the growth of cancer cells, either by killing the cells or by stopping them from dividing. When chemotherapy is taken by mouth or injected into a vein or muscle, the drugs enter the bloodstream and can reach cancer cells throughout the body (systemic chemotherapy). When chemotherapy is placed directly into the cerebrospinal fluid, an organ, or a body cavity such as the abdomen, the drugs mainly affect cancer cells in those areas (regional chemotherapy).

Chemotherapeutic agents according to the invention include cytostatic compounds and cytotoxic compounds.

Traditional chemotherapeutic agents act by killing cells that divide rapidly, one of the main properties of most cancer cells. This means that chemotherapy also harms cells that divide rapidly under normal circumstances such as cells in the bone marrow, digestive tract, and hair follicles. This results in the most common side-effects of chemotherapy. According to the invention, the term "chemotherapy" preferably does not include antibodies that target proteins that are abnormally expressed in cancer cells (tumor antigens) and act through recruiting the patient's immune system to destroy tumor cells. Antibodies that target proteins that are abnormally expressed in cancer cells (tumor antigens) and act through a therapeutic moiety or agent conjugated to the antibody, however, can be viewed as a form of chemotherapy. However, in the strictest sense, the term "chemotherapy" according to the invention does not include targeted therapy.

According to the invention, the term "chemotherapeutic agent" includes taxanes, platinum compounds, nucleoside analogs, camptothecin analogs, anthracyclines, etoposide, bleomycin, vinorelbine, cyclophosphamide, and combinations thereof. According to the invention a reference to a chemotherapeutic agent is to include any prodrug such as ester, salt or derivative such as conjugate of said agent. Examples are conjugates of said agent with a carrier substance, e.g. protein-bound paclitaxel such as albumin-bound paclitaxel. Preferably, salts of said agent are pharmaceutically acceptable.

Taxanes are a class of diterpene compounds that were first derived from natural sources such as plants of the genus *Taxus*, but some have been synthesized artificially. The principal mechanism of action of the taxane class of drugs is the disruption of microtubule function, thereby inhibiting the process of cell division. Taxanes include docetaxel (Taxotere) and paclitaxel (Taxol).

According to the invention, the term "docetaxel" refers to a compound having the following formula:

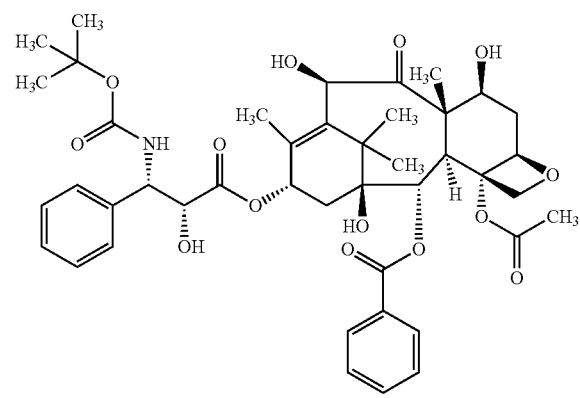 [SMILES: CC(=O)O[C@@]12CO[C@@H]1C[C@H](O)[C@@]1(C)C(=O)[C@H](O)C3=C(C)[C@@H](OC(=O)[C@H](O)[C@@H](NC(=O)OC(C)(C)C)c4ccccc4)C[C@@](O)([C@@H](OC(=O)c4ccccc4)[C@H]21)C3(C)C]

In particular, the term "docetaxel" refers to the compound 1,7β,10β-trihydroxy-9-oxo-5β,20-epoxytax-11-ene-2α,4,13α-triyl 4-acetate 2-benzoate 13-{(2R,3S)-3-[(tert-butoxycarbonyl)-amino]-2-hydroxy-3-phenylpropanoate}.

According to the invention, the term "paclitaxel" refers to a compound having the following formula:

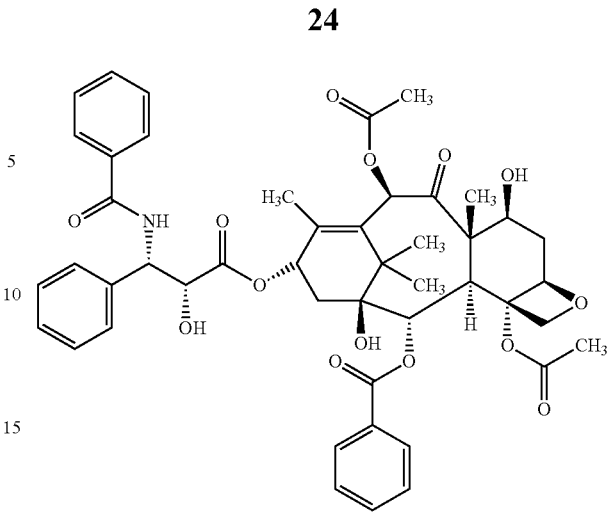

In particular, the term "paclitaxel" refers to the compound (2α,4α,5β,7β,10β,13α)-4,10-bis-(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate.

According to the invention, the term "platinum compound" refers to compounds containing platinum in their structure such as platinum complexes and includes compounds such as cisplatin, carboplatin and oxaliplatin.

The term "cisplatin" or "cisplatinum" refers to the compound cis-diamminedichloroplatinum(II) (CDDP) of the following formula:

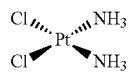

The term "carboplatin" refers to the compound cis-diammine(1,1-cyclobutanedicarboxylato)platinum(II) of the following formula:

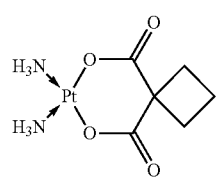

The term "oxaliplatin" refers to a compound which is a platinum compound that is complexed to a diaminocyclohexane carrier ligand of the following formula:

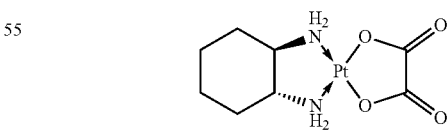

In particular, the term "oxaliplatin" refers to the compound [(1R,2R)-cyclohexane-1,2-diamine](ethanedioato-O, O')platinum(II). Oxaliplatin for injection is also marketed under the trade name Eloxatine.

The term "nucleoside analog" refers to a structural analog of a nucleoside, a category that includes both purine analogs and pyrimidine analogs.

The term "gemcitabine" is a compound which is a a nucleoside analog of the following formula:

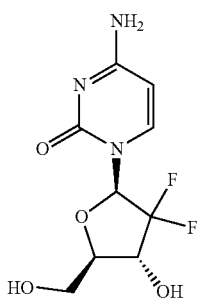 [SMILES: Nc1ccn([C@@H]2O[C@H](CO)[C@@H](O)C2(F)F)c(=O)n1]

In particular, the term refers to the compound 4-amino-1-(2-deoxy-2,2-difluoro-3-D-erythro-pentofuranosyl)pyrimidin-2(1H)-one or 4-amino-1-[(2R,4R,5R)-3,3-difluoro-4-hydroxy-5-(hydroxymethyl)oxolan-2-yl]-1,2-dihydropyrimidin-2-one.

The term "nucleoside analog" includes fluoropyrimidine derivatives such as fluorouracil and prodrugs thereof. The term "fluorouracil" or "5-fluorouracil" (5-FU or f5U) (sold under the brand names Adrucil, Carac, Efudix, Efudex and Fluoroplex) is a compound which is a pyrimidine analog of the following formula:

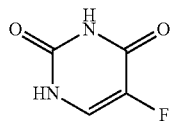

In particular, the term refers to the compound 5-fluoro-1H-pyrimidine-2,4-dione.

The term "capecitabine" (Xeloda, Roche) refers to a chemotherapeutic agent that is a prodrug that is converted into 5-FU in the tissues. Capecitabine which may be orally administered has the following formula:

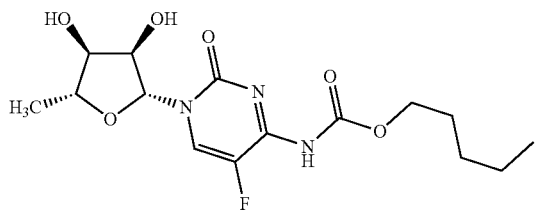 [SMILES: CCCCCOC(=O)Nc1nc(=O)n([C@@H]2O[C@H](C)[C@@H](O)[C@H]2O)cc1F]

In particular, the term refers to the compound pentyl [1-(3,4-dihydroxy-5-methyltetrahydrofuran-2-yl)-5-fluoro-2-oxo-1H-pyrimidin-4-yl]carbamate.

The term "folinic acid" or "leucovorin" refers to a compound useful in synergistic combination with the chemotherapy agent 5-fluorouracil. Thus, if reference is made herein to the administration of 5-fluorouracil or a prodrug thereof, said administration in one embodiment may comprise an administration in conjunction with folinic acid. Folinic acid has the following formula:

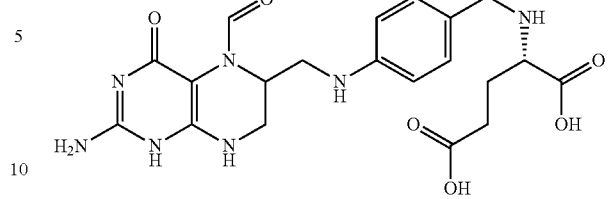

In particular, the term refers to the compound (2S)-2-{[4-[(2-amino-5-formyl-4-oxo-5,6,7,8-tetrahydro-1H-pteridin-6-yl)methylamino]benzoyl]amino}pentanedioic acid.

According to the invention, the term "camptothecin analog" refers to derivatives of the compound camptothecin (CPT; (S)-4-ethyl-4-hydroxy-1H-pyrano[3',4':6,7]indolizino[1,2-b] quinoline-3,14-(4H,12H)-dione). Preferably, the term "camptothecin analog" refers to compounds comprising the following structure:

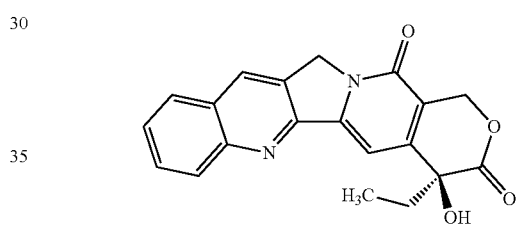

According to the invention, preferred camptothecin analogs are inhibitors of DNA enzyme topoisomerase I (topo I). Preferred camptothecin analogs according to the invention are irinotecan and topotecan.

Irinotecan is a drug preventing DNA from unwinding by inhibition of topoisomerase I. In chemical terms, it is a semisynthetic analogue of the natural alkaloid camptothecin having the following formula:

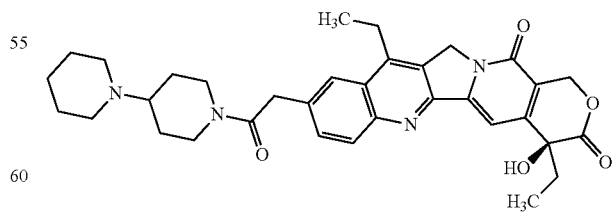

In particular, the term "irinotecan" refers to the compound (S)-4,11-diethyl-3,4,12,14-tetrahydro-4-hydroxy-3,14-dioxo1H-pyrano[3',4':6,7]-indolizino[1,2-b]quinolin-9-yl-[1,4'-bipiperidine]-1'-carboxylate.

Topotecan is a topoisomerase inhibitor of the formula:

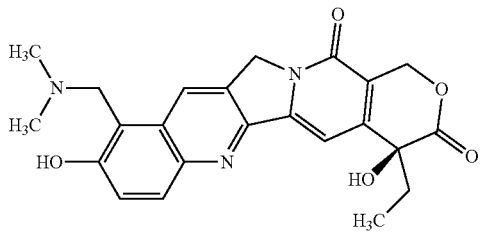 [SMILES: CC[C@@]1(O)C(=O)OCc2c1cc1n(c2=O)Cc2cc3c(CN(C)C)c(O)ccc3nc2-1]

In particular, the term "topotecan" refers to the compound (S)-10-[(dimethylamino)methyl]-4-ethyl-4,9-dihydroxy-1H-pyrano[3',4':6,7]indolizino[1,2-b]quinoline-3,14(4H,12H)-dione monohydrochloride.

Anthracyclines are a class of drugs commonly used in cancer chemotherapy that are also antibiotics. Structurally, all anthracyclines share a common four-ringed 7,8,9,10-tetrahydrotetracene-5,12-quinone structure and usually require glycosylation at specific sites.

Anthracyclines preferably bring about one or more of the following mechanisms of action: 1. Inhibiting DNA and RNA synthesis by intercalating between base pairs of the DNA/RNA strand, thus preventing the replication of rapidly-growing cancer cells. 2. Inhibiting topoisomerase II enzyme, preventing the relaxing of supercoiled DNA and thus blocking DNA transcription and replication. 3. Creating iron-mediated free oxygen radicals that damage the DNA and cell membranes.

According to the invention, the term "anthracycline" preferably relates to an agent, preferably an anticancer agent for inducing apoptosis, preferably by inhibiting the rebinding of DNA in topoisomerase II.

Examples of anthracyclines and anthracycline analogs include, but are not limited to, daunorubicin (daunomycin), doxorubicin (adriamycin), epirubicin, idarubicin, rhodomycin, pyrarubicin, valrubicin, N-trifluoro-acetyl doxorubicin-14-valerate, aclacinomycin, morpholinodoxorubicin (morpholino-DOX), cyanomorpholino-doxorubicin (cyanomorpholino-DOX), 2-pyrrolino-doxorubicin (2-PDOX), 5-iminodaunomycin, mitoxantrone and aclacinomycin A (aclarubicin). Mitoxantrone is a member of the anthracendione class of compounds, which are anthracycline analogs that lack the sugar moiety of the anthracyclines but retain the planar polycylic aromatic ring structure that permits intercalation into DNA.

Specifically contemplated as anthracycline in the context of the present invention is epirubicin. Epirubicin is an anthracycline drug which has the following formula:

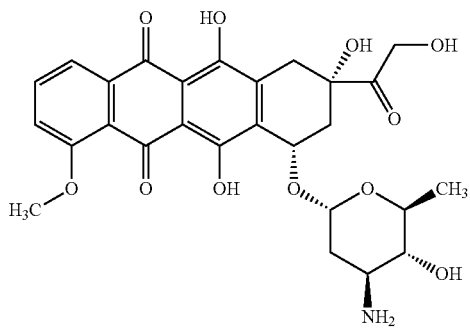 [SMILES: COc1cccc2c1C(=O)c1c(O)c3c(c(O)c1C2=O)C[C@@](O)(C(=O)CO)C[C@@H]3O[C@H]1C[C@H](N)[C@@H](O)[C@H](C)O1]

and is marketed under the trade name Ellence in the US and Pharmorubicin or Epirubicin Ebewe elsewhere. In particular, the term "epirubicin" refers to the compound (8R,10S)-10-[(2S,4S,5R,6S)-4-amino-5-hydroxy-6-methyl-oxan-2-yl]oxy-6,11-dihydroxy-8-(2-hydroxyacetyl)-1-methoxy-8-methyl-9,10-dihydro-7H-tetracen-5,12-dion. Epirubicin is favoured over doxorubicin, the most popular anthracycline, in some chemotherapy regimens as it appears to cause fewer side-effects.

The term "etoposide" refers to a semisynthetic derivative of podophyllotoxin that exhibits antitumor activity. Etoposide inhibits DNA synthesis by forming a complex with topoisomerase II and DNA. This complex induces breaks in double stranded DNA and prevents repair by topoisomerase II binding. Accumulated breaks in DNA prevent entry into the mitotic phase of cell division, and lead to cell death. Etoposide has the following formula:

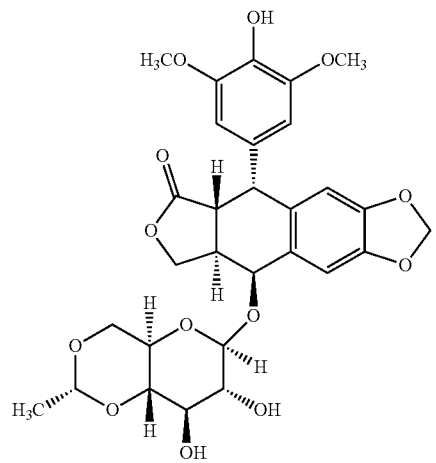 [SMILES: COc1cc([C@@H]2c3cc4c(cc3[C@@H](O[C@@H]3O[C@@H]5CO[C@@H](C)O[C@H]5[C@H](O)[C@H]3O)[C@H]3COC(=O)[C@H]23)OCO4)cc(OC)c1O]

In particular, the term refers to the compound 4'-demethyl-epipodophyllotoxic 9-[4,6-O—(R)-ethylidene-beta-D-glucopyranoside], 4'-(dihydrogen phosphate).

The term "bleomycin" refers to a glycopeptide antibiotic produced by the bacterium *Streptomyces verticillus*. When used as an anticancer agent, it works by causing breaks in DNA. Bleomycin preferably comprises a compound having the following formula:

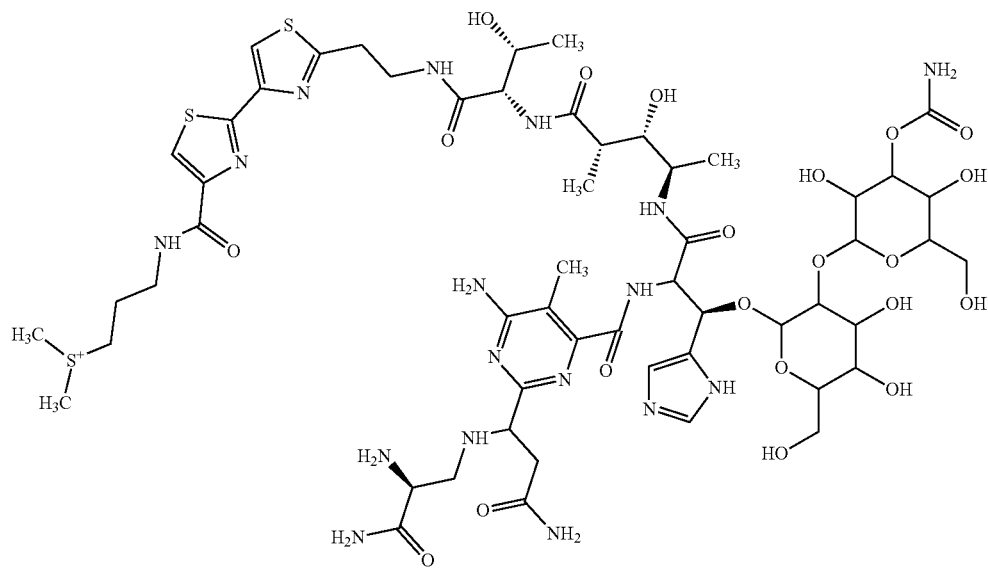 [SMILES: Cc1c(N)nc(C(CC(N)=O)NC[C@H](N)C(N)=O)nc1C(=O)NC(C(=O)N[C@H](C)[C@@H](O)[C@H](C)C(=O)N[C@H](C(=O)NCCc1nc(-c2nc(C(=O)NCCC[S+](C)C)cs2)cs1)[C@@H](C)O)[C@@H](OC1OC(CO)C(O)C(O)C1OC1OC(CO)C(O)C(OC(N)=O)C1O)c1cnc[nH]1]

The term "vinorelbine" refers to an anti-mitotic chemotherapy drug that is a semi-synthetic vinca alkaloid and is given as a treatment for some types of cancer, including breast cancer and non-small cell lung cancer. Vinorelbine preferably comprises a compound having the following formula:

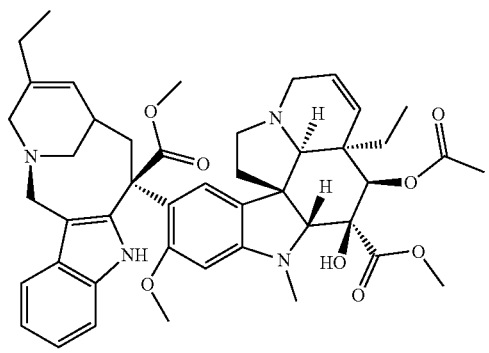

Cyclophosphamide is a nitrogen mustard alkylating agent from the oxazophorines group. The main use of cyclophosphamide is with other chemotherapy agents in the treatment of some forms of cancer. Cyclophosphamide preferably comprises a compound having the following formula:

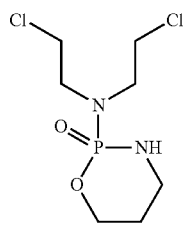 [SMILES: O=P1(N(CCCl)CCCl)NCCCO1]

In the context of the present invention, the term "radiation therapy" refers to the use of high-energy x-rays or other types of radiation to kill cancer cells or keep them from growing. There are two types of radiation therapy. External radiation therapy uses a machine outside the body to send radiation toward the cancer. Internal radiation therapy uses a radioactive substance sealed in needles, seeds, wires, or catheters that are placed directly into or near the cancer. The way the radiation therapy is given depends on the type and stage of the cancer being treated.

According to the invention, the term "targeted therapy" relates to any therapy that can be used to target preferentially diseased cells such as cancer cells while non-diseased cells are not targeted or targeted to a lesser extent. Targeting of diseased cells preferably results in killing and/or impairment of proliferation or viability of diseased cells. Such therapy includes i) antibodies, antibody fragments, and proteins that are either naked or conjugated to a therapeutic moiety that target certain cell surface targets on diseased cells, such as tumor antigens, for example, CLDN18.2, (e.g. antibodies or antibody conjugates against CLDN18.2 as described herein) or ii) small molecules which impair proliferation or viability of diseased cells. In a specific embodiment, the agent binds to an antigen that is expressed at a greater level on diseased than on normal stem cells. In a specific embodiment, the agent binds specifically to a tumor antigen. Traditional chemotherapy or radiotherapy is not considered a "targeted therapy" despite its often being aimed at the tumours. Furthermore, the term "antibody therapy" according to the invention preferably does not include therapy with antibodies, fragments or derivatives thereof that are conjugated to a therapeutic moiety but merely relates to therapy with antibodies, fragments or derivatives thereof acting through recruiting the patient's immune system to destroy tumor cells.

The term "antigen" relates to an agent comprising an epitope against which an immune response is to be generated and/or is directed. The term "antigen" includes in particular proteins, peptides, polysaccharides, nucleic acids, especially RNA and DNA, and nucleotides. The term "antigen" also includes agents, which become antigenic—and sensitizing—only through transformation (e.g. intermediately in the molecule or by completion with body protein). An antigen or a processing product thereof is preferably recognizable by a T or B cell receptor, or by an immunoglobulin molecule such as an antibody. In a preferred embodiment, the antigen is a disease-associated antigen, such as a tumor antigen, such as CLDN18.2.

In the context of the present invention, the term "tumor antigen" or "tumor-associated antigen" relates to an antigen which is present in tumor cells. Preferably the antigen is present on tumor cells, such as on the surface of tumor cells. Preferably, the "tumor antigen" is expressed by tumor cells. In one embodiment, the term "tumor antigen" relates to proteins which are aberrantly expressed in tumor cells when compared to the normal, i.e. non-tumorous, cells. For example, expression may be only found in tumor cells but not in the normal, i.e. non-tumorous, cells or the level of expression may be higher in tumor cells compared to the normal, i.e. non-tumorous, cells. In one embodiment, the term "tumor antigen" relates to proteins that are under normal conditions specifically expressed in a limited number of tissues and/or organs or in specific developmental stages and are expressed or aberrantly expressed in one or more tumor or cancer tissues. In the context of the present invention, a tumor antigen is preferably associated with the cell surface of a cancer cell and is preferably not, only rarely or at a lower level expressed in normal tissues and cells. Preferably, according to the invention, a tumor antigen is not expressed in a cell if the level of expression is below the detection limit and/or if the level of expression is too low to allow binding by tumor antigen-specific antibodies added to the cells. A particularly preferred tumor antigen according to the invention is CLDN18.2.

According to the invention, the term "tumor antigen-positive cancer" or "tumor antigen-positive tumor" or similar terms means a cancer or tumor involving cancer or tumor cells expressing a tumor antigen, preferably on the surface of said cancer cells or tumor cells. A tumor antigen is expressed on the surface of cells if it is located at the surface of said cells and is accessible to binding by tumor antigen-specific antibodies added to the cells.

In one preferred embodiment of the invention, a "tumor antigen-positive cancer" or "tumor antigen-positive tumor" is a "CLDN18.2-positive cancer" or "CLDN18.2-positive tumor". According to the invention, the term "CLDN18.2 positive cancer" or "CLDN18.2-positive tumor" means a cancer or tumor involving cancer or tumor cells expressing CLDN18.2, preferably on the surface of said cancer cells or tumor cells.

"Cell surface" is used in accordance with its normal meaning in the art, and thus includes the outside of the cell which is accessible to binding by proteins and other molecules.

The term "extracellular portion" in the context of the present invention refers to a part of a molecule such as a protein that is facing the extracellular space of a cell and preferably is accessible from the outside of said cell, e.g., by antigen-binding molecules such as antibodies located outside the cell. Preferably, the term refers to one or more extracellular loops or domains or a fragment thereof.

According to the invention, CLDN18.2 is not substantially expressed in a cell if the level of expression is lower compared to expression in stomach cells or stomach tissue. Preferably, the level of expression is less than 10%, preferably less than 5%, 3%, 2%, 1%, 0.5%, 0.1% or 0.05% of the expression in stomach cells or stomach tissue or even lower. Preferably, CLDN18.2 is not substantially expressed in a cell if the level of expression exceeds the level of expression in non-cancerous tissue other than stomach by no more than 2-fold, preferably 1,5-fold, and preferably does not exceed the level of expression in said non-cancerous tissue. Preferably, CLDN18.2 is not substantially expressed in a cell if the level of expression is below the detection limit and/or if the level of expression is too low to allow binding by CLDN18.2-specific antibodies added to the cells.

According to the invention, CLDN18.2 is expressed in a cell if the level of expression exceeds the level of expression in non-cancerous tissue other than stomach preferably by more than 2-fold, preferably 10-fold, 100-fold, 1000-fold, or 10000-fold. Preferably, CLDN18.2 is expressed in a cell if the level of expression is above the detection limit and/or if the level of expression is high enough to allow binding by CLDN18.2-specific antibodies added to the cells. Preferably, CLDN18.2 expressed in a cell is expressed or exposed on the surface of said cell.

The term "epitope" refers to an antigenic determinant in a molecule, i.e., to the part in a molecule that is recognized by the immune system, for example, that is recognized by an antibody. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. An epitope of a protein preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

The term "antibody" includes a glycoprotein comprising at least two heavy (H) chains and two light (L) chains inter-connected by disulfide bonds, and any molecule comprising an antigen-binding portion of such glycoprotein. The term "antibody" includes monoclonal antibodies, recombinant antibodies, human antibodies, humanized antibodies, chimeric antibodies, fragments or derivatives of antibodies, including, without limitation, single chain antibodies, e.g., scFv's and antigen-binding antibody fragments such as Fab and Fab' fragments and also includes all recombinant forms of antibodies, e.g., antibodies expressed in prokaryotes, unglycosylated antibodies, and any antigen-binding antibody fragments and derivatives as described herein. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "human antibody", as used herein, is intended to include antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g., modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

Antibodies may be derived from different species, including but not limited to mouse, rat, rabbit, guinea pig and human.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

The antibodies described herein are preferably isolated. An "isolated antibody" as used herein, is intended to refer to an antibody which is substantially free of other antibodies having different antigenic specificities (e.g., an isolated antibody that specifically binds to a tumor antigen is substantially free of antibodies that specifically bind antigens other than the tumor antigen). An isolated antibody that specifically binds to an epitope, isoform or variant of a human tumor antigen may, however, have cross-reactivity to other related antigens, e.g., from other species (e.g., tumor antigen species homologs). Moreover, an isolated antibody may be substantially free of other cellular material and/or chemicals. In one embodiment of the invention, a combination of "isolated" monoclonal antibodies relates to antibodies having different specificities and being combined in a well-defined composition or mixture.

The terms "antigen-binding portion" of an antibody (or simply "binding portion") or "antigen-binding fragment" of an antibody (or simply "binding fragment") or similar terms refer to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "binding domain" characterizes in connection with the present invention a structure, e.g. of an antibody, which binds to/interacts with a given target structure/antigen/epitope. Thus, the binding domain according to the invention designates an "antigen-interaction-site".

All antibodies and derivatives of antibodies such as antibody fragments as described herein for the purposes of the invention are encompassed by the term "antibody". The term "antibody derivatives" refers to any modified form of an antibody, e.g., a conjugate of the antibody and another agent or antibody, or an antibody fragment.

Naturally occurring antibodies are generally monospecific, i.e. they bind to a single antigen. The present invention comprises antibodies binding to a target cell (by engaging a tumor antigen) and a second entity such as a cytotoxic cell (e.g. by engaging the CD3 receptor). The antibodies of the present invention may be bispecific or multispecific such as trispecific, tetraspecific and so on.

The term "bispecific molecule" is intended to include an agent which has two different binding specificities. For example, the molecule may bind to, or interact with (a) a cell surface antigen, and (b) a receptor such as an Fc receptor on the surface of an effector cell. The term "multispecific molecule" is intended to include an agent which has more than two different binding specificities. For example, the molecule may bind to, or interact with (a) a cell surface antigen, (b) a receptor such as an Fc receptor on the surface of an effector cell, and (c) at least one other component. Accordingly, the term "antibody against a tumor antigen" includes, but is not limited to, bispecific, trispecific, tetraspecific, and other multispecific molecules which are directed to a tumor antigen, and to other targets, such as Fc receptors on effector cells. The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90: 6444-6448; Poljak, R. J., et al. (1994) Structure 2: 1121-1123).

According to the invention, an antibody may exert its therapeutic effect through recruiting the patient's immune system to destroy tumor cells and/or through a therapeutic moiety or agent coupled to the antibody. For the purpose of the present invention, such antibody conjugates may be considered being encompassed by the term "chemotherapeutic agent" while antibodies exerting their therapeutic effect through recruiting the patient's immune system to destroy tumor cells are not.

In the context of the present invention, an antibody preferably is capable of acting through recruiting the patient's immune system to destroy tumor cells, i.e. the antibody, in particular when bound to its target such as a tumor antigen on a diseased cell, elicits immune effector functions as described herein. Preferably, said immune effector functions are directed against cells such as cancer cells carrying a tumor antigen such as CLDN18.2 on their surface.

The term "immune effector functions" in the context of the present invention includes any functions mediated by components of the immune system that result e.g. in the inhibition of tumor growth and/or inhibition of tumor development, including inhibition of tumor dissemination and metastasis. Preferably, immune effector functions result in killing of cancer cells. Such functions comprise complement dependent cytotoxicity (CDC), antibody-dependent cell-mediated cytotoxicity (ADCC), antibody-dependent cell-mediated phagocytosis (ADCP), induction of apoptosis in the cells carrying the tumor antigen, cytolysis of the cells carrying the tumor antigen, and/or inhibition of proliferation of the cells carrying the tumor antigen. Binding agents may also exert an effect simply by binding to tumor antigens on the surface of a cancer cell. For example, antibodies may block the function of the tumor antigen or induce apoptosis just by binding to the tumor antigen on the surface of a cancer cell.

Antibody-Dependent Cell-Mediated Cytotoxicity

ADCC describes the cell-killing ability of effector cells, in particular lymphocytes, which preferably requires the target cell being marked by an antibody.

ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that leads to antigen presentation and the induction of tumor-directed T-cell responses. Preferably, in vivo induction of ADCC will lead to tumor-directed T-cell responses and host-derived antibody responses.

Complement-Dependent Cytotoxicity

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the CH2 domains of participating antibody molecules such as IgG molecules (C1q is one of three subcomponents of complement C1). Preferably these uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell.

In order to inhibit tumor growth and/or tumor development, according to the invention, an antibody may be conjugated to a therapeutic moiety or agent, such as a cytotoxin, a drug (e.g., an immunosuppressant) or a radioisotope. A cytotoxin or cytotoxic agent includes any agent that is detrimental to and, in particular, kills cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, amanitin, 1-dehydrotestosterone, glucocorticoids, procaine, tetracaine, lidocaine, propranolol, and puromycin and analogs or homologs thereof. Suitable therapeutic agents for forming antibody conjugates include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin, cisplatin, bleomycin, sulfate, carmustine, chlorambucil, cyclophosphamide or ricin A.

Antibodies also can be conjugated to a radioisotope, e.g., iodine-131, yttrium-90 or indium-111, to generate cytotoxic radiopharmaceuticals.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

The term "antibody against a tumor antigen" or similar terms relates to an antibody directed to or having the ability of binding to the tumor antigen. The term "binding" according to the invention preferably relates to a specific binding.

According to the present invention, an antibody is capable of binding to a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An antibody is not (substantially) capable of binding to a target if it has no significant affinity for said target and does not bind significantly, in particular does not bind detectably, to said target in standard assays. Preferably, the antibody does not detectably bind to said target if present in a concentration of up to 2, preferably 10, more preferably 20, in particular 50 or 100 µg/ml or higher. Preferably, an antibody has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the antibody is capable of binding. For example, if the $K_D$ for binding of an antibody to the target to which the antibody is capable of binding is $10^{-7}$ M, the $K_D$ for binding to a target for which the antibody has no significant affinity would be is at least $10^{-6}$ M, $10^{-5}$ M, $10^{-4}$ M, $10^{-3}$ M, $10^{-2}$ M, or $10^{-1}$ M.

An antibody is specific for a predetermined target if it is capable of binding to said predetermined target while it is not capable of binding to other targets, i.e. has no significant affinity for other targets and does not significantly bind to other targets in standard assays. According to the invention, an antibody is specific for a tumor antigen if it is capable of binding to the tumor antigen but is not (substantially) capable of binding to other targets. Preferably, an antibody is specific for a tumor antigen if the affinity for and the binding to such other targets does not significantly exceed the affinity for or binding to tumor antigen-unrelated proteins such as bovine serum albumin (BSA), casein, human serum albumin (HSA) or non-tumor antigen transmembrane proteins such as MHC molecules or transferrin receptor or any other specified polypeptide. Preferably, an antibody is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an antibody to the target for which it is specific is $10^{-7}$ M, the $K_D$ for binding to a target for which it is not specific would be at least $10^{-6}$ M, $10^{-5}$ M, $10^{-4}$ M, $10^{-3}$ M, $10^{-2}$ M, or $10^{-1}$ M.

Binding of an antibody to a target can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. Affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $1C_{50}$, are preferably made with standardized solutions of antibody and antigen, and a standardized buffer.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

Preferably, binding of an antibody against a tumor antigen to cells expressing the tumor antigen induces or mediates killing of cells expressing the tumor antigen. The cells expressing a tumor antigen are preferably cancer cells and are, in particular, cells of the cancer diseases described herein. Preferably, the antibody induces or mediates killing of cells by inducing one or more of complement dependent cytotoxicity (CDC) mediated lysis, antibody dependent cellular cytotoxicity (ADCC) mediated lysis, apoptosis, and inhibition of proliferation of cells expressing a tumor antigen. Preferably, ADCC mediated lysis of cells takes place in the presence of effector cells, which in particular embodiments are selected from the group consisting of monocytes, mononuclear cells, NK cells and PMNs. Inhibiting proliferation of cells can be measured in vitro by determining proliferation of cells in an assay using bromodeoxyuridine (5-bromo-2'-deoxyuridine, BrdU). BrdU is a synthetic nucleoside which is an analogue of thymidine and can be incorporated into the newly synthesized DNA of replicating cells (during the S phase of the cell cycle), substituting for thymidine during DNA replication. Detecting the incorporated chemical using, for example, antibodies specific for BrdU indicates cells that were actively replicating their DNA.

In preferred embodiments, antibodies described herein can be characterized by one or more of the following properties:
a) specificity for a tumor antigen;
b) a binding affinity to a tumor antigen of about 100 nM or less, preferably, about 5-10 nM or less and, more preferably, about 1-3 nM or less,
c) the ability to induce or mediate CDC on tumor antigen positive cells;
d) the ability to induce or mediate ADCC on tumor antigen positive cells;
e) the ability to inhibit the growth of tumor antigen positive cells;
f) the ability to induce apoptosis of tumor antigen positive cells.

In one embodiment, an antibody against a tumor antigen has the ability of binding to an epitope present in the tumor antigen, preferably an epitope located within the extracellular domains of the tumor antigen. Preferably, an antibody against a tumor antigen is specific for the tumor antigen. Preferably, an antibody against a tumor antigen binds to the tumor antigen expressed on the cell surface. In particular preferred embodiments, an antibody against a tumor antigen binds to native epitopes of the tumor antigen present on the surface of living cells.

According to the invention an antibody having the ability of binding to CLDN18.2 or an antibody against CLDN18.2 is an antibody capable of binding to an epitope present in CLDN18.2, preferably an epitope located within the extracellular domains of CLDN18.2, in particular the first extracellular domain, preferably amino acid positions 29 to 78 of CLDN18.2. In particular embodiments, an antibody having the ability of binding to CLDN18.2 is an antibody capable of binding to (i) an epitope on CLDN18.2 which is not present on CLDN18.1, preferably SEQ ID NO: 3, 4, and 5, (ii) an epitope localized on the CLDN18.2-loop1, preferably SEQ ID NO: 8, (iii) an epitope localized on the CLDN18.2-loop2, preferably SEQ ID NO: 10, (iv) an epitope localized on the CLDN18.2-loopD3, preferably SEQ ID NO: 11, (v) an epitope, which encompass CLDN18.2-loop1 and CLDN18.2-loopD3, or (vi) a non-glycosylated epitope localized on the CLDN18.2-loopD3, preferably SEQ ID NO: 9.

According to the invention an antibody having the ability of binding to CLDN18.2 preferably is an antibody having the ability of binding to CLDN18.2 but not to CLDN18.1. Preferably, an antibody having the ability of binding to CLDN18.2 is specific for CLDN18.2. Preferably, an antibody having the ability of binding to CLDN18.2 is an antibody having the ability of binding to CLDN18.2 expressed on the cell surface. In particular preferred embodiments, an antibody having the ability of binding to CLDN18.2 binds to native epitopes of CLDN18.2 present on the surface of living cells. Preferably, an antibody having the ability of binding to CLDN18.2 binds to one or more peptides selected from the group consisting of SEQ ID NOs: 1, 3-11, 44, 46, and 48-50. Preferably, an antibody having the ability of binding to CLDN18.2 is specific for the aforementioned proteins, peptides or immunogenic fragments or derivatives thereof. An antibody having the ability of binding to CLDN18.2 may be obtained by a method comprising the step of immunizing an animal with a protein or peptide comprising an amino acid sequence selected from the group consisting of SEQ ID NOs: 1, 3-11, 44, 46, and 48-50, or a nucleic acid or host cell expressing said protein or peptide. Preferably, the antibody binds to cancer cells, in particular cells of the cancer types mentioned above and, preferably, does not bind substantially to non-cancerous cells.

Preferably, binding of an antibody having the ability of binding to CLDN18.2 to cells expressing CLDN18.2 induces or mediates killing of cells expressing CLDN18.2. The cells expressing CLDN18.2 are preferably cancer cells and are, in particular, selected from the group consisting of tumorigenic gastric, esophageal, pancreatic, lung, ovarian, colon, hepatic, head-neck, and gallbladder cancer cells. Preferably, the antibody induces or mediates killing of cells by inducing one or more of complement dependent cytotoxicity (CDC) mediated lysis, antibody dependent cellular cytotoxicity (ADCC) mediated lysis, apoptosis, and inhibition of proliferation of cells expressing CLDN18.2. Preferably, ADCC mediated lysis of cells takes place in the presence of effector cells, which in particular embodiments are selected from the group consisting of monocytes, mononuclear cells, NK cells and PMNs.

In preferred embodiments, an antibody having the ability of binding to CLDN18.2 can be characterized by one or more of the following properties:
a) specificity for CLDN18.2;
b) a binding affinity to CLDN18.2 of about 100 nM or less, preferably, about 5-10 nM or less and, more preferably, about 1-3 nM or less,
c) the ability to induce or mediate CDC on CLDN18.2 positive cells;
d) the ability to induce or mediate ADCC on CLDN18.2 positive cells;
e) the ability to inhibit the growth of CLDN18.2 positive cells;
f) the ability to induce apoptosis of CLDN18.2 positive cells.

In a particularly preferred embodiment, an antibody having the ability of binding to CLDN18.2 is produced by a hybridoma deposited at the DSMZ (Mascheroder Weg 1b, 31824 Braunschweig, Germany; new address: Inhoffenstr. 7B, 31824 Braunschweig, Germany) and having the following designation and accession number:
  a. 182-D1106-055, accession no. DSM ACC2737, deposited on Oct. 19, 2005
  b. 182-D1106-056, accession no. DSM ACC2738, deposited on Oct. 19, 2005
  c. 182-D1106-057, accession no. DSM ACC2739, deposited on Oct. 19, 2005
  d. 182-D1106-058, accession no. DSM ACC2740, deposited on Oct. 19, 2005
  e. 182-D1106-059, accession no. DSM ACC2741, deposited on Oct. 19, 2005
  f. 182-D1106-062, accession no. DSM ACC2742, deposited on Oct. 19, 2005,
  g. 182-D1106-067, accession no. DSM ACC2743, deposited on Oct. 19, 2005
  h. 182-D758-035, accession no. DSM ACC2745, deposited on Nov. 17, 2005
  i. 182-D758-036, accession no. DSM ACC2746, deposited on Nov. 17, 2005
  j. 182-D758-040, accession no. DSM ACC2747, deposited on Nov. 17, 2005
  k. 182-D1106-061, accession no. DSM ACC2748, deposited on Nov. 17, 2005
  l. 182-D1106-279, accession no. DSM ACC2808, deposited on Oct. 26, 2006
  m. 182-D1106-294, accession no. DSM ACC2809, deposited on Oct. 26, 2006,
  n. 182-D1106-362, accession no. DSM ACC2810, deposited on Oct. 26, 2006.

Preferred antibodies according to the invention are those produced by and obtainable from the above-described hybridomas; i.e. 37G11 in the case of 182-D1106-055, 37H8 in the case of 182-D1106-056, 38G5 in the case of 182-D1106-057, 38H3 in the case of 182-D1106-058, 39F11 in the case of 182-D1106-059, 43A11 in the case of 182-D1106-062, 61C2 in the case of 182-D1106-067, 26B5 in the case of 182-D758-035, 26D12 in the case of 182-D758-036, 28D10 in the case of 182-D758-040, 42E12 in the case of 182-D1106-061, 125E1 in the case of 182-D1106-279, 163E12 in the case of 182-D1106-294, and 175D10 in the case of 182-D1106-362; and the chimerized and humanized forms thereof.

In one embodiment, an antibody having the ability of binding to CLDN18.2 is an antibody selected from the group consisting of (i) an antibody produced by and/or obtainable from a clone deposited under the accession no. DSM ACC2737, DSM ACC2738, DSM ACC2739, DSM ACC2740, DSM ACC2741, DSM ACC2742, DSM ACC2743, DSM ACC2745, DSM ACC2746, DSM ACC2747, DSM ACC2748, DSM ACC2808, DSM ACC2809, or DSM ACC2810, (ii) an antibody which is a chimerized or humanized form of the antibody under (i), (iii) an antibody having the specificity of the antibody under (i), and (iv) an antibody comprising the antigen binding portion or antigen binding site, in particular the variable region, of the antibody under (i) and preferably having the specificity of the antibody under (i).

Preferred chimerized antibodies and their sequences are shown in the following table.

| | clone | mAb | Isotype | variable region | chimerized antibody |
|---|---|---|---|---|---|
| heavy chain | 43A11 | 182-D1106-062 | IgG2a | SEQ ID NO: 29 | SEQ ID NO: 14 |
| | 163E12 | 182-D1106-294 | IgG3 | SEQ ID NO: 30 | SEQ ID NO: 15 |
| | 125E1 | 182-D1106-279 | IgG2a | SEQ ID NO: 31 | SEQ ID NO: 16 |
| | 166E2 | 182-D1106-308 | IgG3 | SEQ ID NO: 33 | SEQ ID NO: 18 |
| | 175D10 | 182-D1106-362 | IgG1 | SEQ ID NO: 32 | SEQ ID NO: 17 |
| | 45C1 | 182-D758-187 | IgG2a | SEQ ID NO: 34 | SEQ ID NO: 19 |
| light chain | 43A11 | 182-D1106-062 | IgK | SEQ ID NO: 36 | SEQ ID NO: 21 |
| | 163E12 | 182-D1106-294 | IgK | SEQ ID NO: 35 | SEQ ID NO: 20 |
| | 125E1 | 182-D1106-279 | IgK | SEQ ID NO: 37 | SEQ ID NO: 22 |
| | 166E2 | 182-D1106-308 | IgK | SEQ ID NO: 40 | SEQ ID NO: 25 |
| | 175D10 | 182-D1106-362 | IgK | SEQ ID NO: 39 | SEQ ID NO: 24 |
| | 45C1 | 182-D758-187 | IgK | SEQ ID NO: 38 | SEQ ID NO: 23 |
| | 45C1 | 182-D758-187 | IgK | SEQ ID NO: 41 | SEQ ID NO: 26 |
| | 45C1 | 182-D758-187 | IgK | SEQ ID NO: 42 | SEQ ID NO: 27 |
| | 45C1 | 182-D758-187 | IgK | SEQ ID NO: 43 | SEQ ID NO: 28 |

In preferred embodiments, antibodies, in particular chimerised forms of antibodies according to the invention include antibodies comprising a heavy chain constant region (CH) comprising an amino acid sequence derived from a human heavy chain constant region such as the amino acid sequence represented by SEQ ID NO: 13 or a fragment thereof. In further preferred embodiments, antibodies, in particular chimerised forms of antibodies according to the invention include antibodies comprising a light chain constant region (CL) comprising an amino acid sequence derived from a human light chain constant region such as the amino acid sequence represented by SEQ ID NO: 12 or a fragment thereof. In a particular preferred embodiment, antibodies, in particular chimerised forms of antibodies according to the invention include antibodies which comprise a CH comprising an amino acid sequence derived from a human CH such as the amino acid sequence represented by SEQ ID NO: 13 or a fragment thereof and which comprise a CL comprising an amino acid sequence derived from a human CL such as the amino acid sequence represented by SEQ ID NO: 12 or a fragment thereof.

In one embodiment, an antibody having the ability of binding to CLDN18.2 is a chimeric mouse/human IgG1 monoclonal antibody comprising kappa, murine variable light chain, human kappa light chain constant region allotype Km(3), murine heavy chain variable region, human IgG1 constant region, allotype G1m(3).

In certain preferred embodiments, chimerised forms of antibodies include antibodies comprising a heavy chain comprising an amino acid sequence selected from the group consisting of SEQ ID NOs: 14, 15, 16, 17, 18, 19, 51, and a fragment thereof and/or comprising a light chain comprising an amino acid sequence selected from the group consisting of SEQ ID NOs: 20, 21, 22, 23, 24, 25, 26, 27, 28, and a fragment thereof.

In certain preferred embodiments, chimerised forms of antibodies include antibodies comprising a combination of heavy chains and light chains selected from the following possibilities (i) to (ix):
(i) the heavy chain comprises an amino acid sequence represented by SEQ ID NO: 14 or a fragment thereof and the light chain comprises an amino acid sequence represented by SEQ ID NO: 21 or a fragment thereof,
(ii) the heavy chain comprises an amino acid sequence represented by SEQ ID NO: 15 or a fragment thereof and the light chain comprises an amino acid sequence represented by SEQ ID NO: 20 or a fragment thereof,
(iii) the heavy chain comprises an amino acid sequence represented by SEQ ID NO: 16 or a fragment thereof and the light chain comprises an amino acid sequence represented by SEQ ID NO: 22 or a fragment thereof,
(iv) the heavy chain comprises an amino acid sequence represented by SEQ ID NO: 18 or a fragment thereof and the light chain comprises an amino acid sequence represented by SEQ ID NO: 25 or a fragment thereof,
(v) the heavy chain comprises an amino acid sequence represented by SEQ ID NO: 17 or a fragment thereof and the light chain comprises an amino acid sequence represented by SEQ ID NO: 24 or a fragment thereof,
(vi) the heavy chain comprises an amino acid sequence represented by SEQ ID NO: 19 or a fragment thereof and the light chain comprises an amino acid sequence represented by SEQ ID NO: 23 or a fragment thereof,
(vii) the heavy chain comprises an amino acid sequence represented by SEQ ID NO: 19 or a fragment thereof and the light chain comprises an amino acid sequence represented by SEQ ID NO: 26 or a fragment thereof,
(viii) the heavy chain comprises an amino acid sequence represented by SEQ ID NO: 19 or a fragment thereof and the light chain comprises an amino acid sequence represented by SEQ ID NO: 27 or a fragment thereof,
(ix) the heavy chain comprises an amino acid sequence represented by SEQ ID NO: 19 or a fragment thereof and the light chain comprises an amino acid sequence represented by SEQ ID NO: 28 or a fragment thereof, and
(x) the heavy chain comprises an amino acid sequence represented by SEQ ID NO: 51 or a fragment thereof and the light chain comprises an amino acid sequence represented by SEQ ID NO: 24 or a fragment thereof.

The antibody according to (v) or (x) is particularly preferred.

"Fragment" or "fragment of an amino acid sequence" as used above relates to a part of an antibody sequence, i.e. a sequence which represents the antibody sequence shortened at the N- and/or C-terminus, which when it replaces said antibody sequence in an antibody retains binding of said antibody to CLDN18.2 and preferably functions of said antibody as described herein, e.g. CDC mediated lysis or ADCC mediated lysis. Preferably, a fragment of an amino acid sequence comprises at least 80%, preferably at least 90%, 95%, 96%, 97%, 98%, or 99% of the amino acid residues from said amino acid sequence. A fragment of an amino acid sequence selected from the group consisting of SEQ ID NOs: 14, 15, 16, 17, 18, 19, 51, 20, 21, 22, 23, 24, 25, 26, 27, and 28 preferably relates to said sequence wherein 17, 18, 19, 20, 21, 22 or 23 amino acids at the N-terminus are removed.

In a preferred embodiment, an antibody having the ability of binding to CLDN18.2 comprises a heavy chain variable region (VH) comprising an amino acid sequence selected from the group consisting of SEQ ID NOs: 29, 30, 31, 32, 33, 34, and a fragment thereof.

In a preferred embodiment, an antibody having the ability of binding to CLDN18.2 comprises a light chain variable region (VL) comprising an amino acid sequence selected from the group consisting of SEQ ID NO: 35, 36, 37, 38, 39, 40, 41, 42, 43, and a fragment thereof.

In certain preferred embodiments, an antibody having the ability of binding to CLDN18.2 comprises a combination of heavy chain variable region (VH) and light chain variable region (VL) selected from the following possibilities (i) to (ix):
(i) the VH comprises an amino acid sequence represented by SEQ ID NO: 29 or a fragment thereof and the VL comprises an amino acid sequence represented by SEQ ID NO: 36 or a fragment thereof,
(ii) the VH comprises an amino acid sequence represented by SEQ ID NO: 30 or a fragment thereof and the VL comprises an amino acid sequence represented by SEQ ID NO: 35 or a fragment thereof,
(iii) the VH comprises an amino acid sequence represented by SEQ ID NO: 31 or a fragment thereof and the VL comprises an amino acid sequence represented by SEQ ID NO: 37 or a fragment thereof,
(iv) the VH comprises an amino acid sequence represented by SEQ ID NO: 33 or a fragment thereof and the VL comprises an amino acid sequence represented by SEQ ID NO: 40 or a fragment thereof,
(v) the VH comprises an amino acid sequence represented by SEQ ID NO: 32 or a fragment thereof and the VL comprises an amino acid sequence represented by SEQ ID NO: 39 or a fragment thereof,
(vi) the VH comprises an amino acid sequence represented by SEQ ID NO: 34 or a fragment thereof and the VL comprises an amino acid sequence represented by SEQ ID NO: 38 or a fragment thereof,
(vii) the VH comprises an amino acid sequence represented by SEQ ID NO: 34 or a fragment thereof and the VL comprises an amino acid sequence represented by SEQ ID NO: 41 or a fragment thereof,
(viii) the VH comprises an amino acid sequence represented by SEQ ID NO: 34 or a fragment thereof and the VL comprises an amino acid sequence represented by SEQ ID NO: 42 or a fragment thereof,
(ix) the VH comprises an amino acid sequence represented by SEQ ID NO: 34 or a fragment thereof and the VL comprises an amino acid sequence represented by SEQ ID NO: 43 or a fragment thereof.

The antibody according to (v) is particularly preferred.

According to the invention, the term "fragment" refers, in particular, to one or more of the complementarity-determining regions (CDRs), preferably at least the CDR3 variable region, of the heavy chain variable region (VH) and/or of the light chain variable region (VL). In one embodiment said one or more of the complementarity-determining regions (CDRs) are selected from a set of complementarity-determining regions CDR1, CDR2 and CDR3. In a particularly preferred embodiment, the term "fragment" refers to the complementarity-determining regions CDR1, CDR2 and CDR3 of the heavy chain variable region (VH) and/or of the light chain variable region (VL).

In a preferred embodiment, an antibody having the ability of binding to CLDN18.2 comprises a VH comprising a set of complementarity-determining regions CDR1, CDR2 and CDR3 selected from the following embodiments (i) to (vi):
  (i) CDR1: positions 45-52 of SEQ ID NO: 14, CDR2: positions 70-77 of SEQ ID NO: 14, CDR3: positions 116-125 of SEQ ID NO: 14,
  (ii) CDR1: positions 45-52 of SEQ ID NO: 15, CDR2: positions 70-77 of SEQ ID NO: 15, CDR3: positions 116-126 of SEQ ID NO: 15,
  (iii) CDR1: positions 45-52 of SEQ ID NO: 16, CDR2: positions 70-77 of SEQ ID NO: 16, CDR3: positions 116-124 of SEQ ID NO: 16,
  (iv) CDR1: positions 45-52 of SEQ ID NO: 17, CDR2: positions 70-77 of SEQ ID NO: 17, CDR3: positions 116-126 of SEQ ID NO: 17,
  (v) CDR1: positions 44-51 of SEQ ID NO: 18, CDR2: positions 69-76 of SEQ ID NO: 18, CDR3: positions 115-125 of SEQ ID NO: 18, and
  (vi) CDR1: positions 45-53 of SEQ ID NO: 19, CDR2: positions 71-78 of SEQ ID NO: 19, CDR3: positions 117-128 of SEQ ID NO: 19.

In a preferred embodiment, an antibody having the ability of binding to CLDN18.2 comprises a VL comprising a set of complementarity-determining regions CDR1, CDR2 and CDR3 selected from the following embodiments (i) to (ix):
  (i) CDR1: positions 47-58 of SEQ ID NO: 20, CDR2: positions 76-78 of SEQ ID NO: 20, CDR3: positions 115-123 of SEQ ID NO: 20,
  (ii) CDR1: positions 49-53 of SEQ ID NO: 21, CDR2: positions 71-73 of SEQ ID NO: 21, CDR3: positions 110-118 of SEQ ID NO: 21,
  (iii) CDR1: positions 47-52 of SEQ ID NO: 22, CDR2: positions 70-72 of SEQ ID NO: 22, CDR3: positions 109-117 of SEQ ID NO: 22,
  (iv) CDR1: positions 47-58 of SEQ ID NO: 23, CDR2: positions 76-78 of SEQ ID NO: 23, CDR3: positions 115-123 of SEQ ID NO: 23,
  (v) CDR1: positions 47-58 of SEQ ID NO: 24, CDR2: positions 76-78 of SEQ ID NO: 24, CDR3: positions 115-123 of SEQ ID NO: 24,
  (vi) CDR1: positions 47-58 of SEQ ID NO: 25, CDR2: positions 76-78 of SEQ ID NO: 25, CDR3: positions 115-122 of SEQ ID NO: 25,
  (vii) CDR1: positions 47-58 of SEQ ID NO: 26, CDR2: positions 76-78 of SEQ ID NO: 26, CDR3: positions 115-123 of SEQ ID NO: 26,
  (viii) CDR1: positions 47-58 of SEQ ID NO: 27, CDR2: positions 76-78 of SEQ ID NO: 27, CDR3: positions 115-123 of SEQ ID NO: 27, and
  (ix) CDR1: positions 47-52 of SEQ ID NO: 28, CDR2: positions 70-72 of SEQ ID NO: 28, CDR3: positions 109-117 of SEQ ID NO: 28.

In a preferred embodiment, an antibody having the ability of binding to CLDN18.2 comprises a combination of VH and VL each comprising a set of complementarity-determining regions CDR1, CDR2 and CDR3 selected from the following embodiments (i) to (ix):
  (i) VH: CDR1: positions 45-52 of SEQ ID NO: 14, CDR2: positions 70-77 of SEQ ID NO: 14, CDR3: positions 116-125 of SEQ ID NO: 14, VL: CDR1: positions 49-53 of SEQ ID NO: 21, CDR2: positions 71-73 of SEQ ID NO: 21, CDR3: positions 110-118 of SEQ ID NO: 21,
  (ii) VH: CDR1: positions 45-52 of SEQ ID NO: 15, CDR2: positions 70-77 of SEQ ID NO: 15, CDR3: positions 116-126 of SEQ ID NO: 15, VL: CDR1: positions 47-58 of SEQ ID NO: 20, CDR2: positions 76-78 of SEQ ID NO: 20, CDR3: positions 115-123 of SEQ ID NO: 20,
  (iii) VH: CDR1: positions 45-52 of SEQ ID NO: 16, CDR2: positions 70-77 of SEQ ID NO: 16, CDR3: positions 116-124 of SEQ ID NO: 16, VL: CDR1: positions 47-52 of SEQ ID NO: 22, CDR2: positions 70-72 of SEQ ID NO: 22, CDR3: positions 109-117 of SEQ ID NO: 22,
  (iv) VH: CDR1: positions 44-51 of SEQ ID NO: 18, CDR2: positions 69-76 of SEQ ID NO: 18, CDR3: positions 115-125 of SEQ ID NO: 18, VL: CDR1: positions 47-58 of SEQ ID NO: 25, CDR2: positions 76-78 of SEQ ID NO: 25, CDR3: positions 115-122 of SEQ ID NO: 25,
  (v) VH: CDR1: positions 45-52 of SEQ ID NO: 17, CDR2: positions 70-77 of SEQ ID NO: 17, CDR3: positions 116-126 of SEQ ID NO: 17, VL: CDR1: positions 47-58 of SEQ ID NO: 24, CDR2: positions 76-78 of SEQ ID NO: 24, CDR3: positions 115-123 of SEQ ID NO: 24,
  (vi) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-58 of SEQ ID NO: 23, CDR2: positions 76-78 of SEQ ID NO: 23, CDR3: positions 115-123 of SEQ ID NO: 23,
  (vii) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-58 of SEQ ID NO: 26, CDR2: positions 76-78 of SEQ ID NO: 26, CDR3: positions 115-123 of SEQ ID NO: 26,
  (viii) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-58 of SEQ ID NO: 27, CDR2: positions 76-78 of SEQ ID NO: 27, CDR3: positions 115-123 of SEQ ID NO: 27, and
  (ix) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-52 of SEQ ID NO: 28, CDR2: positions 70-72 of SEQ ID NO: 28, CDR3: positions 109-117 of SEQ ID NO: 28.

In further preferred embodiments, an antibody having the ability of binding to CLDN18.2 preferably comprises one or more of the complementarity-determining regions (CDRs), preferably at least the CDR3 variable region, of the heavy chain variable region (VH) and/or of the light chain variable region (VL) of a monoclonal antibody against CLDN18.2, preferably of a monoclonal antibody against CLDN18.2 described herein, and preferably comprises one or more of the complementarity-determining regions (CDRs), preferably at least the CDR3 variable region, of the heavy chain variable regions (VH) and/or light chain variable regions (VL) described herein. In one embodiment said one or more of the complementarity-determining regions (CDRs) are selected from a set of complementarity-determining regions CDR1, CDR2 and CDR3 described herein. In a particularly preferred embodiment, an antibody having the ability of binding to CLDN18.2 preferably comprises the complementarity-determining regions CDR1, CDR2 and CDR3 of the heavy chain variable region (VH) and/or of the light chain variable region (VL) of a monoclonal antibody against CLDN18.2, preferably of a monoclonal antibody against CLDN18.2 described herein, and preferably comprises the complementarity-determining regions CDR1, CDR2 and CDR3 of the heavy chain variable regions (VH) and/or light chain variable regions (VL) described herein.

In one embodiment an antibody comprising one or more CDRs, a set of CDRs or a combination of sets of CDRs as described herein comprises said CDRs together with their intervening framework regions. Preferably, the portion will also include at least about 50% of either or both of the first and fourth framework regions, the 50% being the C-terminal 50% of the first framework region and the N-terminal 50% of the fourth framework region. Construction of antibodies made by recombinant DNA techniques may result in the introduction of residues N- or C-terminal to the variable regions encoded by linkers introduced to facilitate cloning or other manipulation steps, including the introduction of linkers to join variable regions of the invention to further protein sequences including immunoglobulin heavy chains, other variable domains (for example in the production of diabodies) or protein labels.

In one embodiment an antibody comprising one or more CDRs, a set of CDRs or a combination of sets of CDRs as described herein comprises said CDRs in a human antibody framework.

Reference herein to an antibody comprising with respect to the heavy chain thereof a particular chain, or a particular region or sequence preferably relates to the situation wherein all heavy chains of said antibody comprise said particular chain, region or sequence. This applies correspondingly to the light chain of an antibody.

It is to be understood that the antibodies described herein may be delivered to a patient by administering a nucleic acid such as RNA encoding the antibody and/or by administering a host cell comprising a nucleic acid such as RNA encoding the antibody. Thus, a nucleic acid encoding an antibody when administered to a patient may be present in naked form or in a suitable delivery vehicle such as in the form of liposomes or viral particles, or within a host cell. The nucleic acid provided can produce the antibody over extended time periods in a sustained manner mitigating the instability at least partially observed for therapeutic antibodies. Nucleic acids to be delivered to a patient can be produced by recombinant means. If a nucleic acid is administered to a patient without being present within a host cell, it is preferably taken up by cells of the patient for expression of the antibody encoded by the nucleic acid. If a nucleic acid is administered to a patient while being present within a host cell, it is preferably expressed by the host cell within the patient so as to produce the antibody encoded by the nucleic acid.

The term "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA.

Nucleic acids may be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a 0-D-ribofuranosyl group. The term includes double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region (5'-UTR), a protein or peptide coding region and a 3' non translated region (3'-UTR). mRNA has a limited half-time in cells and in vitro. Preferably, mRNA is produced by in vitro transcription using a DNA template. In one embodiment of the invention, the RNA is obtained by in vitro transcription or chemical synthesis. The in vitro transcription methodology is known to the skilled person. For example, there is a variety of in vitro transcription kits commercially available.

In order to increase expression and/or stability of the RNA used according to the present invention, it may be modified, preferably without altering the sequence of the expressed peptide or protein.

The term "modification" in the context of RNA as used according to the present invention includes any modification of RNA which is not naturally present in said RNA. Such modified RNA is encompassed herein by the term "RNA".

For example, the RNA according to the invention may have modified naturally occurring or synthetic ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap (m7G). In the context of the present invention, the term "5'-cap" includes a 5'-cap analog that resembles the RNA cap structure and is modified to possess the ability to stabilize RNA if attached thereto, preferably in vivo and/or in a cell.

Preferably, RNA if delivered to, i.e. transfected into, a cell, in particular a cell present in vivo, expresses the protein or peptide it encodes.

The term "transfection" relates to the introduction of nucleic acids, in particular RNA, into a cell. For purposes of the present invention, the term "transfection" also includes the introduction of a nucleic acid into a cell or the uptake of a nucleic acid by such cell, wherein the cell may be present in a subject, e.g., a patient. Thus, according to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded protein.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector".

The term "translation" according to the invention relates to the process in the ribosomes of a cell by which a strand of messenger RNA directs the assembly of a sequence of amino acids to make a peptide or protein.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa. In some embodiments, a tumor antigen may also be specifically expressed under normal conditions in more than one tissue type or organ, such as in 2 or 3 tissue types or organs, but preferably in not more than 3 different tissue or organ types. In this case, the tumor antigen is then specifically expressed in these organs. For example, if a tumor antigen is expressed under normal conditions preferably to an approximately equal extent in lung and stomach, said tumor antigen is specifically expressed in lung and stomach.

According to the invention, the term "RNA encoding" means that RNA, if present in the appropriate environment, preferably within a cell, can be expressed to produce a protein or peptide it encodes.

Some aspects of the invention rely on the adoptive transfer of host cells which are transfected in vitro with a nucleic acid such as RNA encoding an antibody described herein and transferred to recipients such as patients, preferably after ex vivo expansion from low precursor frequencies to clinically relevant cell numbers. The host cells used for treatment according to the invention may be autologous, allogeneic, or syngeneic to a treated recipient.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues.

The term "heterologous" is used to describe something consisting of multiple different elements. As an example, the transfer of one individual's bone marrow into a different individual constitutes a heterologous transplant. A heterologous gene is a gene derived from a source other than the subject.

The term "peptide" according to the invention comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

The teaching given herein with respect to specific amino acid sequences, e.g. those shown in the sequence listing, is to be construed so as to also relate to variants of said specific sequences resulting in sequences which are functionally equivalent to said specific sequences, e.g. amino acid sequences exhibiting properties identical or similar to those of the specific amino acid sequences.

One important property is to retain binding of an antibody to its target or to sustain effector functions of an antibody. Preferably, a sequence which is a variant with respect to a specific sequence, when it replaces the specific sequence in an antibody retains binding of said antibody to its target and preferably functions of said antibody as described herein, e.g. CDC mediated lysis or ADCC mediated lysis.

It will be appreciated by those skilled in the art that in particular the sequences of the CDR, hypervariable and variable regions can be modified without losing the ability of an antibody to bind to its target. For example, CDR regions will be either identical or highly homologous to the regions of antibodies specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions of antibodies specifically disclosed herein.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl. Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transfected with an exogenous nucleic acid. Preferably, the cell when transfected with an exogenous nucleic acid and transferred to a recipient can express the nucleic acid in the recipient. The term "cell" includes bacterial cells; other useful cells are yeast cells, fungal cells or mammalian cells. Suitable bacterial cells include cells from gram-negative bacterial strains such as strains of Escherichia coli, Proteus, and Pseudomonas, and gram-positive bacterial strains such as strains of Bacillus, Streptomyces, Staphylococcus, and Lactococcus. Suitable fungal cell include cells from species of Trichoderma, Neurospora, and Aspergillus. Suitable yeast cells include cells from species of Saccharomyces (Tor example Saccharomyces cerevisiae), Schizosaccharomyces (for example Schizo saccharomyces pombe), Pichia (for example Pichia pastoris and Pichia methanolicd), and Hansenula. Suitable mammalian cells include for example CHO cells, BHK cells, HeLa cells, COS cells, 293 HEK and the like. However, amphibian cells, insect cells, plant cells, and any other cells used in the art for the expression of heterologous proteins can be used as well. Mammalian cells are particularly preferred for adoptive transfer, such as cells from humans, mice, hamsters, pigs, goats, and primates. The cells may be derived from a large number of tissue types and include primary cells and cell lines such as cells of the immune system, in particular antigen-presenting cells such as dendritic cells and T cells, stem cells such as hematopoietic stem cells and mesenchymal stem cells and other cell types. An antigen-presenting cell is a cell that displays antigen in the context of major histocompatibility complex on its surface. T cells may recognize this complex using their T cell receptor (TCR).

The term "transgenic animal" refers to an animal having a genome comprising one or more transgenes, preferably heavy and/or light chain transgenes, or transchromosomes (either integrated or non-integrated into the animal's natural genomic DNA) and which is preferably capable of expressing the transgenes. For example, a transgenic mouse can have a human light chain transgene and either a human heavy chain transgene or human heavy chain transchromosome, such that the mouse produces human anti-tumor antigen antibodies when immunized with a tumor antigen and/or cells expressing a tumor antigen. The human heavy chain transgene can be integrated into the chromosomal DNA of the mouse, as is the case for transgenic mice, e.g., HuMAb mice, such as HCo7 or HCo12 mice, or the human heavy chain transgene can be maintained extrachromosomally, as is the case for transchromosomal (e.g., KM) mice as described in WO 02/43478. Such transgenic and transchromosomal mice may be capable of producing multiple isotypes of human monoclonal antibodies to a tumor antigen (e.g., IgG, IgA and/or IgE) by undergoing V-D-J recombination and isotype switching.

"Reduce", "decrease" or "inhibit" as used herein means an overall decrease or the ability to cause an overall decrease, preferably of 5% or greater, 10% or greater, 20% or greater, more preferably of 50% or greater, and most preferably of 75% or greater, in the level, e.g. in the level of expression or in the level of proliferation of cells.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%, at least 200%, at least 500%, at least 1000%, at least 10000% or even more.

Antibodies described herein can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

In yet another preferred embodiment, human monoclonal antibodies can be generated using transgenic or transchromosomal mice carrying parts of the human immune system rather than the mouse system. These transgenic and transchromosomic mice include mice known as HuMAb mice and KM mice, respectively, and are collectively referred to herein as "transgenic mice." The production of human antibodies in such transgenic mice can be performed as described in detail for CD20 in WO2004 035607.

Yet another strategy for generating monoclonal antibodies is to directly isolate genes encoding antibodies from lymphocytes producing antibodies of defined specificity e.g. see Babcock et al., 1996; A novel strategy for generating monoclonal antibodies from single, isolated lymphocytes producing antibodies of defined specificities. For details of recombinant antibody engineering see also Welschof and Kraus, Recombinant antibodies for cancer therapy ISBN-0-89603-918-8 and Benny K. C. Lo Antibody Engineering ISBN 1-58829-092-1.

To generate antibodies, mice can be immunized with carrier-conjugated peptides derived from the antigen sequence, i.e. the sequence against which the antibodies are to be directed, an enriched preparation of recombinantly expressed antigen or fragments thereof and/or cells expressing the antigen, as described. Alternatively, mice can be immunized with DNA encoding the antigen or fragments thereof. In the event that immunizations using a purified or enriched preparation of the antigen do not result in antibodies, mice can also be immunized with cells expressing the antigen, e.g., a cell line, to promote immune responses.

The immune response can be monitored over the course of the immunization protocol with plasma and serum samples being obtained by tail vein or retroorbital bleeds. Mice with sufficient titers of immunoglobulin can be used for fusions. Mice can be boosted intraperitonealy or intravenously with antigen expressing cells 3 days before sacrifice and removal of the spleen to increase the rate of specific antibody secreting hybridomas.

To generate hybridomas producing monoclonal antibodies, splenocytes and lymph node cells from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using antigen expressing cells, antibodies with specificity for the antigen can be identified. The antibody secreting hybridomas can be replated, screened again, and if still positive for monoclonal antibodies can be subcloned by limiting dilution. The stable subclones can then be cultured in vitro to generate antibody in tissue culture medium for characterization.

Antibodies also can be produced in a host cell transfectoma using, for example, a combination of recombinant DNA techniques and gene transfection methods as are well known in the art (Morrison, S. (1985) Science 229: 1202).

For example, in one embodiment, the gene(s) of interest, e.g., antibody genes, can be ligated into an expression vector such as a eukaryotic expression plasmid such as used by the GS gene expression system disclosed in WO 87/04462, WO 89/01036 and EP 338 841 or other expression systems well known in the art. The purified plasmid with the cloned antibody genes can be introduced in eukaryotic host cells such as CHO cells, NS/0 cells, HEK293T cells or HEK293 cells or alternatively other eukaryotic cells like plant derived cells, fungal or yeast cells. The method used to introduce these genes can be methods described in the art such as electroporation, lipofectine, lipofectamine or others. After introduction of these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively, the cloned antibody genes can be expressed in other expression systems, including prokaryotic cells, such as microorganisms, e.g. $E.\ coli$. Furthermore, the antibodies can be produced in transgenic non-human animals, such as in milk from sheep and rabbits or in eggs from hens, or in transgenic plants; see e.g. Verma, R., et al. (1998) J. Immunol. Meth. 216: 165-181; Pollock, et al. (1999) J. Immunol. Meth. 231: 147-157; and Fischer, R., et al. (1999) Biol. Chem. 380: 825-839.

Chimerization

Murine antibodies are highly immunogenic in man when repetitively applied leading to reduction of the therapeutic effect. The main immunogenicity is mediated by the heavy chain constant regions. The immunogenicity of murine antibodies in man can be reduced or completely avoided if respective antibodies are chimerized or humanized. Chimeric antibodies are antibodies, the different portions of which are derived from different animal species, such as those having a variable region derived from a murine antibody and a human immunoglobulin constant region. Chimerisation of antibodies is achieved by joining of the variable regions of the murine antibody heavy and light chain with the constant region of human heavy and light chain (e.g. as described by Kraus et al., in Methods in Molecular Biology series, Recombinant antibodies for cancer therapy ISBN-0-89603-918-8). In a preferred embodiment chimeric antibodies are generated by joining human kappa-light chain constant region to murine light chain variable region. In an also preferred embodiment chimeric antibodies can be generated by joining human lambda-light chain constant region to murine light chain variable region. The preferred heavy chain constant regions for generation of chimeric antibodies are IgG1, IgG3 and IgG4. Other preferred heavy chain constant regions for generation of chimeric antibodies are IgG2, IgA, IgD and IgM.

Humanization

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332: 323-327; Jones, P. et al. (1986) Nature 321: 522-525; and Queen, C. et al. (1989) Proc. Natl. Acad. Sci. U.S.A. 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual evenly across the variable region.

The ability of antibodies to bind an antigen can be determined using standard binding assays (e.g., ELISA, Western Blot, Immunofluorescence and flow cytometric analysis).

To purify antibodies, selected hybridomas can be grown in two-liter spinner-flasks for monoclonal antibody purification. Alternatively, antibodies can be produced in dialysis based bioreactors. Supernatants can be filtered and, if necessary, concentrated before affinity chromatography with protein G-sepharose or protein A-sepharose. Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected monoclonal antibodies bind to unique epitopes, site-directed or multi-site directed mutagenesis can be used.

To determine the isotype of antibodies, isotype ELISAs with various commercial kits (e.g. Zymed, Roche Diagnostics) can be performed. Wells of microtiter plates can be coated with anti-mouse Ig. After blocking, the plates are reacted with monoclonal antibodies or purified isotype controls, at ambient temperature for two hours. The wells can then be reacted with either mouse IgG1, IgG2a, IgG2b or IgG3, IgA or mouse IgM-specific peroxidase-conjugated probes. After washing, the plates can be developed with ABTS substrate (1 mg/ml) and analyzed at OD of 405-650. Alternatively, the IsoStrip Mouse Monoclonal Antibody Isotyping Kit (Roche, Cat. No. 1493027) may be used as described by the manufacturer.

In order to demonstrate presence of antibodies in sera of immunized mice or binding of monoclonal antibodies to living cells expressing antigen, flow cytometry can be used.

Cell lines expressing naturally or after transfection antigen and negative controls lacking antigen expression (grown under standard growth conditions) can be mixed with various concentrations of monoclonal antibodies in hybridoma supernatants or in PBS containing 1% FBS, and can be incubated at 4° C. for 30 min. After washing, the APC- or Alexa647-labeled anti IgG antibody can bind to antigen-bound monoclonal antibody under the same conditions as the primary antibody staining. The samples can be analyzed by flow cytometry with a FACS instrument using light and side scatter properties to gate on single, living cells. In order to distinguish antigen-specific monoclonal antibodies from non-specific binders in a single measurement, the method of co-transfection can be employed. Cells transiently transfected with plasmids encoding antigen and a fluorescent marker can be stained as described above. Transfected cells can be detected in a different fluorescence channel than antibody-stained cells. As the majority of transfected cells express both transgenes, antigen-specific monoclonal antibodies bind preferentially to fluorescence marker expressing cells, whereas non-specific antibodies bind in a comparable ratio to non-transfected cells. An alternative assay using fluorescence microscopy may be used in addition to or instead of the flow cytometry assay. Cells can be stained exactly as described above and examined by fluorescence microscopy.

In order to demonstrate presence of antibodies in sera of immunized mice or binding of monoclonal antibodies to living cells expressing antigen, immunofluorescence microscopy analysis can be used. For example, cell lines expressing either spontaneously or after transfection antigen and negative controls lacking antigen expression are grown in chamber slides under standard growth conditions in DMEM/F12 medium, supplemented with 10% fetal calf serum (FCS), 2 mM L-glutamine, 100 IU/ml penicillin and 100 µg/ml streptomycin. Cells can then be fixed with methanol or paraformaldehyde or left untreated. Cells can then be reacted with monoclonal antibodies against the antigen for 30 min. at 25° C. After washing, cells can be reacted with an Alexa555-labelled anti-mouse IgG secondary antibody (Molecular Probes) under the same conditions. Cells can then be examined by fluorescence microscopy.

Cell extracts from cells expressing antigen and appropriate negative controls can be prepared and subjected to sodium dodecyl sulfate (SDS) polyacrylamide gel electrophoresis. After electrophoresis, the separated antigens will be transferred to nitrocellulose membranes, blocked, and probed with the monoclonal antibodies to be tested. IgG binding can be detected using anti-mouse IgG peroxidase and developed with ECL substrate.

Antibodies can be further tested for reactivity with antigen by Immunohistochemistry in a manner well known to the skilled person, e.g. using paraformaldehyde or acetone fixed cryosections or paraffin embedded tissue sections fixed with paraformaldehyde from non-cancer tissue or cancer tissue samples obtained from patients during routine surgical procedures or from mice carrying xenografted tumors inoculated with cell lines expressing spontaneously or after transfection antigen. For immunostaining, antibodies reactive to antigen can be incubated followed by horseradish-peroxidase conjugated goat anti-mouse or goat anti-rabbit antibodies (DAKO) according to the vendor's instructions.

Antibodies can be tested for their ability to mediate phagocytosis and killing of cells expressing a tumor antigen. The testing of monoclonal antibody activity in vitro will provide an initial screening prior to testing in vivo models.

Antibody Dependent Cell-Mediated Cytotoxicity (ADCC)

Briefly, polymorphonuclear cells (PMNs), NK cells, monocytes, mononuclear cells or other effector cells, from healthy donors can be purified by Ficoll Hypaque density centrifugation, followed by lysis of contaminating erythrocytes. Washed effector cells can be suspended in RPMI supplemented with 10% heat-inactivated fetal calf serum or, alternatively with 5% heat-inactivated human serum and mixed with $^{51}$Cr labeled target cells expressing a tumor antigen, at various ratios of effector cells to target cells. Alternatively, the target cells may be labeled with a fluorescence enhancing ligand (BATDA). A highly fluorescent chelate of Europium with the enhancing ligand which is released from dead cells can be measured by a fluorometer. Another alternative technique may utilize the transfection of target cells with luciferase. Added lucifer yellow may then be oxidized by viable cells only. Purified anti-tumor antigen IgGs can then be added at various concentrations. Irrelevant human IgG can be used as negative control. Assays can be carried out for 4 to 20 hours at 37° C. depending on the effector cell type used. Samples can be assayed for cytolysis by measuring $^{51}$Cr release or the presence of the EuTDA chelate in the culture supernatant. Alternatively, luminescence resulting from the oxidation of lucifer yellow can be a measure of viable cells.

Anti-tumor antigen monoclonal antibodies can also be tested in various combinations to determine whether cytolysis is enhanced with multiple monoclonal antibodies.

Complement Dependent Cytotoxicity (CDC)

Monoclonal anti-tumor antigen antibodies can be tested for their ability to mediate CDC using a variety of known techniques. For example, serum for complement can be obtained from blood in a manner known to the skilled person. To determine the CDC activity of mAbs, different methods can be used. $^{51}$Cr release can for example be measured or elevated membrane permeability can be assessed using a propidium iodide (PI) exclusion assay. Briefly, target cells can be washed and $5 \times 10^5$/ml can be incubated with various concentrations of mAb for 10-30 min. at room temperature or at 37° C. Serum or plasma can then be added to a final concentration of 20% (v/v) and the cells incubated at 37° C. for 20-30 min. All cells from each sample can be added to the PI solution in a FACS tube. The mixture can then be analyzed immediately by flow cytometry analysis using FACSArray.

In an alternative assay, induction of CDC can be determined on adherent cells. In one embodiment of this assay, cells are seeded 24 h before the assay with a density of $3 \times 10^4$/well in tissue-culture flat-bottom microtiter plates. The next day growth medium is removed and the cells are incubated in triplicates with antibodies. Control cells are incubated with growth medium or growth medium containing 0.2% saponin for the determination of background lysis and maximal lysis, respectively. After incubation for 20 min. at room temperature supernatant is removed and 20% (v/v) human plasma or serum in DMEM (prewarmed to 37° C.) is added to the cells and incubated for another 20 min. at 37° C. All cells from each sample are added to propidium iodide solution (10 µg/ml). Then, supernatants are replaced by PBS containing 2.5 µg/ml ethidium bromide and fluorescence emission upon excitation at 520 nm is measured at 600 nm using a Tecan Safire. The percentage specific lysis is calculated as follows: % specific lysis=(fluorescence sample–fluorescence background)/(fluorescence maximal lysis–fluorescence background)×100.

Induction of Apoptosis and Inhibition of Cell Proliferation by Monoclonal Antibodies To test for the ability to initiate apoptosis, monoclonal anti-tumor antigen antibodies can, for example, be incubated with tumor antigen positive tumor cells or tumor antigen transfected tumor cells at 37° C. for about 20 hours. The cells can be harvested, washed in Annexin-V binding buffer (BD biosciences), and incubated with Annexin V conjugated with FITC or APC (BD biosciences) for 15 min. in the dark. All cells from each sample can be added to PI solution (10 μg/ml in PBS) in a FACS tube and assessed immediately by flow cytometry (as above). Alternatively, a general inhibition of cell-proliferation by monoclonal antibodies can be detected with commercially available kits. The DELFIA Cell Proliferation Kit (Perkin-Elmer, Cat. No. AD0200) is a non-isotopic immunoassay based on the measurement of 5-bromo-2'-deoxyuridine (BrdU) incorporation during DNA synthesis of proliferating cells in microplates. Incorporated BrdU is detected using europium labelled monoclonal antibody. To allow antibody detection, cells are fixed and DNA denatured using Fix solution. Unbound antibody is washed away and DELFIA inducer is added to dissociate europium ions from the labelled antibody into solution, where they form highly fluorescent chelates with components of the DELFIA Inducer. The fluorescence measured—utilizing time-resolved fluorometry in the detection—is proportional to the DNA synthesis in the cell of each well.

Preclinical Studies

Antibodies described herein also can be tested in an in vivo model (e.g. in immune deficient mice carrying xenografted tumors inoculated with cell lines expressing a tumor antigen to determine their efficacy in controlling growth of tumor antigen-expressing tumor cells.

In vivo studies after xenografting tumor antigen expressing tumor cells into immunocompromised mice or other animals can be performed using antibodies described herein. Antibodies can be administered to tumor free mice followed by injection of tumor cells to measure the effects of the antibodies to prevent formation of tumors or tumor-related symptoms. Antibodies can be administered to tumor-bearing mice to determine the therapeutic efficacy of respective antibodies to reduce tumor growth, metastasis or tumor related symptoms. Antibody application can be combined with application of other substances as cystostatic drugs, growth factor inhibitors, cell cycle blockers, angiogenesis inhibitors or other antibodies to determine synergistic efficacy and potential toxicity of combinations. To analyze toxic side effects mediated by antibodies animals can be inoculated with antibodies or control reagents and thoroughly investigated for symptoms possibly related to tumor antigen-antibody therapy. Possible side effects of in vivo application of tumor antigen antibodies particularly include toxicity at tumor antigen expressing tissues. Antibodies recognizing a tumor antigen in human and in other species, e.g. mice, are particularly useful to predict potential side effects mediated by application of monoclonal tumor antigen-antibodies in humans.

Mapping of epitopes recognized by antibodies can be performed as described in detail in "Epitope Mapping Protocols (Methods in Molecular Biology) by Glenn E. Morris ISBN-089603-375-9 and in "Epitope Mapping: A Practical Approach" Practical Approach Series, 248 by Olwyn M. R. Westwood, Frank C. Hay.

The compounds and agents described herein may be administered in the form of any suitable pharmaceutical composition.

Pharmaceutical compositions are preferably sterile and contain an effective amount of the antibodies described herein and optionally of further agents as discussed herein to generate the desired reaction or the desired effect.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may be used for preparing pharmaceutically acceptable salts and are included in the invention. Pharmaceutically acceptable salts of this kind comprise in a non-limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

An injectible formulation may comprise a pharmaceutically acceptable excipient such as Ringer lactate.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavoring agents, or colorants.

The agents and compositions described herein may be administered via any conventional route, such as by parenteral administration including by injection or infusion. Administration is preferably parenterally, e.g. intravenously, intraarterially, subcutaneously, intradermally or intramuscularly.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. In particular, the term "effective amount" refers to the amount of a therapy that is sufficient to result in the prevention of the development, recurrence, or onset of cancer and one or more symptoms thereof, reduce the severity, the duration of cancer, ameliorate one or more symptoms of cancer, prevent the advancement of cancer, cause regression of cancer, and/or prevent cancer metastases. In an embodiment of the invention, the amount of a therapy is effective to achieve a stabilization, reduction or elimination of the cancer stem cell population and/or eradication, removal, or control of primary cancer, metastatic cancer and/or recurrent cancer.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on several of such parameters. In the case that a reaction in a patient is insufficient with an initial dose, higher doses (or effectively higher doses achieved by a different, more localized route of administration) may be used.

The agents and compositions provided herein may be used alone or in combination with conventional therapeutic regimens such as surgery, irradiation, chemotherapy and/or bone marrow transplantation (autologous, syngeneic, allogeneic or unrelated).

Treatment of cancer represents a field where combination strategies are especially desirable since frequently the combined action of two, three, four or even more cancer drugs/therapies generates synergistic effects which are considerably stronger than the impact of a monotherapeutic approach. Thus, in another embodiment of the present invention, a cancer treatment may be effectively combined with various other drugs. Among those are e.g. combinations with conventional tumor therapies, multi-epitope strategies, additional immunotherapy, and treatment approaches targeting angiogenesis or apoptosis (for review see e.g. Andersen et al. 2008: Cancer treatment: the combination of vaccination with other therapies. Cancer Immunology Immunotherapy, 57(11): 1735-1743.) Sequential administration of different agents may inhibit cancer cell growth at different check points, while other agents may e.g. inhibit neoangiogenesis, survival of malignant cells or metastases, potentially converting cancer into a chronic disease.

The present invention is further illustrated by the following examples which are not be construed as limiting the scope of the invention.

EXAMPLES

Example 1: Descriptive Analysis of Genetic Immune Polymorphisms

The individual pattern of single nucleotide polymorphisms (SNP) in the patient genome could be predictive for the response rate of the therapeutic antibody IMAB362. In order to investigate such SNP patterns, all patients were genotyped for a number of SNPs with known or presumed role in immune response and gastric cancer susceptibility.

In detail, the following questions were addressed:
a. The SNP genotypes of every patient with regard to studied polymorphisms.
b. The frequency of SNP genotypes in the patient population.
c. Identification of patients with polymorphisms which may interfere directly with IMAB362 mode of action (Fc receptor and complement system polymorphisms).
d. The accumulation of SNP genotypes per patient described as risk factors for gastric cancer susceptibility, cancer progression, or cancer treatment.
e. Correlation of SNP genotypes with clinical outcome.
f. Correlation of SNP genotypes with Progression-Free Survival (PFS).

All patients of cohort 1, 2, and 3 were analyzed for genetic polymorphisms. Patient blood samples were collected on Day 1 (V2a, pre-infusion).

Whole blood samples (9 ml, EDTA-Monovette) were collected from all patients. EDTA blood was stored in 1 ml aliquots immediately after sample collection at the study center at −20° C. EDTA blood samples were shipped on dry ice (−70° C.) and stored at −20° C. Upon arrival, blood samples were stored immediately at −20° C. until DNA isolation.

SNPs of interest were selected by a literature research focusing on SNPs which are known to affect functioning of the immune system and especially SNPs which have been described to affect the mode of action of therapeutic antibodies as Fc receptor and complement system polymorphisms. SNPs having been described to affect survival of gastric cancer patients, susceptibility to (gastric) cancer or progression of gastric cancer were selected and studied as well.

Genetic polymorphisms were analyzed by SNP Genotyping TaqMan™ assays (46 standard, 5 custom made; Life Technologies) on the Fluidigm Biomark™ real time PCR analysis platform. DNA isolation was done according to standard protocols for the isolation of genomic DNA from whole blood. The Fluidigm Biomark™ real time PCR analysis platform allows to genotype up to 96 patient samples with 96 SNPs in one measurement, as patient samples and specific SNP primers are applied to a lab chip with 96 channels for patient DNA samples and 96 orthogonal channels for the SNP assays. Genomic patient DNA is pre-amplified by Specific Target Amplification (STA). Pre-amplified DNA is subjected to TaqMan™ real time PCR analysis under standard conditions in the Fluidigm Biomark™ real time PCR analysis platform. Allelic determination of the SNPs was done for each patient and each assay using the proprietary Fluidigm software and the statistical analysis software "R". A subset of SNPs was confirmed by classical Sanger sequencing as Fluidigm results were ambiguous.

Genetic polymorphisms of 51 single nucleotide polymorphisms (SNP) were determined for 53 patients. The blood sample from 1 patient did not allow DNA extraction in sufficient quantities to analyze SNPs. 6 SNP genotypes were determined for a subset of 20 patients only. The genotype for MDM2 SNP rs2279744 was not determined in 9 patients due to technical problems. The PTGS2 rs20417 genotyping result for 1 patient was ambiguous and was not further investigated. Determination of the matrix of SNP genotypes for tested patients allows statistical testing of the patient population for frequency shifts of genotypes compared to genotype frequency in Caucasian control populations. SNP genotype frequencies in Caucasian control populations are based on data collected by international SNP genotyping projects (HapMap-CEU, PGA-EUROPEAN-PANEL, CAUC1, pilot_1_CEU_low_coverage_panel, CEU_GENO_PANEL, PDR-90) deposited into the public database dbSNP (National Center for Biotechnology Information, Bethesda (MD, USA). The number of patients per genotype of a given SNP was compared with the number of patients per genotype in Caucasian control populations. The number of patients per genotype for control populations was calculated by multiplying the provided relative SNP genotype frequency in the population with the reported number of studied samples. This allowed a direct Chi square test to identify statistically significant differences between the patient population and the corresponding control population.

Figure 1:
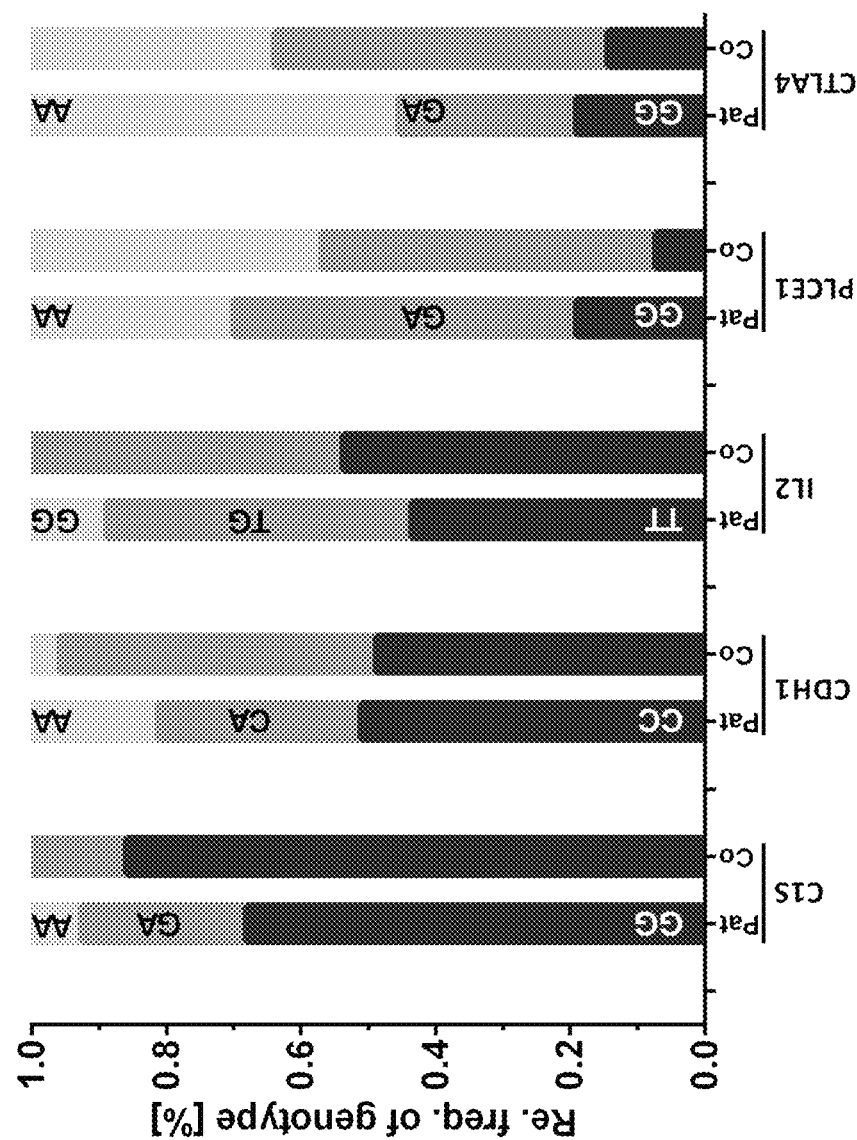
FIG. 1: Single nucleotide polymorphisms with a statistically significant genotype frequency shift between patient and control population ($\chi^2$-test, $p<0.05$).

The Chi square test was performed for 48 out of 51 studied SNPs. No data for SNP genotype frequencies has been deposited in public databases yet for SNPs C1QA (rs1044378), FCGR2C (Q57X (C→T)), and MDM2 (rs2279744). SNPs with a statistically significant shift in genotype frequency between patient and control population (5 of 48 SNPs, p<0.05) are shown in FIG. 1. 4 of these 5 SNPs have been shown to play a role in cancer/gastric cancer susceptibility. All 4 cancer/gastric cancer susceptibility SNPs show indeed an overrepresentation of the respective cancer associated genotype in the patient population, as expected for gastric cancer patients (Table 1).

1 of these 5 SNPs has so far not been shown to be a risk/susceptibility factors in cancer or gastric cancer, rs12146727 (C1S). This SNP has so far only been described as a putative risk factor for cardiovascular disease once.

TABLE 1

Gastric cancer susceptibility-associated SNPs with statistically significant differences in genotype frequency between patient and control population.

| Gene | SNP number | Overrepresented genotype | Major (gastric) cancer susceptibility risk genotype |
|---|---|---|---|
| CDH1 | rs 16260 | AA | AA |
| IL2 | rs2069762 | GG | GG |
| PLCE1 | rs2274223 | GG | GG |
| CTLA4 | rs231775 | GG | GG |

49 out of 51 studied SNPs in the patient population show a variant allele pattern in the studied patient population. This allows testing for frequency shifts of SNP alleles between patient subpopulations, which ideally could help in identification of a putative responder population. Only 2 SNPs, C1QA (rs1044378) and FCGR2C (AHN1ME8) show an invariant SNP genotype in all patients, preventing any kind of differential analysis. For 5 SNPs, a statistically significant allele frequency shift could be determined in this study compared to control populations, providing proof of principle that SNP allele frequency is dependent on the composition of a given population. The tested SNP selection is hence well suited for the future identification of SNP biomarker candidates.

Fc receptor and complement system polymorphisms may interfere directly with IMAB362 mode of action. Patients were genotyped for SNP alleles in genes which may affect the efficacy of antibody-based therapies, as FCGR3A (F176V[T→G], rs396991), FCGR2A (H131R [T→C], rs1801274), and C1QA ([276A→G], rs72378) (Table 2).

Patients were further genotyped for published SNP alleles of the FCGR2C gene (Q57X [C→T], no rs number) and of the complement system factors C1S (R119H [G→A], rs12146727) and C1QA (rs292001, rs1044378). These SNPs have not yet been demonstrated to affect antibody therapy but were included as interesting candidate SNPs.

TABLE 2

Patients with Fc receptor and complement system polymorphisms. The SNP genotypes of patients with well-documented Fc receptor and complement system polymorphisms are listed. FCGR3A Val/Val polymorphisms with a putative positive impact on antibody therapy are depicted bold and underlined. Polymorphisms in FCGR2A (Arg/Arg) and C1QA [G/G] with a putative negative impact on antibody therapy are highlighted in bold.

| Pat. No. | FCGR3A (F176V[T→G]) rs396991 | FCGR2A (H131R[T→C]) rs 1801274 | C1QA ([276A→G]) rs172378 |
|---|---|---|---|
| 100101 | GT | TC | GG |
| 100107 | GT | CC | AA |
| 100124 | GT | CC | GA |
| 100127 | GT | CC | GA |
| 100310 | GT | CC | GA |
| 100411 | GG | TT | GA |
| 100503 | GT | CC | AA |
| 100511 | GT | CC | GG |
| 100605 | GT | CC | AA |
| 100702 | GT | TC | GG |
| 100711 | GT | CC | AA |
| 100715 | GT | CC | AA |
| 100804 | GT | TC | GG |
| 100808 | GT | TT | GG |
| 101117 | GT | TC | GG |
| 101120 | GG | TT | AA |
| 200207 | GT | TT | GG |
| 200310 | GT | CC | GA |
| 200319 | GT | CC | GA |
| 200336 | GG | CC | AA |
| 400101 | GT | TT | GG |
| 400102 | GT | TC | GG |
| 400109 | GG | TT | GG |

A total of 23 patients show at least one of the well-documented Fc receptor and complement system polymorphisms. 4 patients (100411, 101120, 200336, and 400109) were homozygous for the FCGR3A allele (F176V [T→G]), which has been reported to increase response rates and progression free survival in antibody therapy. 12 patients are homozygous for the FCGR2A allele (H131R [T→C]), further 10 patients are homozygous for the C1QA allele ([276A→G]). Both of these SNPs have been demonstrated to impact antibody therapy negatively. In total, 21 patients are homozygous for either the FCGR2A allele (H131R [T→C]) or the C1QA allele ([276A→G](Patient 100511 is homozygous for both SNP alleles).

A correlation of findings above with disease progression of patients may yield insight into the role of Fc receptor and complement system polymorphisms for IMAB362 treatment.

Progression of disease and efficacy of antibody treatment in patients could be affected by the accumulation of SNPs described as risk factors for gastric cancer susceptibility, cancer progression, or cancer treatment. Among the investigated 51 SNPs, up to 43 SNPs allow categorization of the respective SNP genotypes as 'risk' versus 'non-risk' genotypes. The number of homozygous SNP risk factor genotypes per patient was counted as these are described in general as the most relevant risk alleles. The relative frequency of the number of homozygous risk genotypes per patient in relation to the number of investigated SNP risk factors per patient is depicted in FIG. 2.

An accumulation of 14 to 46% of the investigated risk genotypes per patient is observed. This broad distribution allows investigating if the accumulation of SNP risk genotypes per patient correlates with clinical outcome of the patient.

In summary, 53 of 54 patients were successfully genotyped for 51 SNPs. 49 out of 51 SNPs show a variant SNP allele pattern, allowing analysis of patient subpopulations for a significant shift in SNP genotype frequency. Homozygous Fc receptor and complement system polymorphisms described as modulators of antibody therapy are discovered in 23 out of 53 patients. An accumulation of 14 to 46% of the investigated risk genotypes per patient is observed.

Example 2: Correlation of SNP Genotyping with Clinical Results

Objective of the correlation of clinical outcome with genotypes of genetic polymorphisms is the identification of putative SNP biomarker candidates predicting clinical outcome of patients. Putative biomarker candidates identified in this analysis will be verified in subsequent Phase IIb and Phase III studies. Verification of putative biomarker candidates in Phase IIb will allow differentiation between putative prognostic and predictive SNP candidates.

Correlation analysis for each SNP with clinical outcome was done independently for two defined phase IIa clinical trial patient populations: The 'full analysis set' population (FAS) with 40 patients and the 'per protocol set' population with 21 patients.

Absolute frequencies of genotypes of the respective SNP for each clinical outcome group ('responder', 'non-responder') of the patient population were quantified by SAS Enterprise Guide 6.1. Absolute genotype frequencies were organized in contingency tables (3×2 or 2×2) structured by clinical outcome and SNP genotype. The standard statistical test employed was Pearson's Chi square test. Fisher's exact test was applied in some cases for 2×2 contingency tables if numerical structure of the data set prohibited use of Pearson's Chi square test. The level of statistical significance applied was $p<0.05$. Correlation analysis was realized with the statistical analysis software SAS Enterprise Guide 6.1.

In order to investigate the effect of SNP genotypes on progression-free survival, Kaplan-Meier curves were calculated for each group and then formally compared employing the statistical Logrank test. The level of statistical significance applied was $p<0.05$. Logrank statistics were realized with the statistical analysis software SAS Enterprise Guide 6.1.

Correlation of clinical outcome with SNP genotyping is performed to identify putative predictive or prognostic SNP biomarker candidates. Correlation was studied in two patient populations, the FAS population and the PP population.

The FAS population comprises 40 patients, 12 patients defined as 'responder' (clinical outcome 'partial remission' or 'stable disease') and 28 patients as 'non-responder' (clinical outcome 'progression of disease'). One patient sample (100801, non-responder) of the FAS population was not available for SNP analysis as described above, maximum number of FAS patients analyzed for correlations was therefore reduced to 39. The PP population comprises 21 patients with 10 responder patients and 11 non-responder patients.

The number of patients investigated per SNP differ between 20 and 39 (in FAS population) and 20 to 21 (in PP population).

Correlation analysis was done as described above. In total, out of the 51 SNPs studied, 2 show a statistically significant correlation with clinical outcome in FAS as well as in the PP population.

The 2 SNPs showing statistical correlation between clinical outcome and respective SNP genotype in both populations are FCGR2A rs1801274 (p=0.0004 [PP]; p=0.008 [FAS]), and IL-10 rs1800896 (p=0.042 [PP], p=0.022 [FAS]) (Table 3). Number of patients tested statistically per SNP were 21 (PP) and 39 (FAS) for each of these 2 SNPs.

TABLE 3

SNPs showing statistical correlation between clinical outcome and SNP genotype in PP as well as in FAS population.

| rs number | Gene name | Genotype overrepresented in responder population | p-value (PP) | p-value (FAS) |
|---|---|---|---|---|
| rs1801274 | FCGR2A | [CT] | 0.0004 | 0.008 |
| rs1800896 | IL10 | [GG] | 0.042 | 0.022 |

(Chi square test, statistically significant: p < 0.05)

5 SNPs show a correlation with clinical outcome in one patient population (FAS or PP), as can be shown for DNMT3A rs1550117 [PP, p=0.035], SMAD4 rs12456284 [FAS, p=0.02], MUC1 rs4072037 (FAS, p=0.03), EGF rs4444903 [FAS, p=0.049], and CDH1 rs16260 [FAS p=0.049]) (Table 4).

TABLE 4

SNPs showing statistical correlation between clinical outcome and NP genotype in PP or FAS population.

| rs number | Gene name | Genotype overrepresented in responder population | p-value (PP) | p-value (FAS) |
|---|---|---|---|---|
| rs1550117 | DNMT3A | [GA] | 0.035 | 0.32 |
| rs12456284 | SMAD4 | [GA] | 0.081 | 0.023 |
| rs4072037 | MUC1 | [AA] | 0.11 | 0.03 |
| rs4444903 | EGF | [AA] | 0.32 | 0.049 |
| rs16260 | CDH1 | [AA] | 0.72 | 0.049 |

(Chi square test, statistically significant: p < 0.05)

Inspection of over- or underrepresentation of SNP genotypes in responder/non-responder patients may allow to provide scientific explanation for statistically significant frequency differences.

Genotypes of two SNPs, rs11615 (ERCC1) and rs396991 (FCGR3A), are correlated with prolonged progression-free survival (PFS) in the PP population (Table 5).

TABLE 5

SNPs showing statistical correlation between prolonged PFS and SNP genotype in the PP population.

| rs number | Gene name | Genotype correlated with PFS | p-value (PP) | p-value (FAS) |
|---|---|---|---|---|
| rs11615 | ERCC1 | [TT] | 0.0001 | 0.13 |
| rs396991 | FCGR3A | [TG]/[TT] | 0.0007 | 0.25 |

Number of patients tested statistically per SNP were 21 (PP) and 39 (FAS) for each of the 9 SNPs listed.

FCGR2A rs1801274 [C/T]: In PP, all patients harboring the heterozygous rs1801274 [CT] genotype are indeed responder (8) which is reflected in the highly significant p-value (0.0004) of the statistical test. All PR patients (4 out of 4) display this genotype. Most non-responders (73%, 8 out of 11) show the homozygous [TT] genotype (Table 6). This genotype distribution pattern can be found in the FAS population as well, although not as distinct as in the PP population (Table 7). A number of non-responder patients in the FAS population do also harbor the [CT] genotype (30%) which leads to a less pronounced but still statistically highly significant p-value.

TABLE 6

Listing of rs1801274 (FCGR2A) genotypes in PP patients and respective frequencies in responder (PR and SD) and non-responder patients (PD).

| Patient ID | rs1801274 (FCGR2A) genotype | OUTCOME | Best response | PFS [days] | Abs freq. [CT] | Rel freq. [CT] |
|---|---|---|---|---|---|---|
| 100702 | CT | RESP | PR | 322 | 8 | 80% |
| 200316 | CT | RESP | PR | 302 | | |
| 100603 | CT | RESP | PR | 287 | | |
| 200315 | CT | RESP | PR | 238 | | |
| 100108 | CT | RESP | SD | 330 | | |
| 100124 | CC | RESP | SD | 170 | | |
| 100709 | CT | RESP | SD | 146 | | |
| 101302 | CT | RESP | SD | 141 | | |
| 101109 | TT | RESP | SD | 132 | | |
| 100534 | CT | RESP | SD | 78 | | |
| 101116 | TT | NONRESP | PD | 114 | 0 | 0% |
| 100510 | TT | NONRESP | PD | 112 | | |
| 200310 | CC | NONRESP | PD | 102 | | |
| 200319 | CC | NONRESP | PD | 73 | | |
| 101105 | TT | NONRESP | PD | 71 | | |
| 100411 | TT | NONRESP | PD | 70 | | |
| 100513 | TT | NONRESP | PD | 70 | | |
| 100605 | CC | NONRESP | PD | 70 | | |
| 400109 | TT | NONRESP | PD | 67 | | |
| 400101 | TT | NONRESP | PD | 65 | | |
| 101120 | TT | NONRESP | PD | 64 | | |

RESP: Responder, NONRESP: Non-responder, PFS: Progression-free survival, abs freq.: absolute frequency, rel freq.: relative frequency

TABLE 7

Listing of rs1801274 (FCGR2A) genotypes in FAS patients and respective frequencies in responder (PR and SD) and non-responder patients (PD).

| Patient ID | rs1801274 (FCGR2A) genotype | OUTCOME | Best response | PFS [days] | Abs freq. [CT] | Rel freq. [CT] |
|---|---|---|---|---|---|---|
| 100702 | CT | RESP | PR | 322 | 10 | 83% |
| 200316 | CT | RESP | PR | 302 | | |
| 100603 | CT | RESP | PR | 287 | | |
| 200315 | CT | RESP | PR | 238 | | |
| 200205 | CT | RESP | SD | 476 | | |
| 100108 | CT | RESP | SD | 330 | | |
| 400112 | CT | RESP | SD | 194 | | |
| 100124 | CC | RESP | SD | 170 | | |
| 100709 | CT | RESP | SD | 146 | | |
| 101302 | CT | RESP | SD | 141 | | |
| 101109 | TT | RESP | SD | 132 | | |
| 100534 | CT | RESP | SD | 78 | | |
| 100715 | CC | NONRESP | PD | 141 | 8 | 30% |
| 100804 | CT | NONRESP | PD | 119 | | |
| 101116 | TT | NONRESP | PD | 114 | | |
| 100510 | TT | NONRESP | PD | 112 | | |
| 100808 | TT | NONRESP | PD | 112 | | |
| 200310 | CC | NONRESP | PD | 102 | | |
| 200336 | CC | NONRESP | PD | 90 | | |
| 101201 | CT | NONRESP | PD | 79 | | |
| 200207 | TT | NONRESP | PD | 75 | | |
| 200319 | CC | NONRESP | PD | 73 | | |
| 101105 | TT | NONRESP | PD | 71 | | |
| 100411 | TT | NONRESP | PD | 70 | | |
| 100513 | TT | NONRESP | PD | 70 | | |
| 100605 | CC | NONRESP | PD | 70 | | |
| 400109 | TT | NONRESP | PD | 67 | | |
| 400101 | TT | NONRESP | PD | 65 | | |
| 101120 | TT | NONRESP | PD | 64 | | |
| 400111 | CT | NONRESP | PD | 60 | | |
| 100901 | CT | NONRESP | PD | 55 | | |

TABLE 7-continued

Listing of rs1801274 (FCGR2A) genotypes in FAS patients and respective frequencies in responder (PR and SD) and non-responder patients (PD).

| Patient ID | rs1801274 (FCGR2A) genotype | OUTCOME | Best response | PFS [days] | Abs freq. [CT] | Rel freq. [CT] |
|---|---|---|---|---|---|---|
| 100529 | TT | NONRESP | PD | 50 | | |
| 100127 | CC | NONRESP | PD | 47 | | |
| 100410 | CT | NONRESP | PD | 46 | | |
| 100518 | CT | NONRESP | PD | 35 | | |
| 100310 | CC | NONRESP | PD | 30 | | |
| 100607 | CT | NONRESP | PD | 27 | | |
| 100711 | CC | NONRESP | PD | 22 | | |
| 101007 | CT | NONRESP | PD | 17 | | |

RESP: Responder, NONRESP: Non-responder, PFS: Progression-free survival, abs freq.: absolute frequency, rel freq.: relative frequency Survival analysis FCGR2A rs1801274 [C/T]: Highly significant overrepresentation of rs1801274 genotype [CT] in the responder population is expected to be reflected in a correlation with prolonged progression-free survival (PFS) time, too. Indeed, in both populations, PP (FIG. 3) and FAS (FIG. 4), the [CT] genotype is correlated with prolonged PFS (PP p=0.0007, FAS p=0.03) highly significant as well. It is of interest though, that during the first 60 treatment days FAS patients with the [TT] genotype show a trend to a higher PFS rate than the patients with [CC] or [CT] genotype. Survival analysis thus confirms rs1801274 (FCGR2A) as a highly interesting putative biomarker candidate of predictive or prognostic nature.

IL-10 rs1800896 [A/G]: In PP, none of the non-responder patients harbors the homozygous rs1800896 [GG] genotype (Table 8). This genotype is found at elevated frequency (40%) in responder patients (4 out of 10). Only 1 out of 10 responder (10%) shows the [AA] genotype, the remaining responders show the heterozygous [GA] genotype. In FAS, a comparable genotype frequency distribution can be observed (Table 9), although the [GG] genotype can be observed in the non-responder patients in this population at a low frequency (11%, 3 out of 27).

TABLE 8

Listing of rs1800896 (IL-10) genotypes in PP patients and respective frequencies in responder (PR and SD) and non-responder patients (PD).

| Patient ID | rs1800896 (IL-10) genotype | OUTCOME | Best response | PFS [days] | Abs freq. [GG] | Rel freq. [GG] |
|---|---|---|---|---|---|---|
| 100702 | AA | RESP | PR | 322 | 4 | 40% |
| 200316 | GG | RESP | PR | 302 | | |
| 100603 | GA | RESP | PR | 287 | | |
| 200315 | GA | RESP | PR | 238 | | |
| 100108 | GG | RESP | SD | 330 | | |
| 100124 | GA | RESP | SD | 170 | | |
| 100709 | GA | RESP | SD | 146 | | |
| 101302 | GA | RESP | SD | 141 | | |
| 101109 | GG | RESP | SD | 132 | | |
| 100534 | GG | RESP | SD | 78 | | |
| 101116 | AA | NONRESP | PD | 114 | 0 | 0% |
| 100510 | AA | NONRESP | PD | 112 | | |
| 200310 | GA | NONRESP | PD | 102 | | |
| 200319 | GA | NONRESP | PD | 73 | | |
| 101105 | GA | NONRESP | PD | 71 | | |
| 100411 | AA | NONRESP | PD | 70 | | |
| 100513 | AA | NONRESP | PD | 70 | | |
| 100605 | GA | NONRESP | PD | 70 | | |
| 400109 | GA | NONRESP | PD | 67 | | |
| 400101 | AA | NONRESP | PD | 65 | | |
| 101120 | GA | NONRESP | PD | 64 | | |

RESP: Responder, NONRESP: Non-responder, PFS: Progression-free survival, abs freq.: absolute frequency, rel freq.: relative frequency

TABLE 9

Listing of rs1800896 (IL-10) genotypes in FAS patients and respective frequencies in responder (PR and SD) and non-responder patients (PD).

| Patient ID | rs1800896 (IL-10) genotype | OUTCOME | Best response | PFS [days] | Abs freq. [GG] | Rel freq. [GG] |
|---|---|---|---|---|---|---|
| 100702 | AA | RESP | PR | 322 | 6 | 50% |
| 200316 | GG | RESP | PR | 302 | | |
| 100603 | GA | RESP | PR | 287 | | |
| 200315 | GA | RESP | PR | 238 | | |
| 200205 | GG | RESP | SD | 476 | | |
| 100108 | GG | RESP | SD | 330 | | |
| 400112 | GG | RESP | SD | 194 | | |
| 100124 | GA | RESP | SD | 170 | | |
| 100709 | GA | RESP | SD | 146 | | |
| 101302 | GA | RESP | SD | 141 | | |
| 101109 | GG | RESP | SD | 132 | | |
| 100534 | GG | RESP | SD | 78 | | |
| 100715 | GA | NONRESP | PD | 141 | 3 | 11% |
| 100804 | AA | NONRESP | PD | 119 | | |
| 101116 | AA | NONRESP | PD | 114 | | |
| 100510 | AA | NONRESP | PD | 112 | | |
| 100808 | GG | NONRESP | PD | 112 | | |
| 200310 | GA | NONRESP | PD | 102 | | |
| 200336 | AA | NONRESP | PD | 90 | | |
| 101201 | GA | NONRESP | PD | 79 | | |
| 200207 | GA | NONRESP | PD | 75 | | |
| 200319 | GA | NONRESP | PD | 73 | | |
| 101105 | GA | NONRESP | PD | 71 | | |
| 100411 | AA | NONRESP | PD | 70 | | |
| 100513 | AA | NONRESP | PD | 70 | | |
| 100605 | GA | NONRESP | PD | 70 | | |
| 400109 | GA | NONRESP | PD | 67 | | |
| 400101 | AA | NONRESP | PD | 65 | | |
| 101120 | GA | NONRESP | PD | 64 | | |
| 400111 | GA | NONRESP | PD | 60 | | |
| 100901 | GG | NONRESP | PD | 55 | | |
| 100529 | GA | NONRESP | PD | 50 | | |
| 100127 | AA | NONRESP | PD | 47 | | |
| 100410 | GG | NONRESP | PD | 46 | | |
| 100518 | GA | NONRESP | PD | 35 | | |
| 100310 | GA | NONRESP | PD | 30 | | |
| 100607 | GA | NONRESP | PD | 27 | | |
| 100711 | GA | NONRESP | PD | 22 | | |
| 101007 | GA | NONRESP | PD | 17 | | |

RESP: Responder, NONRESP: Non-responder, PFS: Progression-free survival, abs freq.: absolute frequency, rel freq.: relative frequency Survival analysis rs1800896 (IL-10) [A/G]: The rs1800896 [GG] genotype is significantly overrepresented in responder patients. Statistical correlation of the [IGG] genotype with PFS shows that in PP and FAS population, the [IGG] genotype is not significantly correlated with PFS (PP p=0.27 (FIG. 5); FAS p=0.08, (FIG. 6)). However, the p-value for the FAS survival correlation borders on significance, which may be an indication that in larger populations with reduced statistical noise significance may well be reached. Overall, rs1800896 (IL-10) is an interesting putative biomarker candidate.

DNMT3A rs1550117 [G/A]: In PP, 4 responder (40%) show the [GA] genotype whereas all of the non-responder show the [GG] genotype (p=0.03, Table 10).

TABLE 10

Listing of rs1550117 (DNMT3A) genotypes in PP patients and respective frequencies in responder (PR and SD) and non-responder patients (PD).

| Patient ID | rs1550117 (DNMT3A) | OUTCOME | Best response | PFS [days] | Abs freq. [GA] | Rel freq. [GA] |
|---|---|---|---|---|---|---|
| 1007-02 | GG | RESP | PR | 322 | 4 | 40% |
| 2003-16 | GG | RESP | PR | 302 | | |
| 1006-03 | GA | RESP | PR | 287 | | |
| 2003-15 | GA | RESP | PR | 238 | | |
| 1001-08 | GG | RESP | SD | 330 | | |
| 1001-24 | GG | RESP | SD | 170 | | |
| 1007-09 | GA | RESP | SD | 146 | | |
| 1013-02 | GA | RESP | SD | 141 | | |
| 1011-09 | GG | RESP | SD | 132 | | |
| 1005-34 | GG | RESP | SD | 78 | | |
| 1011-16 | GG | NONRESP | PD | 114 | 0 | 0% |
| 1005-10 | GG | NONRESP | PD | 112 | | |
| 2003-10 | GG | NONRESP | PD | 102 | | |

TABLE 10-continued

Listing of rs1550117 (DNMT3A) genotypes in PP patients and respective frequencies in responder (PR and SD) and non-responder patients (PD).

| Patient ID | rs1550117 (DNMT3A) | OUTCOME | Best response | PFS [days] | Abs freq. [GA] | Rel freq. [GA] |
|---|---|---|---|---|---|---|
| 2003-19 | GG | NONRESP | PD | 73 | | |
| 1011-05 | GG | NONRESP | PD | 71 | | |
| 1004-11 | GG | NONRESP | PD | 70 | | |
| 1005-13 | GG | NONRESP | PD | 70 | | |
| 1006-05 | GG | NONRESP | PD | 70 | | |
| 4001-09 | GG | NONRESP | PD | 67 | | |
| 4001-01 | GG | NONRESP | PD | 65 | | |
| 1011-20 | GG | NONRESP | PD | 64 | | |

RESP: Responder, NONRESP: Non-responder, PFS: Progression-free survival, abs freq.: absolute frequency, rel freq.: relative frequency Survival analysis rs1550117 (DNMT3A) [G/A]: The rs1550117 [GA] genotype is significantly overrepresented in responder patients of the PP population. In the FAS population, the difference in PFS between [GA] and [GG] carriers is of borderline significance (FAS p=0.058) (FIG. 7). In the FAS population, only one patient is a carrier of the [AA] genotype.

SMAD4 rs12456284 [G/A]: In FAS, a statistically significant overrepresentation of the [GA] genotype (7 of 12 patients, 58%) over the [AA] and [GG] genotype can be found in the responder population (p=0.023, Table 11). In the FAS non-responder population the frequency of the [GA] genotype can be found at a frequency of 19% (5 of 27 non-responder). In the PP population this association is indicated by trend significance (p=0.081, data not shown).

TABLE 11

Listing of rs12456284 (SMAD4) genotypes in FAS patients and respective frequencies in responder (PR and SD) and non-responder patients (PD).

| Patient ID | rs12456284 (SMAD4) genotype | OUTCOME | Best response | PFS [days] | Abs freq. [GA] | Rel freq. [GA] |
|---|---|---|---|---|---|---|
| 1007-02 | AA | RESP | PR | 322 | 7 | 58% |
| 2003-16 | GA | RESP | PR | 302 | | |
| 1006-03 | GA | RESP | PR | 287 | | |
| 2003-15 | GA | RESP | PR | 238 | | |
| 2002-05 | GA | RESP | SD | 476 | | |
| 1001-08 | AA | RESP | SD | 330 | | |
| 4001-12 | AA | RESP | SD | 194 | | |
| 1001-24 | GA | RESP | SD | 170 | | |
| 1007-09 | GA | RESP | SD | 146 | | |
| 1013-02 | AA | RESP | SD | 141 | | |
| 1011-09 | AA | RESP | SD | 132 | | |
| 1005-34 | GA | RESP | SD | 78 | | |
| 1007-15 | GG | NONRESP | PD | 141 | 5 | 19% |
| 1008-04 | AA | NONRESP | PD | 119 | | |
| 1011-16 | GA | NONRESP | PD | 114 | | |
| 1005-10 | AA | NONRESP | PD | 112 | | |
| 1008-08 | AA | NONRESP | PD | 112 | | |
| 2003-10 | GA | NONRESP | PD | 102 | | |
| 2003-36 | AA | NONRESP | PD | 90 | | |
| 1012-01 | AA | NONRESP | PD | 79 | | |
| 2002-07 | AA | NONRESP | PD | 75 | | |
| 2003-19 | AA | NONRESP | PD | 73 | | |
| 1011-05 | AA | NONRESP | PD | 71 | | |
| 1004-11 | AA | NONRESP | PD | 70 | | |
| 1005-13 | AA | NONRESP | PD | 70 | | |
| 1006-05 | AA | NONRESP | PD | 70 | | |
| 4001-09 | AA | NONRESP | PD | 67 | | |
| 4001-01 | AA | NONRESP | PD | 65 | | |
| 1011-20 | AA | NONRESP | PD | 64 | | |
| 4001-11 | AA | NONRESP | PD | 60 | | |
| 1009-01 | GA | NONRESP | PD | 55 | | |
| 1005-29 | AA | NONRESP | PD | 50 | | |
| 1001-27 | AA | NONRESP | PD | 47 | | |
| 1004-10 | AA | NONRESP | PD | 46 | | |
| 1005-18 | AA | NONRESP | PD | 35 | | |
| 1003-10 | AA | NONRESP | PD | 30 | | |
| 1006-07 | AA | NONRESP | PD | 27 | | |
| 1007-11 | GA | NONRESP | PD | 22 | | |
| 1010-07 | GA | NONRESP | PD | 17 | | |

RESP: Responder, NONRESP: Non-responder, PFS: Progression-free survival, abs freq.: absolute frequency, rel freq.: relative frequency Survival analysis rs12456284 (SMAD4) [G/A]: The rs12456284 [GA] genotype is significantly overrepresented in FAS responder patients and shows the same trend in PP responders. Statistical correlation of rs12456284 genotypes with PFS shows that in the PP population, the [GA] genotype is significantly correlated with PFS (PP p=0.048) using the Gehan-Brelow-Wilcoxon test (FIG. 8) whereas significant genotype distribution in responder and non-responder FAS patients is statistically significant (p=0.03). A comparable genotype distribution pattern is found in the PP population (data not shown), where responder show nearly the same relative [AA] genotype frequency of 70% (7 out of 10) as in the FAS population (trend significance p=0.11).

TABLE 12

Listing of rs4072037 (MUC1) genotypes in FAS patients and respective frequencies in responder (PR and SD) and non-responder patients (PD).

| Patient ID | rs4072037 (MUC1) genotype | OUTCOME | Best response | PFS [days] | Abs freq. [AA] | Rel freq. [AA] |
|---|---|---|---|---|---|---|
| 100702 | AA | RESP | PR | 322 | 8 | 67% |
| 200316 | AA | RESP | PR | 302 | | |
| 100603 | AA | RESP | PR | 287 | | |
| 200315 | AG | RESP | PR | 238 | | |
| 200205 | AA | RESP | SD | 476 | | |
| 100108 | AA | RESP | SD | 330 | | |
| 400112 | AG | RESP | SD | 194 | | |
| 100124 | AA | RESP | SD | 170 | | |
| 100709 | AG | RESP | SD | 146 | | |
| 101302 | AA | RESP | SD | 141 | | |
| 101109 | AG | RESP | SD | 132 | | |
| 100534 | AA | RESP | SD | 78 | | |
| 100715 | AG | NONRESP | PD | 141 | 7 | 26% |
| 100804 | AG | NONRESP | PD | 119 | | |
| 101116 | AA | NONRESP | PD | 114 | | |
| 100510 | AA | NONRESP | PD | 112 | | |
| 100808 | AG | NONRESP | PD | 112 | | |
| 200310 | AG | NONRESP | PD | 102 | | |
| 200336 | GG | NONRESP | PD | 90 | | |
| 101201 | AG | NONRESP | PD | 79 | | |
| 200207 | AG | NONRESP | PD | 75 | | |
| 200319 | AA | NONRESP | PD | 73 | | |
| 101105 | GG | NONRESP | PD | 71 | | |
| 100411 | AA | NONRESP | PD | 70 | | |
| 100513 | GG | NONRESP | PD | 70 | | |
| 100605 | AG | NONRESP | PD | 70 | | |
| 400109 | GG | NONRESP | PD | 67 | | |
| 400101 | GG | NONRESP | PD | 65 | | |
| 101120 | AG | NONRESP | PD | 64 | | |
| 400111 | GG | NONRESP | PD | 60 | | |
| 100901 | AG | NONRESP | PD | 55 | | |
| 100529 | AA | NONRESP | PD | 50 | | |
| 100127 | AG | NONRESP | PD | 47 | | |
| 100410 | AG | NONRESP | PD | 46 | | |
| 100518 | AA | NONRESP | PD | 35 | | |
| 100310 | AG | NONRESP | PD | 30 | | |
| 100607 | AG | NONRESP | PD | 27 | | |
| 100711 | AG | NONRESP | PD | 22 | | |
| 101007 | AA | NONRESP | PD | 17 | | |

RESP: Responder, NONRESP: Non-responder, PFS: Progression-free survival, abs freq.: absolute frequency, rel freq.: relative frequency cance using the logrank test is p=0.35. The Gehan-Brelow-Wilcoxon test gives more weight to PFS events at early time points than the logrank test and indeed the difference between [GA] and [AA] carriers is most pronounced during the respective first 100 days of this phase IIa clinical trial. In the FAS population the [GA] genotype is not significantly correlated with PFS (p=0.20 (logrank), p=0.23 (Gehan-Brelow-Wilcoxon)), although visual inspection suggests a trend of [GA] carriers to prolonged PFS.

MUC1 rs4072037 [A/G]: In FAS, the rs4072037 genotype found with highest frequency of 67% in the responder population is [AA] (8 out of 12), whereas non-responders display this genotype in only 26% of patients (7 out of 27). None of the responder patients shows the homozygous [GG] genotype (Table 12) whereas non-responder show the [GG] genotype at a rate of 22% (6 out of 27). This differential Survival analysis rs4072037 (MUC1) [A/G]: The significant overrepresentation of rs4072037 genotype [AA] in responder patients may indicate correlation of this genotype with PFS. Statistical testing reveals that in PP and FAS population, the [AA] genotype is significantly correlated with PFS (PP p=0.001, (FIG. 9); FAS p=0.02, (FIG. 10)). This survival analysis confirms rs4072037 (MUC1) as a very interesting putative predictive or prognostic biomarker candidate.

EGF rs4444903 [G/A]: In FAS, the rs4444903 genotype [AA] is significantly overrepresented (p=0.049) in the responder population (5 out of 12; 42%) compared to the non-responder population (3 out of 27; 11%) (Table 13). In the PP population this asymmetrical distribution is not statistically significant (p=0.32, data not shown).

TABLE 13

Listing of rs4444903 (EGF) genotypes in FAS patients and respective frequencies in responder (PR and SD) and non-responder patients (PD).

| Patient ID | rs4444903 (EGF) genotype | OUTCOME | Best response | PFS [days] | Abs freq. [AA] | Rel freq. [AA] |
|---|---|---|---|---|---|---|
| 1007-02 | GA | RESP | PR | 322 | 5 | 42% |
| 2003-16 | AA | RESP | PR | 302 | | |
| 1006-03 | AA | RESP | PR | 287 | | |
| 2003-15 | AA | RESP | PR | 238 | | |
| 2002-05 | GA | RESP | SD | 476 | | |
| 1001-08 | GA | RESP | SD | 330 | | |
| 4001-12 | GA | RESP | SD | 194 | | |
| 1001-24 | AA | RESP | SD | 170 | | |
| 1007-09 | AA | RESP | SD | 146 | | |
| 1013-02 | GG | RESP | SD | 141 | | |
| 1011-09 | GA | RESP | SD | 132 | | |
| 1005-34 | GA | RESP | SD | 78 | | |
| 1007-15 | GG | NONRESP | PD | 141 | 3 | 11% |
| 1008-04 | GA | NONRESP | PD | 119 | | |
| 1011-16 | AA | NONRESP | PD | 114 | | |
| 1005-10 | GA | NONRESP | PD | 112 | | |
| 1008-08 | GA | NONRESP | PD | 112 | | |
| 2003-10 | GA | NONRESP | PD | 102 | | |
| 2003-36 | GG | NONRESP | PD | 90 | | |
| 1012-01 | GG | NONRESP | PD | 79 | | |
| 2002-07 | GA | NONRESP | PD | 75 | | |
| 2003-19 | GG | NONRESP | PD | 73 | | |
| 101105 | AA | NONRESP | PD | 71 | | |
| 1004-11 | GA | NONRESP | PD | 70 | | |
| 1005-13 | GA | NONRESP | PD | 70 | | |
| 1006-05 | GA | NONRESP | PD | 70 | | |
| 4001-09 | GG | NONRESP | PD | 67 | | |
| 4001-01 | GG | NONRESP | PD | 65 | | |
| 1011-20 | GA | NONRESP | PD | 64 | | |
| 4001-11 | GA | NONRESP | PD | 60 | | |
| 1009-01 | GA | NONRESP | PD | 55 | | |
| 1005-29 | GG | NONRESP | PD | 50 | | |
| 1001-27 | GG | NONRESP | PD | 47 | | |
| 1004-10 | GG | NONRESP | PD | 46 | | |
| 1005-18 | GG | NONRESP | PD | 35 | | |
| 1003-10 | GA | NONRESP | PD | 30 | | |
| 1006-07 | GA | NONRESP | PD | 27 | | |
| 1007-11 | AA | NONRESP | PD | 22 | | |
| 1010-07 | GA | NONRESP | PD | 17 | | |

RESP: Responder, NONRESP: Non-responder, PFS: Progression-free survival, abs freq.: absolute frequency, rel freq.: relative frequency Survival analysis rs4444903 (EGF) [G/A]: The correlation of the rs4444903 [AA] genotype with PFS in the PP or FAS population is not statistically significant (FAS p=0.1; PP p=0.16). However, a trend towards prolonged PFS can be observed both in PP and FAS population (FIG. 11).

CDH1 rs16260 [C/A]: In FAS, the rs16260 genotype [AA] is found at a significantly higher frequency in the responder (5 out of 12; 42%) than the non-responder population (3 out of 27; 11%) (p=0.049, Table 14). In PP, this asymmetrical distribution between both patient groups is not significant (p=0.72, data not shown).

TABLE 14

Listing of rs16260 (CDH1) genotypes in FAS patients and respective frequencies in responder (PR and SD) and non-responder patients (PD).

| Patient ID | rs16260 (CDH1) genotype | OUTCOME | Best response | PFS [days] | Abs freq. [AA] | Rel freq. [AA] |
|---|---|---|---|---|---|---|
| 1007-02 | AA | RESP | PR | 322 | 5 | 42% |
| 2003-16 | CC | RESP | PR | 302 | | |
| 1006-03 | CC | RESP | PR | 287 | | |
| 2003-15 | AA | RESP | PR | 238 | | |
| 2002-05 | AA | RESP | SD | 476 | | |
| 1001-08 | CA | RESP | SD | 330 | | |
| 4001-12 | AA | RESP | SD | 194 | | |
| 1001-24 | CC | RESP | SD | 170 | | |

TABLE 14-continued

Listing of rs16260 (CDH1) genotypes in FAS patients and respective frequencies in responder (PR and SD) and non-responder patients (PD).

| Patient ID | rs16260 (CDH1) genotype | OUTCOME | Best response | PFS [days] | Abs freq. [AA] | Rel freq. [AA] |
|---|---|---|---|---|---|---|
| 1007-09 | AA | RESP | SD | 146 | | |
| 1013-02 | CC | RESP | SD | 141 | | |
| 1011-09 | CC | RESP | SD | 132 | | |
| 1005-34 | CC | RESP | SD | 78 | | |
| 1007-15 | CC | NONRESP | PD | 141 | 3 | 11% |
| 1008-04 | CC | NONRESP | PD | 119 | | |
| 1011-16 | CA | NONRESP | PD | 114 | | |
| 1005-10 | AA | NONRESP | PD | 112 | | |
| 1008-08 | CC | NONRESP | PD | 112 | | |
| 2003-10 | CC | NONRESP | PD | 102 | | |
| 2003-36 | CA | NONRESP | PD | 90 | | |
| 1012-01 | CA | NONRESP | PD | 79 | | |
| 2002-07 | CO | NONRESP | PD | 75 | | |
| 2003-19 | CC | NONRESP | PD | 73 | | |
| 1011-05 | AA | NONRESP | PD | 71 | | |
| 1004-11 | AA | NONRESP | PD | 70 | | |
| 1005-13 | CC | NONRESP | PD | 70 | | |
| 1006-05 | CC | NONRESP | PD | 70 | | |
| 4001-09 | CA | NONRESP | PD | 67 | | |
| 4001-01 | CA | NONRESP | PD | 65 | | |
| 1011-20 | CC | NONRESP | PD | 64 | | |
| 4001-11 | CC | NONRESP | PD | 60 | | |
| 1009-01 | CC | NONRESP | PD | 55 | | |
| 1005-29 | CA | NONRESP | PD | 50 | | |
| 1001-27 | CA | NONRESP | PD | 47 | | |
| 1004-10 | CA | NONRESP | PD | 46 | | |
| 1005-18 | CA | NONRESP | PD | 35 | | |
| 1003-10 | CC | NONRESP | PD | 30 | | |
| 1006-07 | CA | NONRESP | PD | 27 | | |
| 1007-11 | CC | NONRESP | PD | 22 | | |
| 1010-07 | CC | NONRESP | PD | 17 | | |

RESP: Responder, NONRESP: Non-responder, PFS: Progression-free survival, abs freq.: absolute frequency, rel freq.: relative frequency Survival analysis rs16260 (CDH1) [C/A]: The rs16260 (CDH1) genotype [AA] correlation with PFS borders on statistical significance in the FAS population (Logrank test p=0.065, Gehan-Brelow-Wilcoxon test p=0.032) (FIG. 12).

ERCC1 rs11615 [C/T]: In PP, a trend for higher frequency of the rs11615 genotype [TT] in the responder population (3 out of 10; 30%) is found (p=0.068; non-responder population (0%)). Inversely, the homozygous [CC] genotype is only found in the non-responder population (2 patients) (Table 15).

TABLE 15

Listing of rs11615 (ERCC1) genotypes in PP patients and respective frequencies in responder (PR and SD) and non-responder patients (PD).

| Patient ID | rs11615 (ERCC1) | OUTCOME | Best response | PFS [days] | Abs freq. [TT] | Rel freq. [TT] |
|---|---|---|---|---|---|---|
| 1007-02 | CT | RESP | PR | 322 | 3 | 30% |
| 2003-16 | CT | RESP | PR | 302 | | |
| 1006-03 | CT | RESP | PR | 287 | | |
| 2003-15 | TT | RESP | PR | 238 | | |
| 1001-08 | CT | RESP | SD | 330 | | |
| 1001-24 | TT | RESP | SD | 170 | | |
| 1007-09 | CT | RESP | SD | 146 | | |
| 1013-02 | CT | RESP | SD | 141 | | |
| 1011-09 | CT | RESP | SD | 132 | | |
| 1005-34 | TT | RESP | SD | 78 | | |
| 1011-16 | CT | NONRESP | PD | 114 | 0 | 0% |
| 1005-10 | CT | NONRESP | PD | 112 | | |
| 2003-10 | CT | NONRESP | PD | 102 | | |
| 2003-19 | CT | NONRESP | PD | 73 | | |
| 1011-05 | CT | NONRESP | PD | 71 | | |
| 1004-11 | CT | NONRESP | PD | 70 | | |
| 1005-13 | CT | NONRESP | PD | 70 | | |

TABLE 15-continued

Listing of rs11615 (ERCC1) genotypes in PP patients and respective frequencies in responder (PR and SD) and non-responder patients (PD).

| Patient ID | rs11615 (ERCC1) | OUTCOME | Best response | PFS [days] | Abs freq. [TT] | Rel freq. [TT] |
|---|---|---|---|---|---|---|
| 1006-05 | CT | NONRESP | PD | 70 | | |
| 4001-09 | CC | NONRESP | PD | 67 | | |
| 4001-01 | CT | NONRESP | PD | 65 | | |
| 1011-20 | CC | NONRESP | PD | 64 | | |

RESP: Responder, NONRESP: Non-responder, PFS: Progression-free survival, abs freq.: absolute frequency, rel freq.: relative frequency Survival analysis rs11615 (ERCC1) [C/T]: The rs11615 [TT] genotype is found exclusively in the responder population in the PP population. Statistical correlation of rs11615 genotypes with PFS shows that the rs11615 genotype in PP is highly significantly correlated with PFS, with [CT] and [TT] carriers showing prolonged survival compared to [CC] carriers (PP p=0.0001) (FIG. 13). Despite this striking significance value, it should be noted that there are only 2 patients with the [CC] genotype and 3 patients with the [TT] genotype in PP. However, in the FAS population the same effect can be observed as a trend (FAS p=0.13. data not shown), suggesting that the effect is also valid in larger patient populations.

Survival analysis FCGR3A rs396991 [T/G]: Neither in PP or FAS, the genotype of SNP rs396991 is correlated with clinical outcome (FAS p=0.49; PP p=0.29, data not shown). However, survival analysis in the PP population indicates with high statistical significance that patients with the genotypes [TG] and [TT] show improved PFS compared to [GG] (p=0.0007, FIG. 14). This effect can also be observed in the FAS population (p=0.25; data not shown). Despite the significance value received for the PP population, it should be noted that only 3 PP patients are [GG] carriers.

Example 3: Discussion of Accompanying Immune Polymorphism Analyses

The primary objective of this clinical phase IIa trial was the evaluation of safety and efficacy of the therapeutic anti-CLDN18.2 mononuclear antibody IMAB362 in patients with gastroesophageal adenocarcinomas. In addition, accompanying analyses on genetic immune response polymorphisms were performed to evaluate parameters that may serve as potential predictive or prognostic biomarkers in correlation with IMAB362 therapy.

Discussion of Descriptive Immune Polymorphism Analysis

Genetic polymorphisms in the patient's genome have been shown to alter the response rate of therapeutic antibodies. In order to investigate the impact of individual genetic variation on the response rate, the genotypes of 51 single nucleotide polymorphisms (SNPs) with known or presumed role in immune response and gastric cancer susceptibility or progress were determined in patients.

In this study, 51 SNPs were successfully genotyped for 53 out of 54 patients studied. A statistically significant shift of genotype frequency in the patient population compared to control populations could be detected for 5 SNPs. 4 of these SNPs have been shown before to be associated with cancer/ gastric cancer susceptibility. The respective cancer/gastric cancer associated genotypes of these 4 SNPs are over-represented in the study population, as expected in a patient population with advanced GC. Over-representation of the respective homozygous genotype may indicate a recessive mode of action implicating a compromised gene function as opposed to enhanced gene activity. This is underscored by published data, e.g. the gastric cancer associated AA genotype of SNP rs16260 in CDH1 has been reported to cause a down-regulation of CDH1 expression due to its position in the promoter of CDH1 at −160.

Polymorphisms in genes being involved in immune signaling were investigated even if these polymorphisms had not been described before as gastric cancer risk factors. Genetic polymorphisms in genes coding for immune signaling factors have been shown to modulate the risk of developing gastric cancer significantly. Response rate of an antibody-based cancer therapy might therefore be affected by these SNPs as well.

The over-represented IL-2 genotype GG (SNP rs2069762) in the patient population is associated with an increased risk of gastric atrophy induced by *H. pylori* infection and may predispose to gastric cancer. CTLA4 SNP rs231775 and rs2274223 (PLCE1) genotypes have been described as GC susceptibility risk factors. As published studies on rs231775 are contradictory on the sequence of the genotype, however, no conclusion will be drawn here.

Fc-receptor and complement system polymorphisms were investigated in this study. The possibly beneficial FCGR3A genotype coding for Val/Val [GG] is detected in 4 APT patients, the FCGR2A genotype with a potentially negative impact (Arg/Arg) [CC] can be detected in 12 APT patients. CDC as a second effector mechanism has been demonstrated to be affected by SNP polymorphisms as well: A allele carriers of a polymorphism in the complement component C1qA ([276A→G], rs172378) show prolonged response following Rituximab therapy of follicular lymphoma. The complement system polymorphism in C1QA with genotype 'GG' is detected in 10 patients, possibly affecting response negatively. The SNP polymorphism rs12146727 in complement component C1S, however, has so far been described only in a screen not related to antibody therapies or cancer.

The identification of significant genotype frequency shifts between patient and control populations demonstrates that SNP genotype frequency shifts may serve as predictive and prognostic markers in clinical studies.

Accumulation of SNP risk alleles may have an impact on a patients' clinical outcome as well. In order to allow such an analysis, the number of homozygous SNP risk genotypes was counted per patient. Correlation of these numbers with therapy response may give insight into the role of SNP risk factor accumulation.

Discussion of Correlation of SNP Genotyping with Clinical Outcome

FCGR2A rs1801274:

Inspection of FCGR2A genotypes over- or underrepresented reveals that in the PP population all patients with the heterozygous rs1801274 genotype [CT] are responder patients and that patients with partial response (PR) exclusively harbor this genotype. The overrepresented homozygous genotype in the non-responder population is [TT]. The mere observation of these frequency distributions does not allow conclusion if the [CT] genotype is beneficial or if the [TT] is disadvantageous. In most studies investigating the impact of SNP genotypes, the respective homozygous genotypes show the strongest biological effects, indicating often a recessive mode of action reflecting compromised gene function of both alleles as opposed to enhanced gene activity. In case SNP alleles lead to increased genetic activity, a stepwise effect of biological effect can often be observed: One allele (i.e. heterozygous) increases gene activity, two alleles (i.e. homozygous) increase gene activity even more. In both cases, gain of function or loss of function, the strongest biological/clinical effects are usually observed in patients with homozygous genotypes. Under this assumption overrepresentation of the homozygous [TT] genotype in the non-responder population in the PP and FAS population would cause a disadvantageous effect. This is unexpected, however, as the rs1801274 FCGR2A [TT] genotype has been described in a number of clinical studies as a factor having a prolonging effect on PFS. In our phase IIa clinical trial, closer inspection of the association between genotype and PFS in FAS non-responder patients indicates that FAS PD patients with the [TT] genotype show during the first 60 days of therapy indeed a trend towards higher PFS times as opposed to FAS PD patients with the [CT] genotype (compare Table 7 and FIG. 4). An interpretation to bring this observation in line with the underrepresentation of [TT] in responders with prolonged PFS could be an overlay of two different molecular mechanisms: First, the rs1801274 [CT] genotype could be a marker for responder patients. This is a new observation not described in the literature so far and may suggest that this genotype is a predictive marker for treatment with IMAB362. The molecular mechanism underlying this new observation has not been resolved yet.

The second observation, already described in the literature for other therapeutic anti-cancer antibodies, would be the prolonged PFS of patients harboring the FCGR2A [TT] genotype. In our phase IIa study this effect is due to overlay of the postulated first mechanism only observable as a trend in non-responder patients. Mechanistically, the second observation could be explained by increased binding affinity of the IgG1 antibody to the FCGR2A 131 His/His receptor allele (encoded by [TT] genotype) as opposed to weaker binding affinity to the homozygous FCGR2A 131 Arg/Arg receptor allele (encoded by [CC] genotype): In studies investigating the impact of Fcγ-receptor polymorphisms systematically, it has recently been shown that antibodies of the IgG1 isotype indeed bind with different affinities to the two allelic forms of the Fcγ receptor IIA, H131 with a higher affinity than R131. Differential affinity of IgG antibodies to the FCGR2A receptor alleles is generally assumed to affect the trigger rate of effector mechanisms and consequently prolonged PFS in patients harboring the high affinity receptor allele. Data supporting this hypothesis has been provided by reports showing that Fc-receptor polymorphisms FCGR2A H131R and FCGR3A F176V (Phe>Val, rs396991) may have an impact on the clinical efficacy of Trastuzumab-based IgG1 antibody therapy in metastatic breast cancer patients. Patients with the genotypes FCGR3A 176 Val/Val and FCGR2A 131 His/His showed significantly better response rate and progression-free survival. The same polymorphisms have also been associated with the response rate of rituximab (IgG1)-treated patients with B-cell lymphomas.

In another study, prolonged PFS after Cetuximab (IgG1) therapy could be associated with the FCGR3A 176 Val/Val genotype.

Controversially, there are recent well-powered studies reporting no association between Fc-receptor polymorphisms and survival, response rate, or progression-free survival for the antibodies discussed. In the BCIRG-006 trial of the Breast Cancer International Research Group (BCIRG) 1218 patients were treated in a randomized study with two Trastuzumab-containing arms and a non-Trastuzumab control arm. The associations reported above between Fcγ-receptor polymorphisms and Trastuzumab efficacy could not be confirmed. A long term study with 460 patients employing rituximab combined with chemotherapy in follicular lymphoma reported no association of Fcγ-receptor polymorphisms with progression-free survival. In the REACH trial with 419 patients, where patients received fludarabine and cyclophosphamide (FC) or rituximab plus FC, FCGR2A and FCGR3A polymorphisms did not significantly influence outcome. Recent Cetuximab trials also yielded inconsistent findings, not recommending Fcγ-receptor polymorphisms as useful biomarkers. This may reflect differences in intrinsic population factors or concurrent chemotherapy regimens.

MUC1 rs4072037:

MUC1 is a transmembrane glycoprotein of the mucin family. Mucins are high-molecular weight proteins which are O-glycosylated in the N-terminal extracellular domain extensively with oligosaccharides and n-glycan chains. Mucins are expressed on the apical surface of epithelia lining respiratory and gastrointestinal tracts and ducts in liver, pancreas, and kidneys. Transmembrane mucins span the membrane with one α-helix and provide with their sugar chains a protective lining to the extracellular space. Mucins secreted into the extracellular space build up a mucous gel layer serving as additional physical protection for the epithelium.

The transmembrane MUC1 and the secreted mucins MUC5C and MUC6 are the main mucins expressed in the stomach. MUC1 is translated as a single polypeptide chain which is subject to autocleavage. The N-terminal extracellular domain (MUC1-N) remains initially non-covalently connected to the transmembrane/intracytoplasmic domain (MUC1-C). This intracytoplasmic domain serves as a signaling domain which can enter the nucleus and associate with a number of transcription factors to activate gene expression directly. Cell stress can lead to proteolytic cleavage of the MUC1-N and MUC1-C domain via a second proteolytic site. This can be observed in cancer cells, too, where MUC1 is no longer expressed in an ordered fashion at the apical membrane of the cell but can be found overexpressed and localized throughout the cell. Shedding of the extracellular domain (also known as CA15-3) into the extracellular space and intracellular localization of MUC1-C is the consequence. The intracytoplasmic signaling domain acts as an oncogene e.g. by activation of Wnt/β-catenin signaling and blocking of apoptotic pathways.

The extracellular domain of MUC1, however, is not only a static structural component but plays important roles during signaling events at the cell membrane. The glycosylation and expression state of the MUC1 extracellular domain has been demonstrated to regulate interactions of membrane signaling molecules and the extracellular matrix. Underglycosylated MUC1-N in tumor cells has been reported to increase signaling between membrane molecules as ICAM-1 or E-selectin and the MUC1 coreprotein. Furthermore, mucin expression and glycosylation state seems to mask membrane-associated molecules. In cancer cells, masking of HER2 proteins by mucin expression has been described as a possible resistance mechanism to Trastuzumab therapy.

The MUC1 polymorphism rs4072037 'A' allele has been described as a risk factor for gastric cancer susceptibility. This polymorphism is a G→A exchange in Exon 2, resulting in alternative splicing of MUC1 exactly in the predicted signal peptide cleavage site of MUC1. Deficient cleavage of the signal peptide could lead to aberrant MUC1 protein localization or glycosylation pattern and consequently deficient protein function.

In this phase IIa clinical trial, the rs4072037 [AA] genotype has been found to be statistically associated with the responder population. It could be speculated that the underglycosylated or underexpressed [AA] allelic form of MUC1 allows better access of IMAB362 to the membrane target molecule CLDN18.2 expressed on cancer cells, consequently promoting treatment efficacy. This would render rs4072037 a predictive biomarker.

IL-10 rs1800896:

IL-10 is a key regulator of the immune system with pleiotropic functions. IL-10 is known to act as an anti-inflammatory, immunosuppressive cytokine by inhibiting macrophage-dependent antigen-specific T-cell proliferation and macrophage-dependent production of cytokines by T-cells. However, IL-10 has been described also as an immunostimulatory cytokine, enhancing B-cell, granulocyte and mast cell differentiation and growth as well as NK-cell and CD8+ T-cell activation. The pleiotropic potential of IL-10 is also reflected by the widespread expression of IL-10 in many immune cell types including Th2 cells, Treg cells, Th3 cells, NK T cells, B cells, macrophages, and dendritic cells. This dual role of IL-10 is reflected in the tumor-promoting as well as tumor-inhibiting potential: IL-10 secreted by tumor cells or tumor infiltrating immune cells as macrophages allows tumor cells to escape from immune surveillance by mechanisms which have been clarified only in part. One mechanism described involves Treg cells contributing to the induction of peripheral tolerance via expression of immunoregulatory cytokines like IL-10. Another mechanism reported is the inhibition of cross-presentation of tumor-associated antigens by dendritic cells and therefore prevention of T cells from starting an effective immune response against tumor cells. On the other hand, exposition of malignant tumor cells to IL-10 leads to a down regulation of HLA class I proteins resulting in increased sensitivity to NK cell cytotoxicity.

The IL-10 promoter polymorphism rs1800896 at position (−1082) is of interest as the 'G' allele has been reported as gastric cancer risk factor and renal cancer risk factor. The 'G' allele of this polymorphism has been reported to be associated in vitro with decreased IL-10 expression compared to the 'A' allele. In responder patients of this phase IIa clinical trial the [GG] genotype of rs1800896 is over represented, possibly indicating a lower relative expression level of IL-10. It can be speculated that patients harboring the [GG] genotype have a lower IL-10 expression which in turn may render it more difficult for tumor cells to escape from immune surveillance by one of the mechanisms described above. Indeed, none of the 12 FAS responder patients shows elevated IL-10 serum level as opposed to 22% of the FAS non-responder patients (6 out of 27 measured). However, other authors state that the 'A' allele is associated with decreased IL-10 expression.

It should also be noted, that IL-10 signals through the intracellular mediator Stat3 and that Stat3 activation is dependent on MUC1-C. Therefore, the functional interaction of MUC1 and IL-10 could be the reason why these molecules both proved to be statistically significant biomarker candidates in this phase IIa clinical trial. Finally, FCGR2A is expressed on macrophages, which are often a major source of IL-10 in the tumor microenvironment. If these putative biomarker candidates prevail in ongoing and future studies, an investigation of the functional interaction of these factors may be of considerable interest.

rs1550117 (DNMT3A):

rs1550117 is a SNP in the DNMT3A gene coding for the enzyme DNA (cytosine-5)-methyltransferase 3A catalyzing the transfer of methyl groups to specific CpG structures in DNA inducing epigenetic modification. It has been shown that the genotype [AA] confers an increased risk for gastric cancer as compared to [GG] or [GA]. In this study [AA] could be found in only one patient in the FAS population and no patient of the PP population. This may indicate that [AA] also confers a risk for survival, too, preventing third and fourth line treatment of [AA] carriers in this phase IIa clinical trial. The finding that [GA] is significantly correlated with clinical outcome in PP suggests that this marker holds potential as a predictive biomarker for IMAB362 treatment.

rs12456284 (SMAD4):

rs12456284 is a SNP in the SMAD4 gene coding for the intracellular TGFβ/BMP-signaling co-transducer "Mothers against decapentaplegic homolog 4". It has been published that the [GG] genotype significantly decreased the risk for gastric cancer. The statistically significant overrepresentation of the heterozygous [GA] genotype over the [AA] genotype in the FAS responder population suggests that this genotype may serve as predictive biomarker. Prolonged PFS of patients of the PP population carrying [GA] is a supporting fact.

rs4444903 (EGF):

The functional polymorphism rs4444903 in the promoter region of the EGF gene was observed to modulate EGF protein levels, higher amounts of EGF factor were detected in the serum of [GG] carriers. The G allele and [GG] genotype of this polymorphism showed significant correlations with increased risk of gastrointestinal cancer in a meta-analysis.

In this phase IIa clinical trial the genotype [AA] is significantly overrepresented in FAS responders and patients with this genotype show a trend towards prolonged PFS in FAS and PP population. This could indicate that the rs4444903 [AA] genotype is a predictive or prognostic biomarker.

rs16260 (CDH1):

The cell adhesion protein Cadherin1 (E-cadherin) is a member of the calcium-dependent cadherin superfamily. Loss of function has been involved in progression of cancer. The rs16260 [A] allele in the CDH1 promoter has been demonstrated to reduce transcriptional efficiency of cadherin1. Further the −160A allele of CDH1 has been described as a susceptibility factor for the development of gastric cancer.

In this study, rs16260 [AA] genotype carriers are statistically overrepresented in the FAS responder. This may suggest that the [AA] genotype is a putative predictive biomarker.

rs11615 (ERCC1) and rs396991 (FCGR3A):

The two SNPs rs11615 (ERCC1, DNA repair protein "Excision repair cross-complementation group 1") and rs396991 (FCGR3A, low affinity immunoglobulin gamma Fc region receptor III-A) both show a correlation of genotypes (ERCC1 [TT], FCGR3A [TG] and [TT]) with prolonged PFS. This may suggest that these SNPs are predictive or prognostic biomarkers.

The invention claimed is:

1. A method of treating a human cancer patient having a CLDN18.2-positive tumor, said method comprising
   a. determining or having determined a genotype for at least one single-nucleotide polymorphism in a sample obtained from the cancer patient, the at least one single-nucleotide polymorphism including FCGR3A rs396991;
   b. identifying the cancer patient as a likely responder to treatment with an anti-CLDN18.2 antibody based on the patient having a heterozygous FCGR3A rs396991 [TG] genotype or a homozygous FCGR3A rs396991 [TT] genotype; and
   c. administering the anti-CLDN18.2 antibody to the human cancer patient.

2. The method of claim 1, wherein the antibody comprises a heavy chain having the amino acid sequence of SEQ ID NO: 17 or 51 or an antigen-binding fragment thereof and a light chain having the amino acid sequence of SEQ ID NO: 24 or an antigen-binding fragment thereof.

3. The method of claim 1, wherein the antibody comprises a heavy chain having the amino acid sequence of SEQ ID NO: 17 or 51 and a light chain having the amino acid sequence of SEQ ID NO: 24.

4. The method of claim 3, wherein the cancer is gastroesophageal cancer.

5. The method of claim 4, wherein the cancer is metastatic gastroesophageal cancer.

6. The method of claim 4, wherein the cancer is an advanced adenocarcinoma of the stomach or the lower esophagus.

7. The method of claim 1, further comprising determining or having determined a genotype for at least one additional single-nucleotide polymorphism in the sample, wherein the at least one additional single-nucleotide polymorphism is MUC1 rs4072037, DNMT3A rs1550117, SMAD4 rs12456284, EGF rs4444903, CDH1 rs16260, or ERCC1 rs11615.

8. The method of claim 1, wherein the sample is a blood sample.

9. A method of treating a human cancer patient, said method comprising:
   administering an anti-CLDN18.2 antibody to the patient, wherein the patient has been determined to have a heterozygous FCGR3A rs396991 [TG] genotype or a homozygous FCGR3A rs396991 [TT] genotype.

10. The method of claim 9, wherein the anti-CLDN18.2 antibody comprises a heavy chain having the amino acid sequence of SEQ ID NO: 17 or 51 or an antigen-binding fragment thereof and a light chain having the amino acid sequence of SEQ ID NO: 24 or an antigen-binding fragment thereof.

11. The method of claim 9, wherein the anti-CLDN18.2 antibody comprises a heavy chain having the amino acid sequence of SEQ ID NO: 17 or 51 and a light chain having the amino acid sequence of SEQ ID NO: 24.

12. The method of claim 11, wherein the cancer is gastroesophageal cancer.

13. The method of claim 12, wherein the cancer is metastatic gastroesophageal cancer.

14. The method of claim 12, wherein the cancer is an advanced adenocarcinoma of the stomach or the lower esophagus.

15. The method of claim 9, wherein the cancer is gastroesophageal cancer.

16. The method of claim 15, wherein the cancer is metastatic gastroesophageal cancer.

17. The method of claim 9, wherein the patient has been determined to have a homozygous MUC1 rs4072037 [AA] genotype, a heterozygous DNMT3A rs1550117 [GA] genotype, a heterozygous SMAD4 rs12456284 [GA] genotype, a homozygous EGF rs4444903 [AA] genotype, a homozygous CDH1 rs16260 [AA] genotype, or a homozygous ERCC1 rs11615 [TT] genotype.

18. A method of detecting a state of a single-nucleotide polymorphism (SNP) in a human patient having a CLDN18.2-positive cancer, said method comprising:
   obtaining a sample from a patient having a CLDN18.2-positive cancer, the sample comprising genomic DNA, wherein the patient has been determined to have a CLDN18.2-positive cancer; and
   detecting which nucleotide is present at both alleles of FCGR3A rs396991 in the sample, wherein the detecting comprises (i) contacting a detection reagent with a target FCGR3A rs396991-containing nucleic acid and (ii) detecting hybridization between the detection reagent and the target FCGR3A rs396991-containing nucleic acid, wherein the state of the FCGR3A rs396991 SNP is homozygous [GG], homozygous [TT], or heterozygous [TG];
   identifying the patient as a likely responder to treatment with an anti-CLDN18.2 antibody based on the patient having a heterozygous FCGR3A rs396991 [TG] genotype or a homozygous FCGR3A rs396991 [TT] genotype; and
   administering the anti-CLDN18.2 antibody to the patient.

19. The method of claim 18, wherein the anti-CLDN18.2 antibody comprises a heavy chain having the amino acid sequence of SEQ ID NO: 17 or 51 or an antigen-binding fragment thereof and a light chain having the amino acid sequence of SEQ ID NO: 24 or an antigen-binding fragment thereof.

20. The method of claim 18, wherein the anti-CLDN18.2 antibody comprises a heavy chain having the amino acid sequence of SEQ ID NO: 17 or 51 and a light chain having the amino acid sequence of SEQ ID NO: 24.

21. The method of claim 20, wherein the cancer is gastroesophageal cancer.

22. The method of claim 21, wherein the cancer is metastatic gastroesophageal cancer.

23. The method of claim 21, wherein the cancer is an advanced adenocarcinoma of the stomach or the lower esophagus.

24. The method of claim 18, further comprising detecting which nucleotide is present at both alleles of at least one additional single-nucleotide polymorphism (SNP) in the sample, wherein the detecting comprises (i) contacting a detection reagent with a target SNP-containing nucleic acid and (ii) detecting hybridization between the detection reagent and the target SNP-containing nucleic acid;

wherein the at least one additional SNP is MUC1 rs4072037, DNMT3A rs1550117, SMAD4 rs12456284, EGF rs4444903, CDH1 rs16260, or ERCC1 rs11615.

* * * * *